United States Patent
Wengel

(10) Patent No.: US 10,731,154 B2
(45) Date of Patent: Aug. 4, 2020

(54) ACYL-AMINO-LNA AND/OR HYDROCARBYL-AMINO-LNA OLIGONUCLEOTIDES

(71) Applicant: Arcturus Therapeutics, Inc., San Diego, CA (US)

(72) Inventor: Jesper Wengel, Langeskov (DK)

(73) Assignee: ARCTURUS THERAPEUTICS, INC., San Diego, CA (US)

( * ) Notice: Subject to any disclaimer, the term of this patent is extended or adjusted under 35 U.S.C. 154(b) by 84 days.

(21) Appl. No.: 15/550,884

(22) PCT Filed: Feb. 15, 2016

(86) PCT No.: PCT/EP2016/053202
§ 371 (c)(1),
(2) Date: Aug. 14, 2017

(87) PCT Pub. No.: WO2016/128583
PCT Pub. Date: Aug. 18, 2016

(65) Prior Publication Data
US 2018/0030437 A1 Feb. 1, 2018

(30) Foreign Application Priority Data

Feb. 15, 2015 (DK) .................................. 2015 00090
Aug. 3, 2015 (DK) .................................. 2015 00440
Nov. 10, 2015 (DK) .................................. 2015 00711
Nov. 10, 2015 (DK) .................................. 2015 00712

(51) Int. Cl.
*C07H 21/04* (2006.01)
*C12N 15/113* (2010.01)
*C12N 15/115* (2010.01)
*C12N 15/11* (2006.01)
*C12Q 1/6876* (2018.01)

(52) U.S. Cl.
CPC .......... *C12N 15/113* (2013.01); *C12N 15/111* (2013.01); *C12N 15/115* (2013.01); *C12Q 1/6876* (2013.01); *C12N 2310/11* (2013.01); *C12N 2310/16* (2013.01); *C12N 2310/315* (2013.01); *C12N 2310/321* (2013.01); *C12N 2310/323* (2013.01); *C12N 2310/3231* (2013.01); *C12N 2310/341* (2013.01); *C12N 2310/346* (2013.01); *C12N 2310/3515* (2013.01); *C12Q 2600/136* (2013.01); *C12Q 2600/158* (2013.01); *C12Q 2600/178* (2013.01)

(58) Field of Classification Search
None
See application file for complete search history.

(56) References Cited

U.S. PATENT DOCUMENTS

2014/0343123 A1  11/2014  Prakash et al.
2015/0368642 A1  12/2015  Alb k et al.

FOREIGN PATENT DOCUMENTS

| WO | WO-2003095467 A1 | 11/2003 |
| WO | 2009039862 A2 | 4/2009 |
| WO | WO-2013166155 A1 | 11/2013 |
| WO | WO-2014118267 A1 | 8/2014 |

OTHER PUBLICATIONS

Fluiter, On the in Vitro and in Vivo Properties of Four Locked Nucleic Acid Nucleotides Incorporated Into an Anti-H-Ras Antisense Oligonucleotide, 2005, Chembiochem—A European Journal of Chemical Biology, vol. 6, No. 6, pp. 1104-1109.
Sorensen, Functionalized LNA (locked nucleic acid):high-affinity hybridization of oligonucleotides containing N-acylated and N-alkylated 2'- amino—LNA monomers, Chemical Communications—Chemcom, Royal Society of Chemistry, 2003, No. 17, pp. 2130-2131.
Hojland, LNA (locked nucleic acid) and analogs as triplex-forming oligonucleotides, Organic & Biomolecular Chemistry, 2007, vol. 5, No. 15, pp. 2375-2379.
Johannsen, Amino acids attached to 2'-amino-LNA: synthesis and excellent duplex stability, Organic & Biomolecular Chemistry, 2011, vol. 9, No. 1, pp. 243-252.
Lundin, Biological Activity and Biotechnological Aspects of Locked Nucleic Acids, Advances in Genetics, 2013, vol. 82, pp. 47-107.

(Continued)

*Primary Examiner* — Kimberly Chong
(74) *Attorney, Agent, or Firm* — Mintz Levin Cohn Ferris Glovsky and Popeo PC; Marc Morley; Mridula Sherin

(57) ABSTRACT

A single stranded oligonucleotide containing two or more acyl-amino-LNA or hydrocarbyl-amino-LNA nucleotide monomers, in which other nucleotide monomers can be DNA, RNA or chemically modified nucleotide monomers;

in which the monomers of the oligonucleotide are linked by phosphodiester linkages and/or phosophorothioate linkages and/or phosphotriester linkages, in which the acyl and hydrocarbyl groups of the acyl-amino-LNA and hydrocarbyl-amino-LNA monomers are optionally substituted and thus optionally contain one or more hydroxyl group(s), amino group(s), thio group(s), oxo group(s), alkylthio group(s), ether group(s), and/or thiol (mercapto) group(s), and in which the acyl and hydrocarbyl groups of the acyl-amino-LNA and hydrocarbyl-amino-LNA monomers are linear or branched chains, cyclic or a combination of both, provided that the total number of carbon atoms in each acyl and hydrocarbyl group is less than 30.

21 Claims, 12 Drawing Sheets

Specification includes a Sequence Listing.

(56) References Cited

OTHER PUBLICATIONS

Madsen, Large Scale Synthesis of 2'-Amino-LNA Thymine and 5-Methylcytosine Nucleosides, The Journal of Organic Chemistry, 2012, vol. 77, No. 23, pp. 10718-10728.

Integrated DNA Technologies, Designing Antisense Oligonucleotides, 2005 and 2011, pp. 1-16.

Integrated DNA Technologies, Antisense Technologies, 2005 and 2011, pp. 1-11.

Geary, Pharmacokinetics, biodistribution and cell uptake of antisense oligonucleotides, 2015, Adv. Drug Delivery Reviews, vol. 87, pp. 46-51.

Astakhova, Scaffolding along Nucleic Acid Duplexes Using 2'-Amino-Locked Nucleic Acids, Accounts of Chemical research, 2014, vol. 47, pp. 1768-1777.

Ikeda, Impacts of PEGylation on the Gene and Oligonucleotide Delivery System, J Applied Polymer Science, 2014, vol. 40293, pp. 1-10.

Masaki, Enhancement of exon skipping in mdx52 mice by 2'-O-methyl-2-thioribothymidine incorporation into phosphorothioate oligonucleotides, Med Chem Commun, 2015, vol. 6, pp. 630-633.

Prakash, 2'-O-[2-(Methylthio)ethyl]-Modified Oligonucleotide: An analogue of 2'-O-[2-(Methoxy)-ethyl]-Modified Oligonucleotide with Improved Protein Binding Properties and High Binding Affinity to Target RNA, 2002, Biochemistry, vol. 41, pp. 11642-11648.

Wan, Synthesis, biophysical properties and biological activity of second generation antisense oligonucleotides containing chiral phosphorothioate linkages, 2014, Nucleic Acids research, vol. 42, pp. 13456-13468.

Zhang, Down-modulation of cancer targets using locked nucleic acid (LNA)-based antisense oligonucleotides without transfection, 2011, Gene Therapy, vol. 18, pp. 326-333.

Biessen, E. A., et al., "Targeted delivery of oligodeoxynucleotides to parenchymal liver cells in vivo." Biochemical Journal 340.Pt 3 (1999): 783.

Maier, Martin A., et al., "Synthesis of antisense oligonucleotides conjugated to a multivalent carbohydrate cluster for cellular targeting." Bioconjugate chemistry 14.1 (2003): 18-29.

Prakash, et al., Targeted delivery of antisense oligonucleotides to hepatocytes using triantennary N-acetyl galactosamine improves potency 10-fold in mice, Nucleic Acids Research, 2014, pp. 8796-8807, vol. 42, No. 13.

ACYL-AMINO-LNA AND/OR HYDROCARBYL-AMINO-LNA OLIGONUCLEOTIDES

FIELD OF THE INVENTION

The invention relates to a single stranded oligonucleotide containing two or more acyl-amino-LNA or hydrocarbyl-amino-LNA nucleotide monomers. The oligonucleotide may be a gapmer or mixmer. The oligonucleotide may be used as antisense oligonucleotide for downregulation of target RNA such as by RNase H-mediated gene silencing, or for modulation of RNA. The oligonucleotide may be an aptamer that targets a protein or peptide or a target molecule other than a nucleic acid. The invention also relates to a method of mediating gene silencing in a cell or an organism using the oligonucleotide. The invention also relates to a method of examining the function of a gene in a cell or organism using the oligonucleotide. The invention further relates to a method of assessing whether an agent acts on a gene product using the oligonucleotide. The invention moreover relates to the oligonucleotide for use in therapy of an animal or a human and to a pharmaceutical composition comprising the oligonucleotide.

BACKGROUND

In the antisense technology, RNA is targeted by Watson-Crick hybridization of a complementary antisense oligonucleotide (AON). The goal of inhibiting gene expression in a specific way may be accomplished by preventing mRNA maturation, blocking translation or more commonly by induction of target RNA degradation [Crooke, S. T. *Biochim. Biophys. Acta* 1999, 1489, 31-44; Zamaratski, E.; Pradeepkumar, P. I.; Chattopadhyaya, J. *J. Biochem. Biophys. Methods* 2001, 48, 189-208]. To be effective the AON has to be able to enter the cell, be stable toward nucleases, be non-toxic and show high binding affinity and specificity toward the target mRNA. Considerable progress with respect to stability and binding has been made by use of chemically modified AONs. Introducing nucleotide analogues with constrained North type (N-type; C3'-endo type) furanose ring conformations has proven successful with respect to obtaining strong binding toward an RNA target, with LNA (locked nucleic acid) being a prominent example. An LNA monomer contains an O2'-C4' methylene linkage that locks the furanose ring in an N-type conformation leading to unprecedented binding affinity toward complementary RNA for AONs composed of a mixture of e.g. LNA and DNA nucleotides [Koshkin, A. A.; Singh, S. K.; Nielsen, P.; Rajwanshi, V. K.; Kumar, R.; Meldgaard, M.; Olsen, C. E.; Wengel, J. *Tetrahedron* 1998, 54, 3607-3630; Obika, S.; Nanbu, D.; Hari, Y.; Andoh, J.-i.; Mono, K.-i.; Doi, T.; Imanishi, T. *Tetrahedron Lett.* 1998, 39, 5401-5404; Petersen, M.; Wengel, J. *Trends Biotechnol.* 2003, 21, 74-81; Vester, B.; Wengel, J. *Biochemistry* 2004, 43, 13233-13241]. Incorporation of LNA nucleotides into an AON induces formation of almost canonical A-form helix structures of the duplexes formed with RNA complements [Petersen, M.; Bondensgaard, K.; Wengel, J.; Jacobsen, J. P. *J. Am. Chem. Soc.* 2002, 124, 5974-5982; Nielsen, K. E.; Rasmussen, J.; Kumar, R.; Wengel, J.; Jacobsen, J. P.; Petersen, M. *Bioconjugate Chem.* 2004, 15, 449-457; Nielsen, C. B.; Singh, S. K.; Wengel, J.; Jacobsen, J. P. *J. Biomol. Struct. Dyn.* 1999, 17, 175-191; Nielsen, K. E.; Singh, S. K.; Wengel, J.; Jacobsen, J. P. *Bioconjugate Chem.* 2000, 11, 228-238], and LNA thus can be characterized as a structural mimic of RNA though it lacks the 2'-OH group of an RNA nucleotide. Contrary, the stereoisomeric α-L-LNA monomer is locked in a conformation that results in AONs that structurally mimic DNA whereby duplexes between DNA/α-L-LNA mixmers and RNA adopt intermediate A/B duplex geometries [Nielsen, K. M.; Petersen, M.; Hakansson, A. E.; Wengel, J.; Jacobsen, J. P. *Chem. Eur. J.* 2002, 8, 3001-3009; Petersen, M.; Håkansson, A. E.; Wengel, J.; Jacobsen, J. P. *J. Am. Chem. Soc.* 2001, 123, 7431-7432. Remarkably, both LNA and α-L-LNA nucleotides induce very high RNA binding affinities of AONs with increases in thermal denaturation temperatures ($T_m$ values) of ~2-8° C. per modification [Vester, B.; Wengel, J. *Biochemistry* 2004, 43, 13233-13241; Sørensen, M. D.; Kvaerno, L.; Bryld, T.; Hakansson, A. E.; Verbeure, B.; Gaubert, G.; Herdewijn, P.; Wengel, J. *J. Am. Chem. Soc.* 2002, 124, 2164-2176]. LNA-modified oligonucleotides have likewise shown promising properties with respect to targeting microRNAs, i.e. as so-called anti-MiRs, and one LNA oligonucleotide targeting microRNA 122 is currently in clinical phase 2 studies as a drug to treat HCV infection [www.santaris.com]. Furthermore LNA-modified oligonucleotides have shown promise as splice-modulating compounds [B. Bestas et al., *J. Clin. Investigation*, 2014, 9, 4067], and also as so-called blockmirs which are single-stranded oligonucleotides which target the microRNA binding sites [www.mirrx.dk].

A number of other locked nucleotides, i.e. analogs of LNA, such as BNAs, carbocyclic-LNAs and CEt have been studied in the context of therapeutic oligonucleotides [Rahman, S. M. A et al., *Chem. Lett.* 2009, 38, 512][Zhou, C. and Chattopadhyaya, J., *Curr. Opin. Drug Disc. Devel.*, 2009, 12, 2180][Seth, P. P. and Swayze, E. E., in Natural Products in Medicinal Chemistry, Ed. Hanessian, S, Wiley-VCH, Weinheim, 1$^{st}$ ed., 2014, 203-439].

The efficiency of gapmer antisense oligonucleotides containing modified nucleotides is often limited by their inability to induce degradation of target mRNA by the ubiquitous RNase H enzyme. Specifically, RNase H is incompatible with substrate duplexes with N-type nucleotides like LNA or O2'-alkylated-RNA nucleotides dispersed throughout the AON [Sørensen, M. D.; Kvaerno, L.; Bryld, T.; Hakansson, A. E.; Verbeure, B.; Gaubert, G.; Herdewijn, P.; Wengel, J. *J. Am. Chem. Soc.* 2002, 124, 2164-2176; Lima, W. F.; Nichols, J. G.; Wu, H.; Prakash, T. P.; Migawa, M. T.; Wyrzykiewicz, T. K.; Bhat, B.; Crooke, S. T. *J. Biol. Chem.* 2004, 279, 36317-36326]. Such O2'-alkylated-RNA nucleotides can for example be 2'-O-methyl-RNA nucleotides or 2'-O-methoxyethyl-RNA (2'-MOE-RNA) nucleotides.

Aptamers, which herein are defined as short single-stranded oligonucleotides, are alternative oligonucleotide constructs for drug development. Aptamers adopt well-defined three-dimensional shapes which enables targeting of for example peptides, proteins, small molecules, viruses and live cells [Eckstein, F., *Expert Opin. Biol. Ther.* 2007, 7, 1021; Famulok, M. et al., Chem. Rev. 2007, 107, 3715; Thiel, K. W. and Giangrande, P. H., Oligonucleotides 2009, 19, 209; Mayer, G. *Angew. Chem. Int. Ed.* 2009, 48, 2672]. In solution, the nucleotides together constituting the sequence of the aptamer have the potential to form segments of base-paired regions which will induce folding of the molecule into a complex three-dimensional shape thereby ideally allowing the aptamer to bind tightly against the surface of its target molecule. It is the capability of aptamers to form diverse molecular shapes depending on their sequence that enable them to form binding interactions with targets. Aptamers are typically generated by evolution of specific sequences against a given target by so-called in vitro evolution using the process known as SELEX (systematic evolution of ligands by exponential enrichment) [Ellington, A. D. and Szostak, J. W., *Nature* 1990, 346, 818; Turk, C. and Gold, L., *Science* 1990, 249, 5059]. SELEX involves iterative rounds of selection and polymerase-catalyzed enrichment (PCR) of bound aptamers selected from a pool of nucleic acid components, i.e. from a large library of typically e.g. 50-100 nucleotide long sequences involving a central variable (sequence randomized) region flanked by two primer-binding regions.

Aptamers are versatile drug candidates as they can be evolved against extracellular targets like receptors or certain signaling molecules. They can also be evolved against intracellular components and thereby mediate a biological response once internalized into cells. Aptamers have been applied in vivo to specifically deliver an anti-cancer siRNA to prostate cancer cells [Dassie, J. P. et al., *Nature Biotechnology* 2009, 27, 839]. Intracellular application of aptamers is a challenging task due to poor intracellular delivery caused by their relatively large size and polyanionic character. Another challenge is biodistribution as some unconjugated oligonucleotides are excreted rapidly via the kidneys upon i.v. administration. PEGylation (chemical attachment by so-called conjugation of polyethylene glycol), and lipid nanoparticulate formulation are example approaches which have been applied to improve biodistribution [Veronese, F. M. et al., *Drug Disc. Today* 2005, 10, 1451].

One aptamer has been approved as drug (pegaptanib; to treat age-related macular degeneration upon local administration in the eye) and others are or have been in various stages of clinical development towards different diseases [Famulok, M., *J. Med. Chem.* 2009, 52, 6951]. These therapeutic candidates have generally been obtained by so-called post-SELEX modification of aptamers which have been evolved by a full SELEX procedure. Post-SELEX modification typically involves truncation into shorter aptamer candidates, conjugation (e.g. pegylation) for improved biodistribution, and/or incorporation of chemically modified nucleotides for improved biostability. Post-SELEX chemical modification is necessary as only rather few modified nucleoside triphosphates, for example 2'-fluoro-RNA, 2'-amino-RNA and 5-substituted pyrimidine nucleoside triphosphates [Mayer, G., *Angew. Chem. Int. Ed.* 2009, 48, 2672], are substrates for the polymerase-catalyzed reactions required for efficient SELEX procedures. Post-SELEX modifications are typically performed in iterative rounds of synthesis and binding assays/biological evaluation to ensure that modifications are compatible with the desired aptamer properties.

AS1411 is a 26-mer G-rich oligodeoxynucleotide. Like the vast majority of aptamers its nucleoside constituents are linked together by natural phosphodiester (PO) linkages as these are highly compatible with the SELEX procedure. AS1411 has been reported to fold as a stable dimeric G-quadruplex structure [Collie G. W. and Parkinson, G. N. *Chem. Soc. Rev.* 2011, 40, 5867]. It can cause induction of cell death in human cancer cell lines and has little effect on normal cells, and it has been tested in phase I and II clinical trials of patients with advanced cancer [Reyes-Reyes, E. M. et al., *Cancer Res.* 2010, 70, 8617]. Its target has been identified as nucleolin though its mechanism of action is not completely understood. It has been proposed that nucleolin-binding leads to selective uptake of AS-1411 into cancer cells. More recent studies have confirmed the involvement of nucleolin in the action of AS1411 and have suggested that uptake of AS1411 may be by macropinocytosis [Reyes-Reyes, E. M. et al., *Cancer Res.* 2010, 70, 8617].

Some derivatives of and properties of acyl-amino-LNA and hydrocarbyl (such as alkyl)-amino-LNA monomers and oligomers are known from published scientific papers. A review on amino-LNA derivatives—including acyl-amino-LNA and alkyl-amino-LNA [I. K. Astakhova and J. Wengel, *Acc. Chem. Res.*, 2014, 47, 1768] has recently been published. When compared to the corresponding DNA/RNA oligonucleotides, acyl-amino-LNA and hydrocarbyl (such as alkyl)-amino-LNA oligonucleotides generally display increased affinity towards complementary DNA/RNA strands much in line with the increased affinity observed for the corresponding LNA oligonucleotides.

Glycyl-amino-LNA and palmitoyl-amino-LNA monomers can be mixed with LNA and DNA monomers [Johannsen, M. W. et al., *Org. Biomol. Chem.*, 2011, 9, 243]. Nucleotide monomers composed of pyrene linked to amino-LNA monomers via an N2'-linker have been reported to be useful as fluorescent probes, and acyl-amino-LNA derivatives containing various amino acids as acyl group have been shown to be compatible (mixable in the same strand or oligonucleotide) with DNA nucleotides, and 2'-amino-LNA and 2'-N-methyl-amino LNA monomers have been shown to be useful in gapmer antisense oligonucleotides [see I. K. Astakhova and J. Wengel, *Acc. Chem. Res.*, 2014, 47, 1768 and references cited therein].

It has been reported that oligonucleotides containing a piperazino-modified 2'-amino-LNA monomer exhibit high duplex stability and remarkable nuclease resistance. The nuclease resistance was for the studied oligonucleotide (mixmer with DNA, phosphodiester (PO) linkages) even significantly increased compared to the corresponding oligonucleotide containing a parent amino-LNA monomer instead of the piperazino-modified 2'-amino-LNA monomer [Lou, C., Vester, B. and Wengel, J. *Chem. Comm.* 2015. 19, 4024-4027]. And the induced nucleolytic stability was shown to be entended towards the 3'-end of the oligonucleotide several DNA nucleotides away from the piperazino-modified 2'-amino-LNA monomer. These results demonstrate that the oligonucleotides of the invention, even as all-PO oligonucleotide, display significant stabilization against nucleolytic degradation.

No reports have been published on the use of acyl-amino-LNA, e.g. glycyl- or palmitoyl-amino-LNA-containing oligonucleotides for RNA targeting in vivo, e.g. in the context of antisense, antimir or blockmir, or as compounds able to modulate splicing events.

The invention discloses the use of oligonucleotides containing two or more acyl-amino-LNA and/or hydrocarbyl-amino-LNA monomers as RNA-targeting constructs for therapeutic or diagnostic purposes. Examples of the invented constructs include gapmer antisense constructs, mixmer antisense constructs, antimir constructs, blockmir constructs and aptamer constructs.

The use of gapmer antisense constructs, mixmer antisense constructs, antimir constructs, blockmir constructs and aptamer constructs containing 2'-amino-LNA ("2'-NH") and 2'-N-methyl-amino-LNA ("2'-NCH$_3$") monomers as only amino-LNA type monomer are not included in the present invention.

The invention further discloses the use of oligonucleotides containing two or more acyl-amino-LNA and/or hydrocarbyl-amino-LNA monomers as nucleic acid aptamers as non-RNA-targeting constructs for therapeutic or diagnostic purposes.

The oligonucleotides of the invention can be used to mediate RNA targeting in organs of animals or humans not reached effectively by standard single-stranded RNA-targeting oligonucleotides, e.g. phosphorothioate-LNA oligonucleotides or phosphorothioate-MOE oligonucleotides. Such effect is mediated because a wide range of hydrocarbyl and acyl groups can be attached to the N2'-position of amino-LNA monomers in hydrocarbyl-amino-LNA and acyl-amino-LNA monomers and incorporated into oligonucleotides. Thereby modulation of the pharmacokinetic properties of the oligonucleotide can be realized. For example, hydrophobic acyl or hydrocarbyl (such as alkyl) groups ease permeation across cell membranes and may furthermore lead to improved accumulation in liver tissues. Furthermore, many fatty acid residues like palmitoyl or myristoyl, when attached to the N2'-position of amino-LNA monomers in an oligonucleotide of the invention, lead to binding to plasma proteins, e.g. albumin, which in turn may lead to improved circulation time in the blood and improved tissue distribution and uptake.

The presence of two of such fatty acid conjugated amino-LNA modifications (e.g. palmitoyl-amino-LNA residues) is, in the invention, one particularly preferred design in order to achieve improved circulation time in the blood and improved tissue distribution and uptake for phosphodiester or phosphorothioate based oligonucleotides, e.g. gapmers or mixmers for targeting mRNA or non-coding RNAs—e.g. for miRNA targeting, modulation of splice switching, miRNA target site blockage, gene silencing or upregulation of gene expression. In the case of phosphodiester variants of such antisense oligonucleotides, the stability against nucleolytic degradation is increased compared to the corresponding oligonucleotides composed e.g. as LNA-DNA-LNA or BNA-DNA-BNA gapmers or as LNA/DNA, BNA/DNA, LNA/2'-O-Me-RNA, BNA/2'-O-Me-RNA or LNA/DNA/2'-OMe-RNA mixmers, in particular when two of the LNA or BNA monomers are exchanged by the acyl- or amino-LNA monomers of the invention.

Also acyl or hydrocarbyl (such as alkyl) groups carrying one or more positive charge(s) can be beneficial for cell membrane permeability and tissue targeting. Other options include conjugation with carbohydrates like galactose units or CPPs (cell penetrating peptides). The presence of at least two acyl-amino-LNA and/or hydrocarbyl (such as alkyl)-amino-LNA monomer in an oligonucleotide improves the nuclease stability relative to unmodified or LNA-containing reference oligonucleotides. The fact that groups of different sizes can be attached without disturbing the RNA-targeting capability enables engineering of desired biostability e.g. engineering of increased stability against degradation by nucleases.

For antisense applications, so-called gapmers are often used. These are chimeric AONs with a central continuous stretch of RNase H recruiting nucleotides (typically DNA or phosphorothioate DNA nucleotides but alternatively e.g. phosphorothioate FANA nucleotides [Lok, C. N.; Viazovkina, E.; Min, K. L.; Nagy, E.; Wilds, C. J.; Damha, M. J.; Parniak, M. A. *Biochemistry* 2002, 41, 3457-3467]) flanked by affinity-enhancing modified nucleotides (e.g. LNA, α-L-LNA or O2'-alkylated RNA nucleotides) [Jepsen, J. S.; Sørensen, M. D.; Wengel, J. *Oligonucleotides* 2004, 14, 130-146; Monia, B. P.; Lesnik, E. A.; Gonzalez, C.; Lima, W. F.; McGee, D.; Guinosso, C. J.; Kawasaki, A. M.; Cook, P. D.; Freier, S. M. *J. Biol. Chem.* 1993, 268, 14514-14522; Kurreck, J.; Wyszko, E.; Gillen, C.; Erdmann, V. A. *Nucleic Acids Res.* 2002, 30, 1911-1918; Frieden, M.; Christensen, S. M.; Mikkelsen, N. D.; Rosenbohm, C.; Thrue, C. A.; Westergaard, M.; Hansen, H. F.; Orum, H.; Koch, T. *Nucleic Acids Res.* 2003, 31, 6365-6372]. It has been found that the optimal gap size is motif-dependent, that a right balance between gap size and affinity is required [Kurreck, J.; Wyszko, E.; Gillen, C.; Erdmann, V. A. *Nucleic Acids Res.* 2002, 30, 1911-1918], and that the presence of one or two DNA-mimicking α-L-LNA monomers within the gap is compatible, at least in part, with RNase H activity [Sørensen, M. D.; Kvaerno, L.; Bryld, T.; Hakansson, A. E.; Verbeure, B.; Gaubert, G.; Herdewijn, P.; Wengel, J. *J. Am. Chem. Soc.* 2002, 124, 2164-2176; Frieden, M.; Christensen, S. M.; Mikkelsen, N. D.; Rosenbohm, C.; Thrue, C. A.; Westergaard, M.; Hansen, H. F.; Orum, H.; Koch, T. *Nucleic Acids Res.* 2003, 31, 6365-6372].

Acyl- and hydrocarbyl (such as alkyl)-amino-LNA monomers have previously been incorporated into DNA strands, and therefore procedures for preparation of their phosphoramidite building blocks for automated oligonucleotide synthesis have been reported as well as procedures for their incorporation into oligonucleotides (e.g. DNA, RNA, LNA, UNA (unlocked nucleic acids) or 2'-OMe-RNA oligonucleotides) [see I. K. Astakhova and J. Wengel, *Acc. Chem. Res.*, 2014, 47, 1768 and references cited therein, in particular Johannsen, M. W. et al., *Org. Biomol. Chem.*, 2011, 9, 243].

The following structural and functional features are considered optimal for antisense type oligonucleotides (such as gapmers or mixmers) by the inventor:
(a) relatively small size, i.e. below 20 nucleotides in total;
(b) containing phosphodiester (PO), or a majority of PO, internucleoside linkages instead of PS internucleoside linkages;
(c) a long half-life in serum;
(d) limited excretion via the kidneys (urine);
(e) stability against nucleolytic degradation;
(f) ability to penetrate cell membranes and mediate modulation of gene expression without the addition of transfecting agents or the use of nanoparticulate formulations.

Fulfilment of a) is advantageous for production purposes, and may further aid cell membrane permeation and/or biodistribution. Incorporation of LNA-type nucleotides (or BNA-type nucleotides) is the preferred way of reducing the length of a therapeutic oligonucleotide because of the high RNA target affinity induced by LNA (or BNA) nucleotides [Obad, S. et al. *Nature Genetics* 2011, 43, 371-378]. Incorporation of LNA (or BNA) nucleotides may also enable the development of short therapeutic aptamers as the excellent hybridization properties of LNA (or BNA) nucleotides may promote intramolecular structuring even for shorter aptamer sequences.

Fulfilment of b) is advantageous in order to avoid the formation of diastereoisomeric mixtures generated at each PS (phosphorothioate) linkage. A 16-mer all-PS standard antisense oligonucleotide as an example, may exist as a mixture of $2^{15}$ (=32.768) distinct molecules [Wan, W. B. et al., *Nucleic Acids Res.* 2014, 42, 13456-13468], of which some may contribute to the desired therapeutic action while others may give rise, for example, to undesired effects. Some off-target effects of oligonucleotides containing PS linkages may originate from non-specific binding to proteins and immune-related side effects [Jastrzebska et al. *Org. Biomol. Chem.* 2015, 13, 10032-10040 and references cited therein]. These challenges of standard PS-oligonucleotides has prompted research into synthesis of P-stereodefined PS oligonucleotides, but preparation of such compounds requires the use and development of cumbersome synthetic methods and have not furnished improved therapeutic derivatives [Wan, W. B. et al., *Nucleic Acids Res.* 2014, 42, 13456-13468; Jastrzebska et al. *Org. Biomol. Chem.* 2015, 13, 10032-10040]. Therapeutic oligonucleotides containing preferentially, or exclusively, PO linkages are considered desired as they would show less off-target effects.

Fulfilment of c), d) and e) is desirable to obtain the pharmacokinetic properties needed for oligonucleotide drug development. To fulfil these three points, PS linkages have typically been used to achieve binding to plasma proteins thus reducing excretion via the kidneys, and furthermore protection against degradation by nucleases. However, still a significant amount of undesired and rapid excretion via the kidneys is observed. Alternatively lipid derivatives, most typically cholesteryl, have been applied to mediate binding to plasma proteins. This has in particular been studied for siRNA constructs (double stranded RNAs) [Wolfrum, C. et al., *Nature Biotech.* 2007, 25, 1149-1157; Howard, K. A., Bienk, K. and Kragh-Hansen, U. WO2014/005596], but still no lipid derivative of an siRNA or a single stranded oligonucleotide has been approved as a drug, and the challenges prevail [Wittrup, A. and Lieberman, J., *Nature Rev. Gen.* 2015, 16, 543-552]. Interestingly, promising gene silencing activity using transfection agent and albumin was reported for singly or doubly cholesteryl-modified siRNAs, but notably not for the corresponding C12-C16 fatty acid functionalized siRNAs [Wolfrum, C. et al., *Nature Biotech.* 2007, 25, 1149-1157; Howard, K. A., Bienk, K. and Kragh-Hansen, U. WO2014/005596].

For aptamers, fulfilment of c) and d) has typically been achieved by conjugation with PEG (polyethylene glycol) units [Hirota, M. et al, *Nucleic Acids Ther.* 2016, 26, 10-19]. This however is a non-preferred solution. Firstly, conjugation with PEG is an additional complication towards obtaining the final drug component, and secondly have immune reactions against PEG units and rapid clearance of PEGylated systems been reported [Yang, Q. and Lai, S. K., *Advanced Review* 2015, 7, 655-677].

It has been reported that efficient so-called gymnotic delivery (or unassisted delivery with no transfection agent used) and concomitant gene modulation activity of an oligonucleotide correlates particularly well with in vivo activity, and such efficient unassisted permeation into cells is therefore now considered highly important for oligonucleotide drug development efforts. Efficient unassisted delivery has been demonstrated for high-affinity LNA-type antisense gapmers [Stein, C. A. et al. *Nucleic Acids Res.* 2010, 38, e3; Zhang, Y. et al. *Gene Therapy* 2011, 18, 326-333] and for the relatively high-affinity 2'-FANA oligonucleotides [Souleimanian, N. et al., *Mol. Ther. Nucleic Acids* 2012, 1, e43]. Fulfilment of f) has thus been achieved by using oligonucleotides containing high-affinity monomers, but notably only in the context of PS linkages. It should be mentioned that the $IC_{50}$ values obtained for inhibition of gene expression typically have been in the low micromolar range, significantly above the nanomolar range often obtained when using transfection agents. Further it should be noted that standard all-PO oligonucleotides have failed to display activity or uptake under unassisted delivery conditions.

Based on the single stranded oligonucleotides reported so far in the literature, no construct has fulfilled all six desirable points a)-f) listed and discussed above. The following summarizes some key points based on reported data:

1) All-PS oligonucleotides display improved pharmacokinetic properties relative to all-PO oligonucleotides but their therapeutic use is hampered by undesirable off-target effects and a relatively high rate of renal clearance;
2) Double cholesteryl-functionalization of siRNA constructs have been shown to be compatible with efficient gene silencing in vitro using transfection-/permeation-aiding molecules, while double palmitoyl-functionalization of the same siRNAs failed to demonstrate efficient gene silencing under similar conditions;
3) Improved circulatory half-life, i.e. reduced renal clearance rate, has been reported for cholesteryl and palmitoyl functionalized siRNA;
4) Stability against exo- and endonuclease for single stranded oligonucleotides has typically required the use of chemically modified nucleotides, either at most of the nucleotide positions in the strand, or with the use of PS linkages in substantially all linkage positions.
5) Single stranded oligonucleotides containing more than 30-40% RNA nucleotides and PO linkages are typically unstable towards nucleolytic degradation.
6) Efficient cell uptake and gene silencing activity under unassisted delivery conditions requires the use of single stranded oligonucleotides having PS linkages in most of the linkage positions.

It is an object of the present invention to provide single-stranded oligonucleotides having high transfection efficiency in eukaryotic cells or cells of an organism such as an animal or a human, even if no transfectants are used.

It is an object of the present invention to provide oligonucleotides that have long half-life in serum of an animal such as a mammal.

It is an object of the present invention to provide antisense oligonucleotides which, when bound to RNA target sequences, are efficient substrates of RNase H type enzymes.

It is another object of the invention to provide antisense oligonucleotides which, without being a substrate of RNase H, bind strongly to target RNA, thereby leading to modulation of gene expression. The target RNA can be mRNA or non-coding RNAs.

It is another object of the invention to provide antisense oligonucleotides with improved properties with regard to stability towards enzymatic degradation in cell cultures or in vivo. Still another object is to provide antisense oligonucleotides that display improved bioavailability, increased tissue distribution or otherwise improved properties, e.g. improved gene silencing effect in vivo, relative to the corresponding antisense oligonucleotides not containing two or more acyl-amino-LNA and/or hydrocarbyl-amino-LNA monomers.

It has surprisingly been found by the inventor that the single stranded oligonucleotides of the invention containing two or more acyl-amino-LNA or hydrocarbyl (such as alkyl)-amino-LNA nucleotide monomers fulfil all desirable points a)-f) listed above. The oligonucleotides of the invention thus display the following:

7) they are efficient as relatively short strands because of the LNA-type high-affinity hybridization mediated by the acyl-amino-LNA and hydrocarbyl (such as alkyl)-amino-LNA nucleotide monomers;
8) they are efficiently taken up by cells and display gene modulation activity under unassisted delivery conditions, and that even as all-PO oligonucleotides (i.e. having PO at all linkages or at most of the linkages), but also as all-PS derivatives:
9) they display increased half-life in serum as all-PO and all-PS derivatives, even when compared to the corresponding all-PS oligonucleotides without the acyl-amino-LNA and hydrocarbyl-amino-LNA nucleotide monomers;
10) they show less accumulation in the kidneys as all-PO and all-PS derivatives, even when compared to the corresponding all-PS oligonucleotides without the acyl-amino-LNA and alkyl-amino-LNA nucleotide monomers;

11) they show satisfactory stability against nucleolytic degradation as also testified by their substantial serum half-life, and that both as all-PO and all-PS derivatives;
12) they display the ability to penetrate cell membranes and mediate modulation of gene expression without the need of addition of transfecting agents or the use of nanoparticulate formulations, and that both as all-PO and all-PS derivatives.

SUMMARY OF THE INVENTION

The present invention provides inter alia the following items 1) to 46):
1) a single stranded oligonucleotide containing two or more acyl-amino-LNA or alkyl-amino-LNA nucleotide monomers, in which other nucleotide monomers can be DNA, RNA or chemically modified nucleotide monomers,
   in which the monomers of the oligonucleotide are linked by phosphodiester linkages and/or phosphorothioate linkages and/or phosphotriester linkages,
   in which the acyl and alkyl groups of the acyl-amino-LNA and alkyl-amino-LNA monomers are optionally substituted and thus optionally contain one or more hydroxyl group(s), amino group(s), thio group(s), oxo group(s), alkylthio group(s), ether group(s), and/or thiol (mercapto) group(s), and
   in which the acyl and alkyl groups of the acyl-amino-LNA and alkyl-amino-LNA monomers are linear or branched chains, cyclic or a combination of both, provided that the total number of carbon atoms in each acyl and alkyl group is less than 30.
2) A single stranded oligonucleotide containing two or more acyl-amino-LNA or hydrocarbyl-amino-LNA nucleotide monomers, in which other nucleotide monomers can be DNA, RNA or chemically modified nucleotide monomers;
   in which the monomers of the oligonucleotide are linked by phosphodiester linkages and/or phosphorothioate linkages and/or phosphotriester linkages,
   in which the acyl and hydrocarbyl groups of the acyl-amino-LNA and hydrocarbyl-amino-LNA monomers are optionally substituted and thus optionally contain one or more hydroxyl group(s), amino group(s), thio group(s), oxo group(s), alkylthio group(s), ether group(s), and/or thiol (mercapto) group(s), and
   in which the acyl and hydrocarbyl groups of the acyl-amino-LNA and hydrocarbyl-amino-LNA monomers are linear or branched chains, cyclic or a combination of both, provided that the total number of carbon atoms in each acyl and hydrocarbyl group is less than 30.
(3) The single stranded oligonucleotide according to above item 1 or 2, wherein at least 50%, preferably at least 70%, more preferably at least 90%, and most preferably at least 95% of all internucleoside linkages of said oligonucleotide are phosphodiester linkages.
(4) The single stranded oligonucleotide according to above items 1 to 3, wherein at most 40%, preferably at most 30%, more preferably at most 20%, and most preferably at most 10% of nucleotide monomer moieties of said oligonucleotide are ribonucleotide monomer moieties.
5) The single stranded oligonucleotide according to any one of above items 1 to 4, wherein said hydrocarbyl-amino-LNA nucleotide monomers are alkyl-amino-LNA nucleotide monomers.
6) The single stranded oligonucleotide according to any one of above items 1 to 5, wherein said oligonucleotide contains at least two N-acyl-amino-LNA nucleotide monomers, or at least two N-hydrocarbyl-amino-LNA nucleotide monomers, or at least one N-acyl-amino-LNA nucleotide monomer and at least one N-hydrocarbyl-amino-LNA nucleotide monomer.
7) The single stranded oligonucleotide according to any one of above items 1 to 6, said oligonucleotide containing one or two nucleotide monomer units (moieties) that are linked to a cholesteryl moiety.
8) The single stranded oligonucleotide according to any one of above items 1 to 7, wherein the acyl moieties of said acyl-amino-LNA nucleotide monomer units are N-alkanoyl, N-alkenyol and/or N-alkynoyl moieties, each having from 4 to 30 carbon atoms, preferably from 7 to 22 carbon atoms, more preferably from 10 to 22 carbon atoms, said acyl moiety being unsubstituted or substituted with one or more groups selected from hydroxy, $C_1$-$C_6$ alkoxy, amino, $C_1$-$C_6$ mono or dialkylamino, oxo, thiol, and $C_1$-$C_6$ alkylthio groups.
9) The single stranded oligonucleotide according to any one of above items 1, 2, 3, 4, 5, 6, 7, or 8, wherein said oligonucleotide comprises at least 7 nucleotide monomer units, preferably at least 8, nucleotide monomer units, more preferably at least 11 nucleotide monomer units, and even more preferably at least 12 monomer units.
10) The single stranded oligonucleotide according to any one of above items 1 to 9, wherein all nucleotide monomer units of said oligonucleotide are linked by phosphodiester linkages.
11) The single stranded oligonucleotide according to any one of above items 1 to 10, which is a gapmer, an aptamer, or a mixmer.
12) The single stranded oligonucleotide according to any one of above items 1 to 11, wherein said oligonucleotide has, from the 5'-end to the 3'-end, three segments: a 5'-end segment of at least 2 nucleotide units, a central binding segment of at least 6 nucleotide units in length, and a 3'-end segment of at least 2 nucleotide units in length,
wherein said oligonucleotide contains at least two acyl-amino-LNA or hydrocarbyl-amino-LNA nucleotide monomers in either the 5'-end segment or the 3'-end segment but none in the central segment; or contains at least one N-acyl-amino-LNA or hydrocarbyl-amino-LNA nucleotide monomer in each of said end segments, but none in the central segment.
13) The single stranded oligonucleotide according to any one of above items 1 to 11, wherein the oligonucleotide is a gapmer of the following constitution:

$$N_V\text{-}M_Y\text{-}N_Z,$$

in which M denotes a nucleotide monomer compatible with RNase H degradation of the target RNA, N denotes monomers selected from among affinity-enhancing nucleotide monomers, acyl-amino-LNA and/or hydrocarbyl-amino-LNA monomers, and DNA nucleotide monomers, and wherein V, Y and Z signify the numbers of the monomers in the segments, and where the hyphens indicate separation between the two wing sequence segments $N_V$ and $N_Z$ and the gap sequence segment $M_Y$; the numbers V and Z may vary between 2 and 8 and the number Y may vary between 6 and 14, provided that the sum of V+Z+Y is maximum 30, with the provision that
at least one acyl-amino-LNA and/or hydrocarbyl-amino-LNA monomer is present in each of the wing segments, i.e. the segments composed of the N monomers; or
at least two acyl-amino-LNA and/or hydrocarbyl-amino-LNA monomers are present in one of the wing segments, i.e. the segments composed of the N monomers.

14) The single stranded oligonucleotide according to above item 13, in which the oligonucleotide is of the following constitution 5'-(L)$_{2-4}$-(D)$_{6-10}$-(L)$_{2-4}$, where D denotes a DNA nucleotide monomer and L denotes an affinity-enhancing nucleotide monomer or an acyl-amino-LNA and/or hydrocarbyl-amino-LNA monomer, provided that at least one acyl-amino-LNA and/or hydrocarbyl-amino-LNA monomer is present in each of the wing segments, i.e. the segments composed of the L monomers; or at least two acyl-amino-LNA and/or hydrocarbyl-amino-LNA monomers are present in one of the wing segments, i.e. the segments composed of the L monomers.

15) An antisense oligonucleotide according to any one of above items 1 to 14, which is able to mediate gene regulation by RNase-H mediated antisense RNA targeting.

16) The single stranded oligonucleotide according to any one of above items 1 to 11, in which at least two acyl-amino-LNA and/or hydrocarbyl-amino-LNA monomers are present in one of the half sequence segments, i.e. the 5'-end half of the oligonucleotide sequence or the 3'-end half of the oligonucleotide sequence, provided that the central nucleotide monomer is not included in any of the two half sequence segments if the total number of nucleotides in the oligonucleotide is uneven; or one of said at least two acyl-amino-LNA and/or hydrocarbyl-amino-LNA monomers optionally can be the central nucleotide monomer if the total number of nucleotide monomers in the oligonucleotide is uneven.

17) A single stranded oligonucleotide having the constitution 5'-(N)$_{7-26}$, wherein N denotes at least one affinity-enhancing monomer and in addition may denote any other type of nucleotide monomer, provided that at least two N nucleotides are acyl-amino-LNA and/or hydrocarbyl-amino-LNA monomers and that each sequence element, i.e. the 5'-end half of the oligonucleotide sequence and the 3'-end half of the oligonucleotide sequence, each contains at least one acyl-amino-LNA and/or hydrocarbyl-amino-LNA monomer, or at least two acyl-amino-LNA and/or hydrocarbyl-amino-LNA monomers are present in one of the half sequence elements, i.e. the 5'-end half of the oligonucleotide sequence or the 3'-end half of the oligonucleotide sequence, provided that the central nucleotide monomer is not included in any of the two sequence elements if the total number of nucleotides is uneven, or one of said at least two acyl-amino-LNA and/or hydrocarbyl-amino-LNA monomers optionally may be the central nucleotide monomer if the total number of nucleotide monomers in the oligonucleotide is uneven, and in which the monomers of the oligonucleotide are linked by phosphodiester linkages and/or phosophorothioate linkages and/or phosphotriester linkages, in which the acyl and hydrocarbyl groups of the acyl-amino-LNA and hydrocarbyl-amino-LNA monomers are optionally substituted and thus optionally contain one or more hydroxyl group(s), amino group(s), thio group(s), oxo group(s), alkylthio group(s), ether group(s), or thiol (mercapto) group(s), and in which the acyl and hydrocarbyl groups of the acyl-amino-LNA and hydrocarbyl-amino-LNA monomers can be linear or branched chains, cyclic or a combination of both, provided that the total number of carbon atom in each acyl and hydrocarbyl group is less than 30.

18) The single stranded oligonucleotide according to item 17, wherein at least 50%, preferably at least 70%, more preferably at least 90%, and most preferably at least 95% of all internucleoside linkages in said oligonucleotide are phosphodiester linkages.

19) The single stranded oligonucleotide according to item 17 or 18, wherein at most 40%, preferably at most 30%, more preferably at most 20%, and most preferably at most 10% of nucleotide monomers of said oligonucleotide are ribonucleotide monomers.

20) The single stranded oligonucleotide according to any one of above items 17 to 19, in which the constitution is 5'-(N)$_{7-12}$, where N denotes affinity enhancing nucleotides and at least two acyl-amino-LNA and/or hydrocarbyl-amino-LNA monomers such that each of said sequence elements contains at least one acyl-amino-LNA and/or hydrocarbyl-amino-LNA monomer.

21) The single stranded oligonucleotide according to any one of above items 17 to 19, in which the constitution is 5'-(N)$_{12-22}$, where N denotes at least four LNA-type affinity-enhancing monomers, a number of DNA or 2'-OMe-RNA monomers and at least two acyl-amino-LNA and/or hydrocarbyl-amino-LNA monomers and such that each of said sequence elements contains at least one acyl-amino-LNA and/or hydrocarbyl-amino-LNA monomer.

22) A single stranded oligonucleotide according to any one of above items 17 to 19, in which the constitution is 5'-(N)$_{15-22}$, where N denotes at least three LNA-type affinity-enhancing monomers, a one or more 2'-OMe-RNA monomers and at least two acyl-amino-LNA and/or hydrocarbyl-amino-LNA monomers and such that each of said sequence elements contains at least one acyl-amino-LNA and/or hydrocarbyl-amino-LNA monomer.

23) A single stranded oligonucleotide according to any one of above items 17 to 19, in which the constitution is 5'-(N)$_{7-12}$, where N constitutes affinity enhancing nucleotides and at least two acyl-amino-LNA and/or hydrocarbyl-amino-LNA monomers such that at least two acyl-amino-LNA and/or hydrocarbyl-amino-LNA monomers are present in one of the half sequence elements, i.e. the 5'-end half of the sequence or the 3'-end half of the sequence, provided that the central nucleotide monomer is not included in any of the two sequence elements if the total number of nucleotides is uneven; or one of said at least two acyl-amino-LNA and/or hydrocarbyl-amino-LNA monomers optionally may be the central nucleotide monomer if the total number of nucleotides monomers in the oligonucleotide is uneven.

24) A single stranded oligonucleotide according to any one of above items 17 to 19, in which the constitution is 5'-(N)$_{12-22}$, where N denotes at least four LNA-type affinity-enhancing monomers, a number of DNA or 2'-OMe-RNA monomers and at least two acyl-amino-LNA and/or hydrocarbyl-amino-LNA monomers and such that at least two acyl-amino-LNA and/or hydrocarbyl-amino-LNA monomers are present in one of the half sequence elements, i.e. the 5'-end half of the sequence or the 3'-end half of the sequence, provided that the central nucleotide monomer is not included in any of the two sequence elements if the total number of nucleotides is uneven; or one of said at least two acyl-amino-LNA and/or hydrocarbyl-amino-LNA monomers optionally may be the central nucleotide monomer if the total number of nucleotides monomers in the oligonucleotide is uneven.

25) A single stranded oligonucleotide according to any one of above items 17 to 19, in which the constitution is 5'-(N)$_{15-22}$, where N denotes at least three LNA-type affinity-enhancing monomers, a number of 2'-OMe-RNA monomers and at least two acyl-amino-LNA and/or hydrocarbyl-amino-LNA monomers and such that at least two acyl-amino-LNA and/or hydrocarbyl-amino-LNA monomers are present in one of the half sequence elements, i.e. the 5'-end half of the sequence or the 3'-end half of the sequence, provided that the central nucleotide monomer is not included in any of the two sequence elements if the total number of nucleotides is uneven; or one of said at least two acyl-amino-LNA and/or hydrocarbyl-amino-LNA monomers optionally can be the central nucleotide monomer if the total number of nucleotides monomers in the oligonucleotide is uneven.

26) A method of mediating gene silencing in a cell or an organism, comprising contacting said cell or organism with an oligonucleotide, such as an antisense oligonucleotide, as defined in any of above items 1 to 25.

27) The method according to item 26, said method being performed in vitro or on an isolated cell; or said method being performed in vivo in a mammal (such as a whole animal or in a human), e.g. by administering said oligonucleotide to said mammal.

28) The method according to item 26, wherein said oligonucleotide has complementarity to a target gene or target RNA expressed in said cell or organism for mediating silencing of the target gene or target RNA, preferably mediated by RNase H.

29) n oligonucleotide as defined in any one of above items 1 to 25 for use in therapy of an animal or a human.

30) The oligonucleotide for the use according to item 29, wherein said oligonucleotide has complementarity to a target gene or target RNA for mediating silencing of the target gene or target RNA, preferably mediated by RNase H.

31) A method of examining the function of a gene in a cell or organism, comprising:
introducing an oligonucleotide as defined in any of above items 1 to 25 that targets RNA for gene silencing into the cell or organism, thereby producing a test cell or test organism; maintaining the test cell or test organism under conditions under which gene silencing occurs, thereby producing a test cell or test organism in which RNA levels of the gene is reduced; and
observing the phenotype of the test cell or organism produced and optionally comparing the observed phenotype with the phenotype of an appropriate control cell or control organism, thereby providing information about the function of the gene.

32) The method according to item 31, used for determination of whether a gene product is a suitable target for therapeutic intervention.

33) The method according to above items 31 or 32, said method being performed in vitro or on an isolated cell.

34) The method according to item 31 and 32, said method being performed in vivo in a whole animal or in a human.

35) A method of assessing whether an agent acts on a gene product, comprising the steps:
introducing an antisense oligonucleotide as defined in any one of above items 1 to 25, that targets RNA for mediating gene silencing into a cell or organism, thereby producing a test cell or test organism,
maintaining the test cell or test organism under conditions under which gene silencing occurs, thereby producing a test cell or test organism in which RNA levels of the gene is reduced, introducing the agent into the test cell or test organism, and
observing the phenotype of the test cell or organism and optionally comparing the observed phenotype with the phenotype of a control cell or control organism, thereby providing information about whether the agent acts on the gene product.

36) The method according to item 35, said method being performed in vitro or on an isolated cell.

37) The method according to item 35, said method being performed in vivo in a whole animal or in a human.

38) A pharmaceutical composition comprising an oligonucleotide according to any one of above items 1 to 25 and a pharmaceutically acceptable diluent, carrier or adjuvant.

39) The oligonucleotide of any of above items 1 to 25 for use as a medicament or in a method of treating the human or animal body by therapy.

40) The oligonucleotide of any of above items 1 to 25 for use in a diagnostic method practiced on the human or animal body.

41) The oligonucleotide of any of above items 1 to 25 for use for disease prognostics.

42) The oligonucleotide of any of above items 1 to 25 for research use.

43) The oligonucleotide of any one of above items 1 to 25, in which the two or more acyl-amino-LNA and/or hydrocarbyl-amino-LNA nucleotide monomers are selected among glycyl-amino-LNA monomers, palmitoyl-amino-LNA-monomers, myristoyl-amino-LNA monomers, and acetyl-amino-LNA-monomers.

44) The antisense oligonucleotide of any one of above items 1 to 25, in which the two or more acyl-amino-LNA and/or hydrocarbyl-amino-LNA nucleotide monomer are palmitoyl-amino-LNA-monomer(s), myristoyl-amino-LNA monomer(s) or amino-LNA monomers N-acylated with another fatty acid acyl group, said fatty acid acyl group preferably being a fatty acid acyl group of a saturated fatty acid and/or preferably comprising from 10 to 18 carbon atoms.

45) The oligonucleotide of any of the preceding items in which the oligonucleotide contains one or more conjugating group attached at the 3'- and/or the 5'-end of the oligonucleotide.

46) A reagent containing the oligonucleotide of any one of above items 1 to 25.

The inventors has surprisingly found that the oligonucleotides of the invention having two or more acyl-amino-LNA or hydrocarbyl (such as alkyl)-amino-LNA nucleotide monomer units are useful e.g. as single stranded oligonucleotide therapeutics by displaying high transfection efficiency for eukaryotic cells even if no transfectants are used (unassisted delivery into cells), by displaying high stability against nuclease-mediated degradation, by binding to albumin, by showing long half-life in serum, by showing biological activity. After parenteral administration, the serum half-life is high and bioavailability is also high. Thus, oligonucleotides of the invention are very useful e.g. for therapeutic purposes, as well as for diagnostic purposes, notably in vivo.

BRIEF DESCRIPTION OF THE DRAWINGS

FIG. 2, part 2-2. PAGE (polyacrylamide gel electrophoresis) of annealing of albumin/ODN complexes, using ODN with one (ON7455; left) and two (ODN7456; right) palmitoly-amino-LNA modifications or no palmitoly-amino-LNA modifications as control (ON7454) and visualized by SYBR gold staining. ODNs are here with phosphorothioate internucleoside linkages. The upper arrows show where albumin runs in the gel; the visible bands originate from the stained ODN (bound to albumin) whereas the lower stained band is the unbound ODN.

FIG. 2, part 2-3. PAGE of annealing of albumin/ODN complexes for the ODN with phosphodiester linkages (ON7451; left) and for the ODN with phosphorothioate linkages (ON7454; right) as visualization by SYBR gold staining.

DETAILED DESCRIPTION OF THE INVENTION

Figure 1:
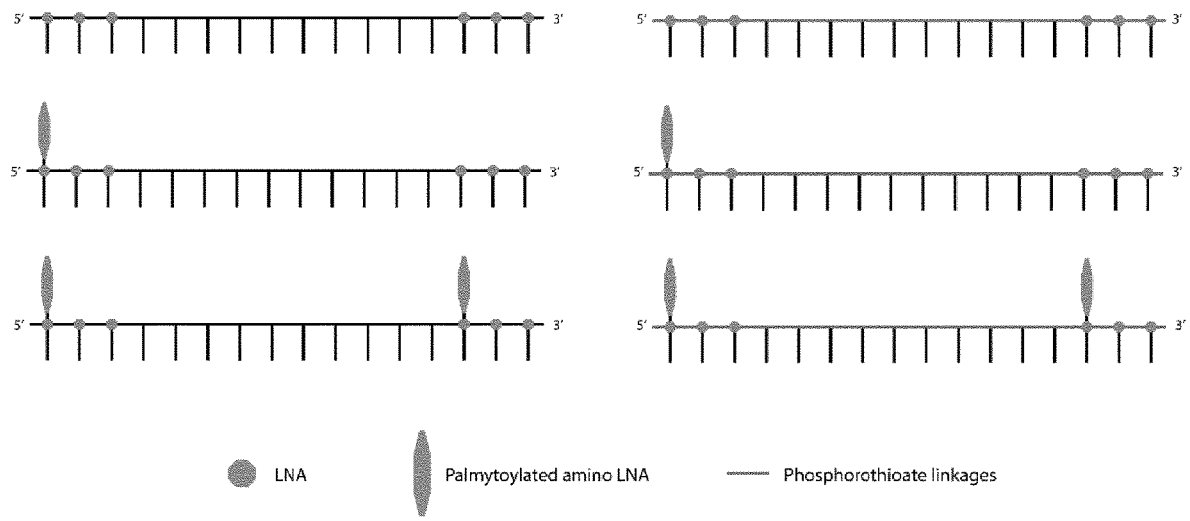
FIG. 1 Schematic overview of antisense oligonucleotides (ODNs) evaluated for albumin binding in Example 4.

The invention provides a single-stranded oligonucleotide containing two or more acyl-amino-LNA or hydrocarbyl (such as alkyl)-amino-LNA nucleotide monomers, in which other nucleotide monomers can be DNA, RNA or chemically modified nucleotide monomers; in which the monomers of the oligonucleotide are linked by phosphodiester linkages (also referred to herein as "PO") and/or phosphorothioate linkages (also referred to herein as "PS") and/or phosphotriester linkages; in which the acyl and hydrocarbyl groups of the acyl-amino-LNA and hydrocarbyl-amino-LNA monomers are optionally substituted and thus optionally contain one or more hydroxyl group(s), amino group(s), thio group(s), oxo group(s), alkylthio group(s), ether group(s), and/or thiol (mercapto) group(s); and in which the acyl and hydrocarbyl (such as alkyl) groups of the acyl-amino-LNA and hydrocarbyl (such as alkyl)-amino-LNA monomers are linear or branched chains, cyclic or a combination of both, provided that the total number of carbon atoms in each acyl and hydrocarbyl group is less than 30.

The oligonucleotide of the invention comprises at least 10 nucleotide monomer units, preferably at least 11 nucleotide monomer units, more preferably at most 12 monomer units. The oligonucleotide may consist of from 10 to 30 monomer units, preferably from 11 to 30 monomer units, more preferably from 12 to 26 monomer units, even more preferably from 14 to 24 monomer units, and even more preferably from 14 to 20 monomer units. In one embodiment, the oligonucleotide has from 12 to 16 nucleotide monomer units. Since the nucleotide monomer units are linked to form the oligonucleotide, the term "nucleotide monomer unit" or, briefly, "monomer unit" indicates that the nucleotide monomer is not an isolated molecule, but a chemical moiety linked to one or two other nucleotide monomer units in the oligonucleotide. The term "monomer" in the context of an oligonucleotide means a monomer unit or moiety. The term "oligonucleotide" may herein be abbreviated "oligo". The abbreviations "ODN" and "AON" mean antisense oligonucleotide.

In the oligo of the invention, the monomers of the oligonucleotide are linked by phosphodiester linkages and/or phosphorothioate linkages and/or phosphotriester linkages. A given oligonucleotide may have only one type of these linkages, two types of these, or even all three types of linkages. In preferred embodiments, in the single stranded oligonucleotide, at least 50%, preferably at least 70%, more preferably at least 80%, more preferably at least 90%, and most preferably at least 95% of internucleoside linkages are phosphodiester linkages (PO), and remaining internucleoside linkages may be phosphorothioate linkages and/or phosphotriester linkages. In a preferred embodiment, the internucleoside linkages of the oligonucleotide of the present invention are all-PO (all-phosphodiester). There is also an embodiment with all-PS (all-phosphorothioate) or a mixture of PO and PS internucleoside linkages. These types of linkages as well as methods of automated synthesis of oligos having these linkages are known to the skilled person from general knowledge.

The nucleobase (briefly: "base") of the nucleotide monomer units are not particularly limited in the oligos of the invention; they may be the standard nucleobases adenine, guanine, cytosine, thymine and uracil, or any derivative thereof or any chemically modified nucleobase, with 5-methylcytosine and 5-substituted uracil being particularly preferred examples.

The oligo of the invention has two or more acyl-amino-LNA or hydrocarbyl (such as alkyl)-amino-LNA nucleotide monomers. The acyl-amino-LNA or hydrocarbyl-amino-LNA is a nucleotide monomer unit having a 2'-amino-LNA moiety, i.e. having the 2'-oxygen atom of LNA replaced by an acylated or hydrocarbylated (such as alkylated) 2'-nitrogen atom. Amino-LNA is known in the prior art, see e.g. the review of I. K. Astakhova and J. Wengel, *Acc. Chem. Res.*, 2014, 47, 1768. Thus, the acyl-amino-LNA is 2'-N-acyl-2'-amino LNA and the hydrocarbyl-amino-LNA is 2'-N-hydrocarbyl-2'-amino LNA. The nucleobase of the acyl-amino-LNA or hydrocarbyl-amino LNA is not specifically limited and may be adenine, guanine, cytosine, thymine and uracil, or any derivative thereof or any chemically modified nucleobase. For ease of preparation of 2'-amino-LNA nucleosides, the base of the 2'-amino-LNA moiety may be thymine or 5-methylcytosine.

The other nucleotide monomer units in the oligo of the invention are, with regard to their ribose moiety or its derivative, not specifically restricted. They may be DNA or RNA or may have chemically modified ribose derivatives. They may thus be DNA, RNA, LNA, BNA, UNA, 2'-amino-LNA, α-L-LNA, 2'-F-RNA, 2'-O-alkyl-RNA and/or 2'-O-alkoxyalkyl-RNA monomer units or mixtures thereof. 2'-O-Alkyl-RNA monomers may be 2'-O—$C_1$-$C_{26}$-alkyl-RNA monomer units. 2'-O-Alkyloxyalkyl-RNA monomer units may be 2'-O—$C_1$-$C_6$-alkyloxy-$C_1$-$C_{26}$-alkyl-RNA monomer units such as 2'-O-methoxyethyl-RNA units. BNA covers a number of locked nucleotides with bicyclic ribose units having a linker between the C2' and C4' atoms, including carbocyclic-LNAs and CEt [Rahman, S. M. A et al., *Chem. Lett.* 2009, 38, 512][Zhou, C. and Chattopadhyaya, J., *Curr. Opin. Drug Disc. Devel.*, 2009, 12, 2180], and UNA is a class of nucleotide monomers having the ribose unit substituted by an acyclic unit, preferably a 2',3'-seco-RNA unit [Langkjr, N., Pasternak, A. and Wengel, J., *Bioorg. Med. Chem.* 2009, 17, 5420-5]. In the single stranded oligonucleotide of the invention, at most 30% of nucleotide monomers of the oligonucleotide may be ribonucleotide monomers (RNA). Preferably, at most 20%, more preferably at most 10%, even more preferably at most 5% of nucleotide monomers of the oligonucleotide are ribonucleotide monomers. In an important embodiment, the oligonucleotide does not have ribonucleotide monomer units. In one embodiment, the other nucleotide monomer units are all deoxyribonucleotide monomer units (DNA), and in yet another embodiment, they are all 2'-O-methyl-RNA monomer units. In a further embodiment, the other monomer units are DNA and RNA units, however such that the total number of RNA units is no larger than 30% of the total number of nucleotide monomer units in the oligo. In line with general understanding and IUPAC definition, the term ribonucleotide refers to a nucleotide having no substitution at the ribose moiety except the nucleobase in 1'-position and a phosphate moiety in 5'-position. Accordingly, the term ribonucleotide monomer (unit) refers to nucleotide monomer (units) having no substitution at the ribose moiety except the nucleobase in 1'-position and possible internucleoside linkages in 5'-position and, optionally, in 3'-position. In more detail, a ribonucleotide is unsubstituted in 2'-position and at the 2'-OH group.

An example of other nucleotide monomer units in the oligo of the invention are nucleotide monomer units chemically modified, preferably at the ribose moiety, with—e.g. antenna-like—mono-, di- or trimeric galactosyl or N-acetylamino galactosyl moieties. The invention includes, as a preferred embodiment, 3'-end or 5'-end conjugates of the oligonucleotides with such mono-, di- or trimeric galactosyl or N-acetylamino galactosyl moieties. The (e.g. antenna-like) mono-, di- or trimeric galactosyl or N-acetylamino galactosyl moieties may be linked to the 2'-amino group of amino-LNA nucleotide monomer units in an oligonucleotide. Recently, a number of reports have illustrated how targeted delivery of antisense oligonucleotides to the liver, e.g. to hepatocytes, has been achieved using conjugates of antisense oligonucleotides with (e.g. antenna-like) mono-, di- or trimeric galactosyl or N-acetylamino galactosyl moieties. These have been linked to the antisense oligonucleotide using a number of different linkages—both stable linkages or linkages which are cleaved in vivo—and general methods for their preparation are described in the following two references: [Prakash, T. P. et al., *Nucleic Acids Res.* 2014, 42, 8796-8807; Albk, N. et al., US20150368642]. These methods can be used for design and synthesis of similar conjugation of the antisense oligonucleotides of this invention with antenna-like mono-, di- or trimeric galactosyl or N-acetylamino galactosyl moieties.

The number of acyl-amino-LNA and hydrocarbyl-amino-LNA nucleotide monomers in the oligo of the invention is at least two. Generally, not more than 40%, preferably not more than 30%, more preferably not more than 20% of the total number of monomer units in the oligo are acyl-amino-LNA and hydrocarbyl-amino-LNA nucleotide monomers. The number of acyl-amino-LNA and hydrocarbyl-amino-LNA nucleotide monomers in the oligo may be from 2 to 8, preferably from 2 to 6, more preferably from 2 to 4, such as 2 or 3. These numbers refer to the total of acyl-amino-LNA and hydrocarbyl-amino-LNA nucleotide monomers in the oligo. The oligo of the invention may contain at least two N-acyl-amino-LNA nucleotide monomers, or at least two N-hydrocarbyl-amino-LNA nucleotide monomers, or at least one N-acyl-amino-LNA nucleotide monomer and at least one N-hydrocarbyl-amino-LNA nucleotide monomer. In one embodiment, the oligo of the invention contains acyl-amino-LNA nucleotide monomer units in the content just defined, but may not have hydrocarbyl-amino-LNA nucleotide units. In another embodiment, the oligo of the invention contains hydrocarbyl-amino-LNA nucleotide monomer units in the content just defined, but may not have acyl-amino-LNA nucleotide units.

The at least two acyl-amino-LNA and/or hydrocarbyl-amino-LNA monomers of the oligo may be located close to the 5' and/or 3' ends of the oligo, and may be absent in a central region of the oligo. In one embodiment, they are all present at nucleotide positions 1 to 4, preferably 1 to 3, from the 5'-end of the oligo, wherein the 5'-terminal monomer unit is position 1; and/or they are present at nucleotide positions t to (t-3), preferably t to (t-2), from the 3'-end of the oligo, whereby the 3'-terminal monomer unit is position t.

In one embodiment, the at least two acyl-amino-LNA and/or hydrocarbyl-amino-LNA monomers are all present in one of the half sequence segments of the oligo, i.e. either in the 5'-end half of the sequence or the 3'-end half of the sequence. In an alternative embodiment, at least one acyl-amino-LNA and/or hydrocarbyl-amino-LNA monomer is present in each of the half sequence segments of the oligo, i.e. at least one in the 5'-end half of the sequence and a least one in the 3'-end half of the sequence. The central nucleotide monomer is not included in any of the two half sequence segments if the total number of nucleotide units in the oligo is uneven. In one embodiment, one of the at least two acyl-amino-LNA and/or hydrocarbyl-amino-LNA monomers is the central nucleotide monomer if the total number of nucleotide monomers in the oligonucleotide is uneven. The embodiments of this and the previous paragraph may be combined with the length definitions of the oligo given above, the preferred internucleoside linkages given above, the maximum numbers of RNA nucleotide monomers in the oligo given above, and/or with the numbers of the acyl-amino-LNA and hydrocarbyl-amino-LNA monomers in the oligo given above.

Next, the hydrocarbyl moiety of the hydrocarbyl-amino-LNA nucleotide units is described. The hydrocarbyl (such as alkyl) group of the hydrocarbyl (such as alkyl)-amino-LNA nucleotide units is a linear or branched chain, is cyclic (such as a cycloalkyl group), or is a combination of a cyclic group and a linear or branched chain. The total number of carbon atom in the hydrocarbyl (such as alkyl) group is less than 30. Preferably, the minimum number of carbon atoms in the hydrocarbyl (such as alkyl) group is 2, preferably 6, preferably 7, and more preferably 10. In one embodiment, the hydrocarbyl or alkyl group has from 6 to 30, preferably from 7 to 22, more preferably from 10 to 22 carbon atoms, even more preferable from 12 to 20 carbon atoms, and most preferably from 14 to 18 carbon atoms. Preferably, the hydrocarbyl group of the hydrocarbyl-amino-LNA nucleotide units is a linear or branched chain such as a linear or branched hydrocarbyl group. The hydrocarbyl group of the hydrocarbyl-amino-LNA nucleotide units may be unsubstituted or substituted as further defined below.

A hydrocarbyl group or moiety is a univalent group formed by removing a hydrogen atom from a hydrocarbon. The hydrocarbyl group may be saturated or unsaturated, it may be a linear, branched or a cyclic group, or a combination of any of these. Linear or branched hydrocarbyl groups are preferred. Examples of the preferred linear or branched hydrocarbyl groups are alkyl, alkenyl and alkynyl groups. Specific examples of preferred alkyl groups are N-ethyl, N-tetradecyl and N-hexadecyl groups, among which N-hexadecyl groups are most preferred. The most preferred hydrocarbyl groups are alkyl groups, notably linear or branched alkyl groups. Carbon atom numbers thereof are as given above.

Examples of the cyclic hydrocarbyl groups are ($C_4$-$C_8$-cycloalkyl) and ($C_4$-$C_8$-cycloalkenyl) groups, preferably ($C_5$-$C_7$ cycloalkyl) groups. Specific examples are cyclobutyl, cyclopentyl, cyclohexyl and cycloheptyl groups. The hydrocarbyl moieties may be unsubstituted or substituted as defined below. The cyclic alkyl groups may be cycloalkyl groups. Examples of the cyclic alkyl group are $C_4$-$C_8$ cycloalkyl groups, preferably $C_5$-$C_7$ cycloalkyl groups. Specific examples are cyclobutyl, cyclopentyl, cyclohexyl and cycloheptyl groups.

The combinations of linear or branched chains on the one hand and cyclic groups on the other hand in the hydrocarbyl or alkyl groups may be the following groups: cycloalkyl-alkyl groups, alkyl-cycloalkyl groups, dialkyl-cycloalkyl groups, alkyl-cycloalkyl-alkyl groups, and cycloalkyl-alkyl groups. The monovalent alkyl moieties attached to the cycloalkyl moieties in these combinations may be linear or branched and may have from 1 to 24 carbon atoms, preferable from 2 to 20 carbon atoms, more preferably from 3 to 16 carbon atoms, and most preferably from 4 to 12 carbon atoms. The total number of carbon atoms in these combinations may be as given above with regard to the carbon atom numbers of the hydrocarbyl groups.

The hydrocarbyl group (such as the alkyl group) of the hydrocarbyl-amino-LNA nucleotide monomers may be unsubstituted or substituted by one or more hydroxyl group(s), amino group(s), thio group(s), oxo group(s), alkylthio group(s), ether group(s), and/or thiol (mercapto) group(s). The alkylthio group may be a $C_1$-$C_6$ alkylthio group, preferably a $C_1$-$C_3$ alkylthio group. The ether group is a $C_1$-$C_{10}$ alkyloxy group, preferably a $C_1$-$C_6$ alkyloxy group, more preferably a $C_1$-$C_3$ alkyloxy group. Further possible substituents are a $C_1$-$C_3$ alkylamino group and a di($C_1$-$C_3$ alkyl)amino group. Thus, the hydrocarbyl (such as alkyl) group may be an hydrocarbyl group with the carbon atom numbers given above (e.g. a $C_7$-$C_{22}$ alkyl group) that may be substituted with one or more substituents selected from the group consisting of a hydroxyl group, an amino group, a thio group, an oxo group, a $C_1$-$C_6$ alkylthio group, a $C_1$-$C_6$ alkylthio group, preferably a $C_1$-$C_3$ alkylthio group, a $C_1$-$C_6$ alkyloxy group, preferably a $C_1$-$C_3$ alkyloxy group, a $C_1$-$C_3$ alkylamino group and a di($C_1$-$C_3$ alkyl)amino group.

The hydrocarbyl groups of multiple hydrocarbyl-amino-LNA nucleotide units in the oligo of the invention may be the same or different. As an alternative to hydrocarbyl-amino-LNA nucleotide monomers, the hydrocarbyl groups may be replaced by heterohydrocarbyl groups as defined below.

Next, the acyl moiety of the acyl-amino-LNA nucleotide units is described. The acyl group of the acyl-amino-LNA nucleotide monomer units is a group —C(=O)R linked to the 2'-N atom of the amino-LNA moiety to form an amide group, wherein R is an organyl group. The acyl groups of the acyl-amino-LNA monomer units of the oligo of the invention are linear or branched chains, cyclic or a combination of both, provided that the total number of carbon atom in each acyl group is less than 30.

The total number of carbon atoms in the acyl group may be at least 2, preferably at least 6, more preferably at least 7, and even more preferably at least 10. In one embodiment, the acyl group has from 4 to 30 carbon atoms, preferably from 6 to 30, preferably from 7 to 22, more preferably from 10 to 22 carbon atoms, even more preferable from 12 to 20 carbon atoms, and most preferably from 14 to 18 carbon atoms. Preferably, the acyl groups of the acyl-amino-LNA nucleotide units are linear or branched acyl groups.

The acyl group may be a hydrocarbylcarbonyl group or a heterohydrocarbyl-carbonyl, wherein the former are preferred. The heterohydrocarbyl moiety contains, apart from carbon and hydrogen atoms, from one to three heteroatoms, preferably one or two heteroatoms, selected from O, S or N, preferably O. Thus, the acyl group may be a heterohydrocarbylcarbonyl group having from 1 to 3 oxygen heteroatoms. The hydrocarbyl and heterohydrocarbyl moieties may be saturated or unsaturated, preferably they are saturated. The hydrocarbyl and heterohydrocarbyl groups may be unsubstituted or substituted as defined below.

The cyclic acyl groups may be cyclic hydrocarbylcarbonyl or heterohydrocarbyl-carbonyl groups. Examples of the cyclic group are ($C_4$-$C_8$-cycloalkyl)carbonyl groups, preferably ($C_5$-$C_7$ cycloalkyl)carbonyl groups. Specific examples are cyclobutylcarbonyl, cyclopentylcarbonyl, cyclohexylcarbonyl and cycloheptylcarbonyl groups. Corresponding heterohydrocarbylcarbonyl groups may be any of the just mentioned groups wherein from one to three $C_1$ units are replaced by O, S, N or NH units, preferably O. The hydrocarbyl and heterohydrocarbyl moieties may be unsubstituted or substituted as defined below.

The linear or branched chains as the acyl groups may be linear or branched hydrocarbylcarbonyl or heterohydrocarbylcarbonyl groups. The linear or branched chains (and the hydrocarbylcarbonyl groups) may be alkanoyl, alkenoyl or alkynoyl groups. Corresponding heterohydrocarbylcarbonyl may be any of the just mentioned groups wherein from one to three $C_1$ units are replaced by O, S, N or NH units, preferably O. These may have from 2 to 30 carbon atoms, preferably from 7 to 22 carbon atoms, more preferably from 10 to 22 carbon atoms, and most preferably from 14 to 18 carbon atoms. Preferred linear or branched chains (or linear or branched hydrocarbylcarbonyl groups) are alkanoyl groups, such as those derived from saturated fatty acids. Specific examples of preferred alkanoyl groups are N-acetyl, N-myristoyl and N-palmitoyl groups, among which N-palmitoyl groups are most preferred. The hydrocarbyl and heterohydrocarbyl moieties may be unsubstituted or substituted as defined below.

The combinations of linear or branched chains on the one hand and cyclic groups on the other hand in the acyl groups may be the following hydrocarbylcarbonyl groups: cycloalkyl-alkylcarbonyl groups, alkyl-cycloalkylcarbonyl groups, dialkyl-cycloalkylcarbonyl groups, alkyl-cycloalkyl-alkylcarbonyl groups, and cycloalkyl-alkylcarbonyl groups. Corresponding heterohydrocarbylcarbonyl may be any of the just mentioned groups wherein from one to three $C_1$ units are replaced by O, S, N or NH units, preferably O. The monovalent alkyl moieties attached to the cycloalkyl moieties in these combinations may be linear or branched and may have from 1 to 24 carbon atoms, preferable from 2 to 20 carbon atoms, more preferably from 3 to 16 carbon atoms, and most preferably from 4 to 12 carbon atoms. The total number of carbon atoms in these combinations may be as given above with regard to the carbon atom numbers of the acyl groups. The hydrocarbyl and heterohydrocarbyl moieties may be unsubstituted or substituted as defined below.

The acyl group of the acyl-amino-LNA nucleotide monomers, such as the hydrocarbylcarbonyl or heterohydrocarbylcarbonyl groups, may be unsubstituted or substituted by (or comprise) one or more hydroxyl group(s), amino group(s), thio group(s), oxo group(s), alkylthio group(s), ether group(s), and/or thiol (mercapto) group(s). The alkylthio group may be a $C_1$-$C_6$ alkylthio group, preferably a $C_1$-$C_3$ alkylthio group. The ether group is a $C_1$-$C_{12}$ alkyloxy group, preferably a $C_1$-$C_6$ alkyloxy group, preferably a $C_1$-$C_3$ alkyloxy group. Further possible substituents are a $C_1$-$C_3$ alkylamino group and a di($C_1$-$C_3$ alkyl)amino group. The hydrocarbylcarbonyl and (or heterohydrocarbylcarbonyl groups are acyl groups with the carbon atom numbers given above that may be substituted with one or more, preferably with one or two, substituents selected from the group consisting of a hydroxyl group, an amino group, a thio group, an oxo group, a $C_1$-$C_6$ alkylthio group, preferably a $C_1$-$C_3$ alkylthio group, a $C_1$-$C_6$ alkyloxy group, preferably a $C_1$-$C_3$ alkyloxy group, a $C_1$-$C_3$ alkylamino group and a di($C_1$-$C_3$ alkyl)amino group. In one embodiment, the hydrocarbylcarbonyl and/or heterohydrocarbylcarbonyl group has the carbon atom numbers given above that may be substituted with one or more substituents, preferably with one or two substituents, selected from the group consisting of a hydroxyl group, an oxo group, a $C_1$-$C_3$ alkylthio group, and a $C_1$-$C_3$ alkyloxy group.

In preferred embodiments, the acyl moieties (such as the hydrocarbylcarbonyl groups) of the acyl-amino-LNA nucleotide monomers are unsubstituted or substituted N-alkanoyl, N-alkenoyl or N-alkynoyl moieties having from 2 to 30 carbon atoms, preferably from 7 to 22 carbon atoms, more preferably from 10 to 22 carbon atoms, and most preferably from 14 to 18 carbon atoms. Among these, N-alkanoyl groups, such as those derived from saturated fatty acids, are preferred. Specific examples of preferred N-alkanoyl groups are N-acetyl, N-myristoyl and N-palmitoyl groups, among which N-palmitoyl groups are most preferred.

In another embodiment, the number of carbon atoms of the (hetero)hydrocarbylcarbonyl groups as the acyl groups is from 2 to 22, preferably from 2 to 16, more preferably from 2 to 10, and even more preferably from 2 to 6 carbon atoms and the hydrocarbylcarbonyl group is unsubstituted or substituted with one substituent selected from the group consisting of a hydroxyl group, an amino group, a thio group, an oxo group, a $C_1$-$C_6$ alkylthio group, preferably a $C_1$-$C_3$ alkylthio group, a $C_1$-$C_6$ alkyloxy group, preferably a $C_1$-$C_3$ alkyloxy group, a $C_1$-$C_3$ alkylamino group and a di($C_1$-$C_3$ alkyl)amino group. In one sub-embodiment, the substituent is an amino group. Such acyl groups may be acyl groups derived from α-amino acids such as the 20 standard amino acids. Specific examples are an acyl groups derived from glycine or N-methylglycine, whereby the acyl-amino-LNA is glycyl-amino-LNA or N-methylglycyl-amino-LNA, respectively.

The acyl groups of multiple acyl-amino-LNA nucleotide units in the oligo of the invention may be the same or different.

The oligo of the invention may be PEGylated e.g. for improving serum half-life of the oligo. Modification of oligonucleotides with poly(ethylene glycol) (PEG) is known in the art and is reviewed by Ikeda and Nagasaki, Journal of Applied Polymer Sciences 2014, 40293. An oligo of the invention may be PEGylated at one or two nucleotide units in the oligo, such as at the 5' one or two nucleotide units, or the 3'-terminal one or two nucleotide units, or at the 5' or 3'-terminal unit. The chemistry of linking PEG to oligonucleotides is known (reviewed e.g. Ikeda and Nagasaki cited above and references cited therein). The PEG may be linear or branched PEG, and may have from 5 to 50000, preferably from 20 to 20000, more preferably from 100 to 10000, and even more preferably from 500 to 5000 —$CH_2CH_2O$— units. If the oligo of the invention contains the acyl-amino-LNA or hydrocarbyl-amino-LNA nucleotide units at one end of the oligo, the PEGylation may be present at the other end of the oligo. In a preferred embodiment, the oligo of the invention is not PEGylated, since the advantageous properties of the oligos of the invention allow achieving sufficient serum half-life for high transfection efficiency even without PEGylation.

Preferred embodiments given above e.g. regarding the base moiety, the amino-LNA moiety and the backbone linkages, and content of acyl-amino-LNA and/or hydrocarbyl-amino-LNA nucleotide monomers in the oligo of the invention may be combined.

The oligos of the invention may be used as antisense oligonucleotides. The oligos of the invention may be gapmers or mixmers. The invention also provides the design and use of gapmer antisense oligonucleotides, mixmer antisense oligonucleotides, antimir oligonucleotides and blockmir oligonucleotides which all have in common that they target RNA.

Gapmers are chimeric antisense oligonucleotides with a central continuous stretch of RNase H recruiting nucleotides flanked by wings containing affinity-enhancing (modified) nucleotides (e.g. LNA, α-L-LNA, BNA, CEt or O2'-alkylated RNA nucleotides). Gapmers may be used for RNase-H mediated antisense RNA targeting and silencing of the latter. The general constitution of a gapmer of this invention is: 5'-Wing-Gap-Wing.

RNase H recruiting nucleotides or nucleotide monomer units, herein also referred to as nucleotides (or nucleotide monomer units) compatible with RNase H degradation, may be DNA nucleotides or FANA nucleotides. The internucleoside linkages may be phosphodiester or phosphorothioate linkages. Preferably, the RNase H recruiting nucleotides are DNA nucleotides with phosphodiester or phosphorothioate linkages, preferably high phosphodiester content as described above, more preferably phosphodiester linkages. In another embodiment, the RNase H recruiting nucleotides are FANA nucleotides with phosphodiester or phosphorothioate linkages. FANA nucleotides mean 2'-deoxy-2'-fluoro-arabino nucleotides [Kalota, A. et al., *Nucleic Acids Res.* 2006, 34, 451-461].

Affinity-enhancing monomers may be LNA, α-L-LNA, BNA, CEt or O2'-alkylated (such as 2'-O—$C_1$-$C_6$-alkyl) RNA nucleotides. The internucleoside linkages are phosphodiester or phosphorothioate linkages, preferably phosphodiester linkages. The acyl-amino-LNA and/or hydrocarbyl (such as alkyl)-amino-LNA monomers of the invention belong to the class of affinity-enhancing monomers. But it cannot be ruled out that certain of the acyl-amino-LNA and/or alkyl-amino-LNA monomers do not by themselves induce affinity-increase against RNA, which however can be modulated by the incorporation of other of the above mentioned affinity-enhancing monomers in the wings of the gapmers, or in general within the oligonucleotide. Thus, affinity-enhancing monomers may be LNA, α-L-LNA, BNA, CEt or 2'O-alkylated RNA nucleotides and/or the acyl-amino-LNA and/or hydrocarbyl (such as alkyl)-amino-LNA monomers of the invention. DNA nucleotide monomers may also be present in a segment of affinity-enhancing monomers, although they are not considered affinity-enhancing herein.

The gapmer may be an oligonucleotide comprising or consisting of, from the 5'-end to the 3'-end, three segments: a 5'-end segment of at least 2 nucleotide units, a central binding segment of at least 6 nucleotide units in length, and a 3'-end segment of at least 2 nucleotide units in length, wherein said oligonucleotide contains at least two 2'-N-acyl-2'-amino-LNA or 2'-N-hydrocarbyl (such as alkyl)-amino-LNA nucleotide monomers in either the 5'-end segment or the 3'-end segment, or contains at least one 2'-N-acyl-2'-amino-LNA or 2'-N-hydrocarbyl (such as alkyl)-amino-LNA nucleotide monomer in each of said end segments, but, in a more specific embodiment, none in the central segment. The oligo may be PEGylated at a nucleotide unit in either the 5'-end segment or the 3'-end segment, such as the end units defined more generally above, however, in one preferred embodiment, the oligo is not PEGylated, neither at a nucleotide unit in the 5'-end segment nor in the 3'-end segment. The 5' and/or 3'-end segments may have at least 3 or at least 4 nucleotide units; and/or the central binding segment may be at least 8 or at least 10 nucleotide units in length. Herein, the term "segment" refers to a plurality of contiguous nucleotide monomer units in an oligonucleotide. When referring to a portion of an oligonucleotide, the term "element" is sometimes used herein in the same meaning.

In another embodiment, the oligonucleotide is a gapmer of the constitution:

$$N_V\text{-}M_Y\text{-}N_Z,$$

wherein M denotes a nucleotide monomer compatible with RNase H degradation of the target RNA, N denotes monomers selected from among affinity-enhancing nucleotide monomers, acyl-amino-LNA and/or hydrocarbyl (such as alkyl)-amino-LNA monomers as defined herein, and/or DNA nucleotide monomers, and wherein V, Y and Z indicate the numbers of the contiguous monomers in the segments. The hyphens indicate the bonds (or mark the separation) between the two wing sequence segments (elements) $N_V$ and $N_Z$ and the gap sequence segment (element) $M_Y$; the numbers V and Z are integers of from 2 to 8, preferably from 2 to 5, and the number Y is an integer of from 6 to 14, preferably of from 8 to 13, provided that the sum of V+Z+Y is from 10 to 30, preferably from 12 to 26. In one embodiment (a), at least one acyl-amino-LNA and/or hydrocarbyl-amino-LNA monomer is present in each of the two wing segments (elements), i.e. the segments composed of the N monomer units. In another embodiment (b), the at least two acyl-amino-LNA and/or hydrocarbyl-amino-LNA monomers are present in one of the wing segments (elements), but none may be present in the other wing segment.

The single stranded oligonucleotide may have the following constitution:

$$F'\text{-}(L)_{2\text{-}4}\text{-}(D)_{6\text{-}10}\text{-}(L)_{2\text{-}4},$$

where D denotes a DNA nucleotide monomer and L denotes an affinity-enhancing nucleotide monomer or an acyl-amino-LNA and/or hydrocarbyl (such as alkyl)-amino-LNA monomer as defined herein, or a DNA monomer, or a 2'-O-alkyl-RNA monomer, or a 2'-O-alkoxyalkyl-RNA monomer. At least one acyl-amino-LNA and/or hydrocarbyl (such as alkyl)-amino-LNA monomer may be present in each of the two wing segments, i.e. the segments composed of the L monomer units. Alternatively, at least two acyl-amino-LNA and/or hydrocarbyl (such as alkyl)-amino-LNA monomer units are present in one of the wing segments; the other wing segment may be devoid of or may have one or more acyl-amino-LNA and/or hydrocarbyl (such as alkyl)-amino-LNA monomer units.

The mixmers of the invention may be chimeric antisense oligonucleotide molecules containing affinity-enhancing modified nucleotides as defined above (e.g. LNA, α-L-LNA, BNA, CEt or O2'-alkylated RNA nucleotides). In addition, they may also contain DNA or RNA nucleotides. With the term mixmer is meant RNA-targeting oligonucleotides not composed as gapmers, i.e. not restricted to the general structure 5'-Wing-Gap-Wing. They thus for example can be composed of alternating DNA and LNA-type nucleotides where at least two of the LNA-type nucleotides are selected among acyl-amino-LNA and/or hydrocarbyl (such as alkyl)-amino-LNA monomers, or they, as another example, can be composed of approximately 60-70% 2'-O-Me-RNA and approximately 30-40% LNA-type nucleotides where at least two of the LNA-type nucleotides are selected among acyl-amino-LNA and/or hydrocarbyl (such as alkyl)-amino-LNA monomers. Modified or substituted RNA such as 2'-O-Me-RNA is not considered herein as (unsubstituted) RNA. The term mixmer when used herein is meant to cover antimir, blockmir, splice-switching, exon-skipping and steric block antisense oligonucleotide.

The invention provides single stranded (mixmer antisense) oligonucleotide having the constitution 5'-(N)$_{7-26}$, preferably 5'-(N)$_{8-26}$, wherein N denotes any nucleotide monomer unit, preferably wherein at least one N may be an affinity-enhancing monomer and other N may be any other type of nucleotide monomer, provided that at least two N nucleotide monomer units are acyl-amino-LNA and/or hydrocarbyl (such as alkyl)-amino-LNA monomers as described above. The sequence of the constitution may be divided into two sequence segments (elements) of equal number of nucleotide units, namely the 5' segment and the 3' segments. In one embodiment (a), each sequence segment (element), i.e. the 5'-segment and the 3'-segment, each contains at least one acyl-amino-LNA and/or hydrocarbyl (such as alkyl)-amino-LNA monomer. In another embodiment (b), at least two acyl-amino-LNA and/or hydrocarbyl (such as alkyl)-amino-LNA monomers are present in one of the two segments (elements), i.e. the 5'-segment or the 3'-segment, but none may be present in the other segment. Therein, the central nucleotide monomer unit is not included in any of the two sequence segments (elements) if the total number of nucleotide units is uneven, i.e. for determining the 5' segment and the 3' segments. This does, however, not exclude the possibility that a central monomer unit may also be an acyl-amino-LNA and/or hydrocarbyl (such as alkyl)-amino-LNA monomer which may be one of the at least two acyl-amino-LNA and/or hydrocarbyl (such as alkyl)-amino-LNA monomers. In one alternative, one acyl-amino-LNA and/or hydrocarbyl (such as alkyl)-amino-LNA monomer is present in one of the half sequence elements and a second acyl-amino-LNA and/or hydrocarbyl (such as alkyl)-amino-LNA monomer is present as the central monomer if the total number of nucleotides is uneven. The monomers of the oligonucleotide are linked by phosphodiester linkages and/or phosphorothioate linkages and/or phosphotriester linkages, with the percentage of phosphodiester linkages described above as preferred also being preferred for mixmer oligonucleotides.

In one embodiment, the single stranded mixmer antisense oligonucleotide has the constitution is 5'-(N)$_{7-12}$, where N denotes affinity enhancing nucleotides and at least two acyl-amino-LNA and/or hydrocarbyl (such as alkyl)-amino-LNA monomers such that each of said sequence segments (elements) contains at least one acyl-amino-LNA and/or hydrocarbyl (such as alkyl)-amino-LNA monomer. In another embodiment, the single stranded mixmer antisense oligonucleotide has the constitution 5'-(N)$_{12-22}$, where N denotes at least four LNA-type affinity-enhancing monomers, a number of DNA or 2'-OMe-RNA monomers and at least two acyl-amino-LNA and/or hydrocarbyl (such as alkyl)-amino-LNA monomers and such that each of said sequence elements contains at least one acyl-amino-LNA and/or hydrocarbyl (such as alkyl)-amino-LNA monomer. In a still further embodiment, the single stranded mixmer antisense oligonucleotide has the constitution 5'-(N)$_{15-22}$, where N denotes at least three LNA-type affinity-enhancing monomers, a number of 2'-OMe-RNA monomers and at least two acyl-amino-LNA and/or hydrocarbyl (such as alkyl)-amino-LNA monomers and such that each of said sequence elements contains at least one acyl-amino-LNA and/or hydrocarbyl (such as alkyl)-amino-LNA monomer.

In another embodiment, the single stranded mixmer antisense oligonucleotide has the constitution 5'-(N)$_{7-12}$, where N constitutes affinity enhancing nucleotides and at least two acyl-amino-LNA and/or hydrocarbyl (such as alkyl)-amino-LNA monomers such that at least two acyl-amino-LNA and/or hydrocarbyl (such as alkyl)-amino-LNA monomers are present in one of the half sequence elements, i.e. the 5'-end half of the sequence or the 3'-end half of the sequence, provided that the central nucleotide monomer is not included in any of the two sequence elements if the total number of nucleotides is uneven. Alternatively, one acyl-amino-LNA and/or hydrocarbyl (such as alkyl)-amino-LNA monomer is present in one of the half sequence elements and a second acyl-amino-LNA and/or hydrocarbyl (such as alkyl)-amino-LNA monomer is present as the central nucleotide monomer if the total number of nucleotides is uneven. In another embodiment, the single stranded mixmer antisense oligonucleotide has the constitution 5'-(N)$_{12-22}$, where N denotes at least four LNA-type affinity-enhancing monomers, a number of DNA or 2'-OMe-RNA monomers and at least two acyl-amino-LNA and/or hydrocarbyl (such as alkyl)-amino-LNA monomers and such that at least two acyl-amino-LNA and/or hydrocarbyl (such as alkyl)-amino-LNA monomers are present in one of the half sequence elements, i.e. the 5'-end half of the sequence or the 3'-end half of the sequence, provided that the central nucleotide monomer is not included in any of the two sequence elements if the total number of nucleotides is uneven, i.e. for determining the 5' segment and the 3' segments. This does, however, not exclude embodiments where a central nucleotide monomer unit is an acyl-amino-LNA and/or hydrocarbyl (such as alkyl)-amino-LNA monomer. In another embodiment, the single stranded mixmer antisense oligonucleotide has the constitution 5'-(N)$_{15-22}$, where N denotes at least three LNA-type affinity-enhancing monomers, a number of 2'-OMe-RNA monomers and at least two acyl-amino-LNA and/or hydrocarbyl (such as alkyl)-amino-LNA monomers and such that at least two acyl-amino-LNA and/or hydrocarbyl (such as alkyl)-amino-LNA monomers are present in one of the half sequence elements, i.e. the 5'-end half of the sequence or the 3'-end half of the sequence, provided that the central nucleotide monomer is not included in any of the two sequence elements if the total number of nucleotides is uneven.

The general structure of the antisense oligonucleotides of the invention is as follows: 5'-(N)$_{7-30}$, meaning that they consist of from 7 to 30 nucleotides. These nucleotides (nucleotide monomers) can be of any nucleotide structure known from the literature provided that at least two are acyl-amino-LNA and/or hydrocarbyl (such as alkyl)-amino-LNA monomers; any of the preferred embodiments described above may be combined with this general structure.

In the sections below, preferred embodiments of the antisense oligonucleotides of the invention are described. In one embodiment of a gapmer antisense oligonucleotide of the invention, at least one of the acyl-amino-LNA and/or hydrocarbyl (such as alkyl)-amino-LNA monomers is positioned in the wing sequence element towards the 5'-end, and at least one of the acyl-amino-LNA and/or hydrocarbyl (such as alkyl)-amino-LNA monomers is positioned in the wing sequence element towards the 3'-end. This mimics the mixmer scenario in which the sequence of the oligo may be considered divided into two sequence segments (elements) of equal number of nucleotide units, namely the 5' segment and the 3' segments, whereby in case of an uneven number, the central nucleotide unit is neglected in the division. By having these constitutions, the effect of the two acyl-amino-LNA and/or hydrocarbyl (such as alkyl)-amino-LNA monomers will supplement each other and thus provide the improved properties such as increased resistance towards nucleolytic degradation, increased biostability, increased biodistribution, increased tissue distribution, increased cell permeation, increased ability to modulate gene expression in vivo, and/or decreased toxicity.

If for example the antisense oligonucleotide contains one palmitoyl-2'-amino-LNA monomer in each sequence segment (element) as described above—sequence element meaning here the two wings of a gapmer or each sequence element of a mixmer (the 5'-end half and the 3'-end half of the sequence), it is included in the invention. Likewise, if for example the antisense oligonucleotide contains one glycyl-amino-LNA monomer in each sequence element as described above, it is also included in the invention. Likewise, if for example the antisense oligonucleotide contains one glycyl-amino-LNA monomer and one palmitoyl-amino-LNA monomer, they may be positioned in two different sequence elements. If for example, the antisense oligonucleotide contains three glycyl-amino-LNA monomers, they may be dispersed in both sequence elements. Similarly, if more than two, e.g. three, four, five or six acyl-amino-LNA and/or hydrocarbyl (such as alkyl)-amino-LNA monomers are included in a gapmer or mixmer antisense oligonucleotide, they may be dispersed in both sequence elements. This means that each sequence element may contain at least one of the acyl-amino-LNA and/or hydrocarbyl (such as alkyl)-amino-LNA monomers.

In one embodiment that may be combined with any one of the embodiments mentioned above, the oligonucleotide of the invention has one or two nucleotide monomers that are linked to a cholesteryl moiety via a linker. A cholesteryl moiety may be linked to a nucleotide via its hydroxy group to a phosphodiester internucleoside linkage, e.g. as described in WO 2014/005596. Alternatively, a cholesteryl moiety may be linked to the 2'-amino group of a further 2'-amino LNA nucleotide unit in the oligonucleotide. Examples of the latter are as follows:

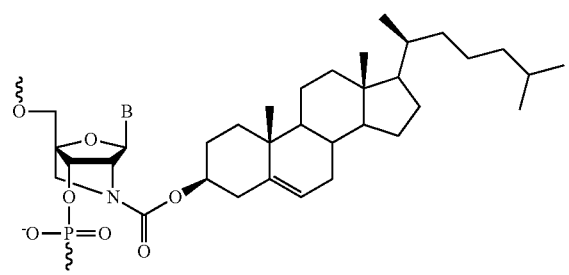

-continued

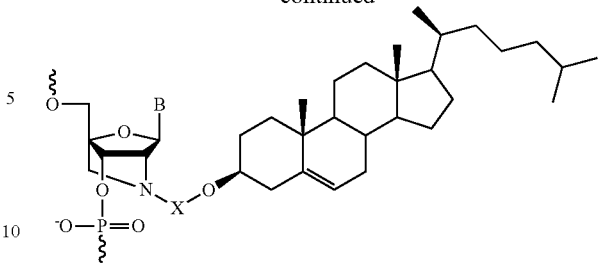

To the left is shown an example where the cholesteryl group is attached to an amino-LNA monomer (here shown as a phosphodiester derivative) via a carbamate linkage. To the right is shown an example where the cholesteryl group is attached to an amino-LNA monomer (here shown as a phosphodiester derivative) via a variable linker X which may be a 1,6-hexanediyl unit or a hexanoyl-6-yl linker (i.e. an N2'-acylated derivative); X alternatively can be shorter or longer linkers of various constitutions, preferably linear alkanediyl or alkanoyl-based linkers that may have from 2 to 20 carbon atoms.

In a generally preferred embodiment A, alternative (i), the gapmer oligo is that of the constitution $N_Y$-$M_Y$-$N_Z$ defined above. In another preferred embodiment B, the constitution of the gapmer antisense oligonucleotides is the following: 5'-LLL-DDDDDDDDD-LLL, where D denotes a DNA nucleotide monomer, L denotes an affinity-enhancing nucleotide monomer or an acyl-amino-LNA and/or alkyl-amino-LNA monomer, and the hyphens indicates separation (bonds) between the two wing sequence elements and the gap sequence element. In another preferred embodiment C, the constitution of the gapmer antisense oligonucleotides is the following: 5'-LL-DDDDDDDD-LL, where D denotes a DNA nucleotide monomer, L denotes an affinity-enhancing nucleotide monomer or an acyl-amino-LNA and/or hydrocarbyl (such as alkyl)-amino-LNA monomer, and the hyphens indicates separation (bonds) between the two wing sequence elements (made up of the L nucleotide units) and the central gap sequence element (made up of the D nucleotide units). In another preferred embodiment D, the constitution of the gapmer antisense oligonucleotides is the following: 5'-LLLL-DDDDDDDD-LLLL, where D denotes a DNA nucleotide monomer, L denotes an affinity-enhancing nucleotide monomer or an acyl-amino-LNA and/or hydrocarbyl (such as alkyl)-amino-LNA monomer, and the hyphens indicates separation (bonds) between the two wing sequence elements and the gap sequence element. In another preferred embodiment E, the constitution of the gapmer antisense oligonucleotide is that of formula 5'-$(L)_{2-4}$-$(D)_{6-10}$-$(L)_{2-4}$ defined above. For clarity, it should be noted that the hyphens indicating separation (bonds) between the two wing sequence elements and the gap sequence element each can be a phosphothioate linkage (between an L and a D monomer), a phosphodiester linkage (between an L and a D monomer) or a phosphortriester linkage (between an L and a D monomer); all of the monomer units of the oligonucleotide may be linked by the same linkages.

In the embodiments of the preceding paragraph (embodiments A-E), one monomer L in each wing segment may, in one sub-embodiment, be an acyl-amino-LNA monomer in which the acyl group is a fatty acid residue (e.g. a palmitoyl group). In another sub-embodiment, one monomer L in each wing is a palmitoyl-amino-LNA monomer containing a pyrimidine nucleobase. In another sub-embodiment, one monomer L in each wing is a myristoyl-amino-LNA monomer containing a pyrimidine nucleobase. In a further sub-embodiment, at least one monomer L is a palmitoyl-amino-LNA monomer containing a pyrimidine nucleobase. In a further sub-embodiment, at least one monomer L is a myristoyl-amino-LNA monomer containing a pyrimidine nucleobase. In a further sub-embodiment, one monomer L in one of the wings is a myristoyl-amino-LNA monomer and another monomer L in the other wing segment is a glycyl-amino-LNA monomer. In a further sub-embodiment, at least one monomer L is a glycyl-amino-LNA monomer containing a pyrimidine nucleobase. In a further sub-embodiment, at least one monomer L is a lysyl-amino-LNA monomer containing a pyrimidine nucleobase.

In a preferred sub-embodiment of the embodiments A-E, two monomers L in one of the wing elements are acyl-amino-LNA monomers in which the acyl group is a fatty acid residue (e.g. a palmitoyl group). In another preferred sub-embodiment of the embodiments A-E, two monomers L in one of the wing elements are palmitoyl-amino-LNA monomers containing a pyrimidine nucleobase. In another preferred sub-embodiment of the embodiments A-E, two monomers L in one of the wing elements are myristoyl-amino-LNA monomers containing a pyrimidine nucleobase.

In a preferred embodiment F, the mixmer antisense oligonucleotide of the invention has the constitution 5'-(N)$_{7-26}$, where N denotes at least one affinity-enhancing monomer and in addition may denote any other type of known nucleotide monomer, provided that at least two N nucleotides are acyl-amino-LNA and/or hydrocarbyl (such as alkyl)-amino-LNA monomers and that each sequence element (see above) contains at least one acyl-amino-LNA and/or hydrocarbyl (such as alkyl)-amino-LNA monomer.

In one preferred embodiment G, the mixmer antisense oligonucleotide has the constitution 5'-(N)$_{7-12}$, where N constitutes affinity enhancing nucleotides and at least two acyl-amino-LNA and/or hydrocarbyl (such as alkyl)-amino-LNA monomers such that each sequence element (see above) contains at least one acyl-amino-LNA and/or hydrocarbyl (such as alkyl)-amino-LNA monomer.

In a preferred embodiment H the mixmer antisense oligonucleotide of the invention has the constitution 5'-(N)$_{12-22}$, where N denotes at least four LNA-type affinity-enhancing monomers, a number of DNA or 2'-OMe-RNA monomers and at least two acyl-amino-LNA and/or hydrocarbyl (such as alkyl)-amino-LNA monomers and such that each sequence element (see above) contains at least one acyl-amino-LNA and/or hydrocarbyl (such as alkyl)-amino-LNA monomer.

In another preferred embodiment I the mixmer antisense oligonucleotide of the invention has the constitution 5'-(N)$_{15-22}$, where N denotes at least three LNA-type affinity-enhancing monomers, a number of 2'-OMe-RNA monomers and at least two acyl-amino-LNA and/or hydrocarbyl (such as alkyl)-amino-LNA monomers and such that each sequence element (see above) contains at least one acyl-amino-LNA and/or hydrocarbyl (such as alkyl)-amino-LNA monomer.

In one preferred sub-embodiment of the embodiments F to I, one monomer N in each sequence element is an acyl-amino-LNA monomer in which the acyl group is a fatty acid residue (e.g. a palmitoyl group).

In another preferred sub-embodiment of the embodiments F to I, one monomer N in each sequence element is a palmitoyl-amino-LNA monomer containing a pyrimidine nucleobase.

In another preferred sub-embodiment of the embodiments F to I, one monomer N in each sequence element is a myristoyl-amino-LNA monomer containing a pyrimidine nucleobase.

In one preferred sub-embodiment of the embodiments F to I, at least one monomer N is an acyl-amino-LNA monomer in which the acyl group is a fatty acid residue (e.g. a palmitoyl group).

In another preferred sub-embodiment of the embodiments F to I, at least one monomer N is a palmitoyl-amino-LNA monomer containing a pyrimidine nucleobase.

In another preferred sub-embodiment of the embodiments F to I, at least one monomer N is a myristoyl-amino-LNA monomer containing a pyrimidine nucleobase.

In another preferred sub-embodiment of the embodiments F to I, one monomer N in each of the sequence elements is a myristoyl-amino-LNA monomer and another monomer N is a glycyl-amino-LNA monomer.

In another preferred sub-embodiment of the embodiments F to I, at least one monomer N is a glycyl-amino-LNA monomer containing a pyrimidine nucleobase.

In another preferred sub-embodiment of the embodiments F to I, at least one monomer N is a lysyl-amino-LNA monomer containing a pyrimidine nucleobase.

In one sub-embodiment of the embodiments A to I, at least one acyl-amino-LNA monomer containing as part of the acyl group an adamantly group is present.

In another sub-embodiment of the embodiments A to I, at least one acetyl-amino-LNA monomer is present.

In a preferred sub-embodiment of the embodiments A to I, one to three amino-LNA monomer(s) are (is) present (i.e. the unfunctionalized 2'-NH-LNA) in order to mediate endosomal escape because of protonation (published pKa value of the protonated N-2' derivative is approximately 6.1.

In a preferred embodiment F', the mixmer antisense oligonucleotide of the invention has the constitution 5'-(N)$_{7-26}$, where N denotes at least one affinity-enhancing monomer and in addition may denote any other type of known nucleotide monomer, provided that at least two N nucleotides are acyl-amino-LNA and/or hydrocarbyl (such as alkyl)-amino-LNA monomers and that one of the sequence elements (see above) contains at least two acyl-amino-LNA and/or hydrocarbyl (such as alkyl)-amino-LNA monomers.

In one preferred embodiment G', the mixmer antisense oligonucleotide has the constitution 5'-(N)$_{7-12}$, where N constitutes affinity enhancing nucleotides and acyl-amino-LNA and/or hydrocarbyl (such as alkyl)-amino-LNA monomers, provided that at least two N nucleotides are acyl-amino-LNA and/or hydrocarbyl (such as alkyl)-amino-LNA monomers and that one of the sequence elements (see above) contains at least two acyl-amino-LNA and/or hydrocarbyl (such as alkyl)-amino-LNA monomers.

In a preferred embodiment H' the mixmer antisense oligonucleotide of the invention has the constitution 5'-(N)$_{12-22}$, where N denotes at least four LNA-type affinity-enhancing monomers, a number of DNA or 2'-OMe-RNA monomers and at least two acyl-amino-LNA and/or hydrocarbyl (such as alkyl)-amino-LNA monomers, provided that one of the sequence elements (see above) contains at least two acyl-amino-LNA and/or hydrocarbyl (such as alkyl)-amino-LNA monomers.

In another preferred embodiment I', the mixmer antisense oligonucleotide of the invention has the constitution 5'-(N)$_{15-22}$, where N denotes at least three LNA-type affinity-enhancing monomers, a number of 2'-OMe-RNA monomers and at least two acyl-amino-LNA and/or hydrocarbyl (such as alkyl)-amino-LNA monomers, provided that one of the sequence elements (see above) contains at least two acyl-amino-LNA and/or hydrocarbyl (such as alkyl)-amino-LNA monomers.

In one preferred sub-embodiment of the embodiments F' to I', two N monomers in one of the sequence elements are acyl-amino-LNA monomers in which the acyl group is a fatty acid residue (e.g. a palmitoyl group).

In another preferred sub-embodiment of the embodiments F' to I', two N monomers in one of the sequence elements are palmitoyl-amino-LNA monomers containing a pyrimidine nucleobase.

In another preferred sub-embodiment of the embodiments F' to I', two N monomers in one of the sequence elements are myristoyl-amino-LNA monomers containing a pyrimidine nucleobase.

In one preferred sub-embodiment of the embodiments F' to I', two N monomers in one of the sequence elements are acyl-amino-LNA monomers in which the acyl group is a fatty acid residue (e.g. a palmitoyl group).

In another preferred sub-embodiment of the embodiments F' to I', two N monomers in one of the sequence elements are palmitoyl-amino-LNA monomers containing a pyrimidine nucleobase.

In another preferred sub-embodiment of the embodiments F' to I', two N monomers in one of the sequence elements are myristoyl-amino-LNA monomers containing a pyrimidine nucleobase.

In another preferred sub-embodiment of the embodiments F' to I', one monomer N is a myristoyl-amino-LNA monomer and another monomer N is a glycyl-amino-LNA monomer.

In a preferred embodiment, all internucleoside linkages are phosphodiester linkages.

In one embodiment, all internucleoside linkages are phosphorothioate linkages.

The invention includes lipid nanoparticle, other nanoparticulate and dendrimer (dentric) formulations, and as well as other nanomaterials of or including the gapmer or mixmer antisense oligonucleotides.

The invention includes as an embodiment conjugates of the antisense oligonucleotides—e.g. antenna-like oligogalactose derivatives.

The invention includes, as a preferred embodiment, 3'-end or 5'-end conjugates of the antisense oligonucleotides with antenna-like mono-, di- or trimeric galactosyl or N-acetylamino galactosyl moieties.

The antisense oligonucleotides of the invention is useful for modulation of gene expression in vitro or in vivo, e.g. to diagnose disease or to treat diseases.

In one preferred embodiment, the antisense oligonucleotides of the invention are able to bind to plasma proteins which increases the retention of the RNA complexes in the human body.

In a preferred embodiment, the antisense oligonucleotides of the invention are conjugated to groups that are known to mediate improved biodistribution, cell-membrane permeability, tissue distribution etc. Examples of such groups that are known to a person skilled in the art are cell penetrating peptides, cholesterol, galactose or alpha-tocopherol moieties.

In another embodiment of the invention, the antisense oligonucleotides produce a reduced immune response relative to the corresponding antisense oligonucleotides without the acyl-amino-LNA and hydrocarbyl (such as alkyl)-amino-LNA monomers.

In another embodiment of the invention, the antisense oligonucleotides display reduced toxicity relative to the corresponding antisense oligonucleotides without the acyl-amino-LNA and hydrocarbyl (such as alkyl)-amino-LNA monomers.

In another embodiment of the invention, the antisense oligonucleotides have a prolonged effect relative to the corresponding antisense oligonucleotides without the acyl-amino-LNA and hydrocarbyl (such as alkyl)-amino-LNA monomers.

In still another embodiment, the antisense oligonucleotides of the invention are transported efficiently to specific organs or tissues of a human or an animal.

In yet still another embodiment, the antisense oligonucleotides of the invention are able to penetrate a cell membrane efficiently.

The antisense and aptamer oligonucleotides of the invention may contain at least two acyl-amino-LNA and/or hydrocarbyl (such as alkyl)-amino-LNA nucleotides in one half segment of its sequence. This design surprisingly collectively leads to very appealing properties, i.e. high binding to human serum albumin which limits renal excretion and leads to improved biodistribution and biological effect. The antisense and aptamer oligonucleotides of the invention may contain at least two acyl-amino-LNA and/or hydrocarbyl (such as alkyl)-amino-LNA nucleotides in one half segment of its sequence, such that two acyl-amino-LNA and/or alkyl-amino-LNA nucleotides are positioned among the penultimate four nucleotides. The antisense and aptamer oligonucleotides of the invention may contain at least two acyl-amino-LNA and/or alkyl-amino-LNA nucleotides in one half segment of its sequence, such that two acyl-amino-LNA and/or hydrocarbyl (such as alkyl)-amino-LNA nucleotides are positioned as the two most exterior (end-positioned) nucleotides.

The present invention discloses how to modify aptamers for improved biodistribution and bioavailability. This is achieved by using oligonucleotides comprising at least two acyl- and/or hydrocarbyl (such as alkyl)-amino-LNA monomer units according to the invention as aptamers. This will lead to improved binding to plasma proteins like human serum albumin and thereby increase the circulation time, i.e. impede rapid clearance and thereby alleviate the need for conjugation with a larger molecular entity like PEG or nanoparticulate formulations.

The present invention provides acyl- and/or hydrocarbyl (such as alkyl)-amino-LNA monomer-containing oligonucleotides as aptamers. These aptamers are for example useful as antiproliferative agents and anticancer drugs or as drug delivery devices. The acyl- and/or hydrocarbyl (such as alkyl)-amino-LNA modified aptamer may also be useful against other diseases.

In one embodiment, all the acyl- and/or hydrocarbyl (such as alkyl)-amino-LNA monomer units of an aptamer of the invention are attached consecutively to one of the ends of the patent aptamer.

In another embodiment, each end of an aptamer of the invention contains at least one acyl- and/or hydrocarbyl (such as alkyl)-amino-LNA monomer.

In yet another embodiment, two or more of the nucleotides included in the parent aptamer have each been substituted by an acyl- or hydrocarbyl (such as alkyl)-amino-LNA monomer.

In other embodiments, combinations of the above three embodiments are generated such that the resulting aptamers contains at least two acyl- and/or hydrocarbyl (such as alkyl)-amino-LNA monomers.

One embodiment comprises aptamers containing in total between two and four acyl- and/or hydrocarbyl (such as alkyl)-amino-LNA nucleotides.

In another embodiment, an aptamer of the invention contains in total two acyl- and/or hydrocarbyl (such as alkyl)-amino-LNA nucleotides.

In a preferred embodiment, an aptamer of the invention contains two palmitoyl-amino-LNA nucleotides.

The aptamers of the invention can be synthesized using standard methods of automated nucleic acid synthesis as also exemplified for other constructs of the invention. In this way various modified and unmodified nucleotides can be mixed with the acyl- and/or hydrocarbyl (such as alkyl)-amino-LNA monomers in order to produce the aptamers of the invention.

The oligonucleotides of the invention are useful for modulation of a biological response that is relevant for disease intervention or treatment in vivo.

The antisense oligonucleotides of the invention may be prepared by automated oligonucleotide synthesis as known to a person skilled in the art. The incorporation of the acyl-amino-LNA and alkyl-amino-LNA monomers of the invention into the oligonucleotides of the invention follows standard methods for oligonucleotide synthesis, work-up, purification and isolation [F. Eckstein, Oligonucleotides and Analogues, IRL Press, Oxford University Press, 1991] with modifications as published [Johannsen, M. W. et al., Org. Biomol. Chem., 2011, 9, 243]. Some acyl-amino-LNA and alkyl-amino-LNA monomers that may be used for making the oligonucleotides of the invention have previously been synthesized, and procedures for preparation of their phosphoramidite building blocks for automated oligonucleotide synthesis have been reported [Johannsen, M. W. et al., Org. Biomol. Chem., 2011, 9, 243] [I. K. Astakhova and J. Wengel, Acc. Chem. Res., 2014, 47, 1768 and references cited therein].

The oligo of the invention may be used in therapy of an animal such as a mammal, and preferably in humans. The therapy may be therapy of cancer. The invention also provides the oligo of the invention for use as a medicament. The invention also provides the oligo of the invention for use in diagnostics such as molecular diagnostics. The invention also provides the oligo of the invention for use in disease prognostics. It will be apparent to the skilled person that the antisense and aptamer oligonucleotides of the invention can be designed to target specific genes and gene products. It is to be understood that the antisense oligonucleotide can be used to target an RNA sequence. However, the level of a gene product such as a protein may be affected indirectly, if its related mRNA or a non-coding RNA is modified e.g. by RNA degradation or translational inhibition. Also the expression of the gene encoding the protein may be affected, e.g. because of DNA methylation.

The antisense and aptamer oligonucleotide of the invention may be used as a medicament. Once a therapeutic target has been validated, the skilled man can design the oligonucleotides that affect the level and the activity of the target, because the specificity of the antisense oligonucleotides lies exclusively within the sequence and composition of the antisense oligonucleotide.

The invention also provides a pharmaceutical composition comprising the antisense oligonucleotide of the invention and a pharmaceutically acceptable excipient such as a diluent, a carrier or an adjuvant.

Pharmaceutical compositions comprising the oligonucleotide of the invention may be administered as known in the art in a physiologically acceptable medium (e.g., deionized water, phosphate buffered saline (PBS), saline, aqueous ethanol or other alcohol, plasma, proteinaceous solutions, mannitol, aqueous glucose, vegetable oil, or the like). Thus a further embodiment of the present invention relates to a pharmaceutical composition comprising the oligonucleotide with suitable excipients. Buffers may also be included, particularly where the media are generally buffered at a pH in the range of about 5 to 10, where the buffer will generally range in concentration from about 50 to 250 mM salt, where the concentration of salt will generally range from about 5 to 500 mM, physiologically acceptable stabilizers, and the like. The oligonucleotide or the compositions may be lyophilized for convenient storage and transport. Thus, in a further embodiment of the present invention the composition comprises one or more excipients, diluents and/or carriers. Aqueous suspensions may contain the active materials in admixture with excipients suitable for the manufacture of aqueous suspensions. Such excipients include suspending agents, for example sodium carboxymethylcellulose, methylcellulose, hydroxypropyl-methylcellulose, sodium alginate, polyvinylpyrrolidone, gum tragacanth and gum acacia; dispersing or wetting agents can be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. Another possible excipient is albumin such as human serum albumin.

The aqueous suspensions can also contain one or more preservatives, for example ethyl or n-propyl p-hydroxybenzoate, one or more coloring agents, one or more flavoring agents, and one or more sweetening agents, such as sucrose or saccharin. However, it is preferred that the pharmaceutical composition does not include preservatives, but is sterile and packed in single-dose units.

Oily suspensions can be formulated by suspending the active ingredients in a vegetable oil, for example arachis oil, olive oil, sesame oil or coconut oil, or in a mineral oil such as liquid paraffin. The oily suspensions can contain a thickening agent, for example beeswax, hard paraffin or cetyl alcohol. Sweetening agents and flavoring agents can be added to provide palatable oral preparations. These compositions can be preserved by the addition of an anti-oxidant such as ascorbic acid.

Dispersible powders and granules suitable for preparation of an aqueous suspension by the addition of water provide the active ingredient (e.g. in lyophilised form) in admixture with a dispersing or wetting agent, suspending agent and one or more preservatives. Suitable dispersing or wetting agents or suspending agents are exemplified by those already mentioned above. Additional excipients, for example sweetening, flavoring and coloring agents, can also be present. Compositions of the invention can also be in the form of oil-in-water emulsions. The oily phase can be a vegetable oil or a mineral oil or mixtures of these.

Suitable emulsifying agents can be naturally-occurring gums, for example gum acacia or gum tragacanth, naturally-occurring phosphatides, for example soy bean, lecithin, and esters or partial esters derived from fatty acids and hexitol, anhydrides, for example, sorbitan monooleate, and condensation products of the said partial esters with ethylene oxide, for example polyoxyethylene sorbitan monooleate. The emulsions can also contain sweetening and flavoring agents. Compounds of the invention can be administered parenterally in a sterile medium.

The oligonucleotide alone or in combination with excipients, depending on the vehicle and concentration used, can either be suspended or dissolved in the vehicle. Advantageously, adjuvants such as local anesthetics, preservatives and buffering agents can be dissolved in the vehicle.

As also known in the art, the oligonucleotide and the pharmaceutical compositions are generally administered parenterally, such as intravascularly (IV), intraarterial (I.A), intramuscularly (I.M), subcutaneously (SC), mucosally, orally or the like. Administration may also be made by transfusion, or it may be mucosal, oral, nasal, rectal, transdermal or aerosol, where the nature of the conjugate allows for transfer to the vascular system. Usually a single injection will be employed, although more than one injection may be used, if desired. Administration may by any convenient means, including syringe, trocar, catheter, or the like. The particular manner of administration will vary depending upon the concentration to be administered, whether a single bolus or continuous administration, or the like. The administration can be intravascularly, where the site of introduction is not critical to this invention, preferably at a site where there is rapid blood flow, (e.g., intravenously, peripheral or central vein). Preferably, the route of administration is mucosal or oral. Other administration routes may be useful, e.g. where the administration is coupled with slow release techniques or a protective matrix.

Dosage levels of the oligonucleotide as active ingredient are on the order of from about 0.1 mg to about 140 mg per kilogram of body weight per day are useful in the treatment of the described conditions (about 0.5 mg to about 7 g per patient per day). The amount of active ingredient that can be combined with the carrier materials to produce a single dosage form may vary depending upon the host treated and the particular mode of administration. The concentration of the oligonucleotide for administration may range from about 1 pg/ml to 100 mg/ml, pre-administration. The total amount administered intravascularly will generally be in the range of about 0.1 mg to about 500 mg, preferably about 1 mg to about 250 mg.

The composition of the present invention may be formulated for the intended use. Thus, one embodiment of the present invention relates to a composition that is formulated for oral or mucosal administration.

Medical Use and Treatment

The oligonucleotide or the pharmaceutical compositions may be used to treat diseases in a mammal in which inhibition of gene expression of a particular gene is beneficial. "Mammal" for purposes of treatment refers to any animal classified as a mammal, including humans, domestic and farm animals, and zoo, or sports, animals, such as dogs, horses, cats, cows, etc. Preferably, the mammal is human. The diseases that may be treated are diseases that can be treated by down-regulating or silencing a gene or its product, such as those given in WO 2014/005596. Such diseases include, but are not limited to, cancer, autoimmune diseases, viral and bacterial infections, endocrine system disorders, neural disorders including central and peripheral nervous system disorders, cardiovascular disorders, pulmonary disorders, and reproductive system disorders.

In one embodiment of the invention, the oligonucleotide and compositions of the invention are useful for the amelioration and/or treatment of cancers and other hyperproliferative disorders. Cancer cells are usually characterized by aberrant expression of a gene. Cancers and other hyperproliferative disorders for which this invention provides therapy include, but are not limited to, neoplasms associated with connective and musculoskeletal system tissues, such as fibrosarcoma, rhabdomyosarcoma, myxosarcoma, chondrosarcoma, osteogenic sarcoma, chordoma, and liposarcoma, neoplasms located in the abdomen, bone, brain, breast, colon, digestive system, endocrine glands (adrenal, parathyroid, pituitary, testicles, ovary, thymus, thyroid), eye, head and neck, liver, lymphatic system, nervous system (central and peripheral), pancreas, pelvis, peritoneum, skin, soft tissue, spleen, thorax, and urogenital tract, leukemias (including acute promyelocytic, acute lymphocytic leukemia, acute myelocytic leukemia, myeloblasts, promyelocytic, myelomonocytic, monocytic, erythroleukemia), lymphomas (including Hodgkins and non-Hodgkins lymphomas), multiple myeloma, colon carcinoma, prostate cancer, lung cancer, small cell lung carcinoma, bronchogenic carcinoma, testicular cancer, cervical cancer, ovarian cancer, breast cancer, angiosarcoma, lymphangiosarcoma, endotheliosarcoma, lymphangioendotheliosarcoma, synovioma, mesothelioma, Ewing's sarcoma, leiomyosarcoma, squamous cell carcinoma, basal cell carcinoma, pancreatic cancer, renal cell carcinoma, Wilm's tumor, hepatoma, bile duct carcinoma, adenocarcinoma, epithelial carcinoma, melanoma, sweat gland carcinoma, sebaceous gland carcinoma, papillary carcinoma, papillary adenocarcinoma, glioma, astrocytoma, medulloblastoma, craniopharyngioma, ependymoma, pinealoma, emangioblastoma, acoustic neuroma, oligodendroglioma, menangioma, neuroblastoma, retinoblastoma, bladder carcinoma, embryonal carcinoma, cystadenocarcinoma, medullary carcinoma, choriocarcinoma, and seminoma.

Thus an aspect of the present invention relates to the use of oligonucleotide as descried herein for treatment of diseases that benefit from intestinal delivery e.g. cancer, inflammatory disease as described above.

Another aspect of the present invention relates to the use of oligonucleotide as descried herein for intestinal delivery of a drug. Yet another application of the present invention relates to regulating genetic expression of a transcript or protein associated with a disease. A further application of the present invention relates to a method of treating a disease, comprising administration of the oligonucleotide or the composition of the present invention to a mammal in need thereof.

The invention further provides a method of mediating nucleic acid modification of a target nucleic acid in a cell or an organism comprising the steps:

a. contacting a cell or organism with an antisense oligonucleotide of the invention under conditions wherein modification of a target nucleic acid can occur; and b. thereby mediating modification of a target nucleic acid.

The method of mediating nucleic acid modification of a target nucleic acid may be performed in vitro or in vivo, i.e. in animals such as mammals, or in humans. The method of mediating nucleic acid modification of a target nucleic acid may, alternatively, be performed in cell cultures or on an isolated cell. In a preferred embodiment, the nucleic acid modification of the method is gene silencing (=down regulation of gene expression), preferably degradation of target mRNA or translational inhibition of target mRNA or inhibition of other types of RNA, e.g. non-coding RNA. Accordingly, the invention provides a method of mediating gene silencing in a cell or an organism, comprising contacting said cell or organism with an antisense oligonucleotide of the invention. In another embodiment, the invention provides a method of modulating splicing events in a cell or an organism like a human to provide gene products that are able to alleviate diseases which have malfunctioning RNA-splicing as a cause.

Another aspect of the invention is a method of examining the function of a gene in a cell or organism, comprising:
a. introducing an antisense oligonucleotide of the invention corresponding to said gene into the cell or organism, thereby producing a test cell or test organism
b. maintaining the test cell or test organism under conditions under which modification of a target nucleic acid can occur; and
c. observing the phenotype of the test cell or organism produced in step b and optionally comparing the observed phenotype with the phenotype of an appropriate control cell or control organism, thereby providing information about the function of the gene.

The cell is preferably a cell of an animal such as a mammalian or human cell. In preferred embodiments of the method of examining the function of a gene in a cell or organism, the method is performed in cell cultures, in vitro or in vivo. In yet another embodiment, the method is performed on an isolated cell.

The antisense oligonucleotides of the invention can be introduced into cells e.g. using transfection or gymnotic delivery, as known to a person skilled in the art. The oligonucleotides may be introduced into an organism e.g. by intravenous or subcutaneous injection, which is known to the skilled person, or by other methods of introduction known to the skilled person.

The information obtained about the function of a gene may be used to determine whether a gene product is a suitable target for therapeutic intervention in relation to a particular disease. Thus, if it is demonstrated that a certain gene product acts in a certain biochemical pathway known to be affected in e.g. a specific subtype of cancer, the gene product might be a suitable target for therapeutic intervention for treatment of the aforementioned subtype of cancer.

In a preferred embodiment of the method of examining the function of a gene in a cell or organism, the nucleic acid modifications of the method is gene silencing (=down regulation of gene expression), preferably degradation of target mRNA or translational inhibition of target RNA.

Another aspect of the invention is a method of assessing whether an agent acts on a gene product comprising the steps:
a. introducing an antisense oligonucleotide of the invention corresponding to said gene into a cell or organism, thereby producing a test cell or test organism;
b. maintaining the test cell or test organism under conditions under which modification of a target nucleic acid occurs;
c. introducing the agent into the test cell or test organism; and
d. observing the phenotype of the test cell or organism produced in step c and optionally comparing the observed phenotype with the phenotype of an appropriate control cell or control organism, thereby providing information about whether the agent acts on the gene product.

In a preferred embodiment of the method of assessing whether an agent acts on a gene or gene product, the nucleic acid modification of the method is gene silencing (=down regulation of gene expression), preferably degradation of target RNA or translational inhibition of target RNA. In preferred embodiments of the method of assessing whether an agent acts on a gene product, the method is performed in cell cultures, in vitro or in vivo. In yet another embodiment, the method is performed on an isolated cell.

Oligonucleotides of the invention are also useful for research purposes. It is for example well-known how oligonucleotides, including chemically modified oligonucleotides, can be used to study the function of a gene. This involves the addition of the oligonucleotide to a cell culture under conditions where cell membrane penetration is possible. By designing the sequence to be complementary to the target gene, or the target nucleic acid, the effect of such RNA/nucleic acid targeting can be evaluated. This enables for example the evaluation of the importance and effect of expression of that given gene. This research therefore can be important to evaluate the relevance of expression of a given gene, e.g. the protein encoded by such gene, for the development of a given disease. Thus, the invention also provides a reagent containing an oligonucleotide according to the invention. The reagent may further contain an excipient such as any one or more of those mentioned above.

EXAMPLES

Example 1. Synthesis of Acyl-Amino-LNA and Hydrocarbyl-Amino-LNA Monomers

Some acyl-amino-LNA and hydrocarbyl-amino-LNA monomers of the invention have previously been synthesized and procedures for preparation of their phosphoramidite building blocks for automated oligonucleotide synthesis have been reported [Madsen, A. S. et al., J. Org. Chem. 2012, 77, 10718][Johannsen, M. W. et al., Org. Biomol. Chem., 2011, 9, 243] [I. K. Astakhova and J. Wengel, Acc. Chem. Res., 2014, 47, 1768 and references cited therein]. These methods will be well known to a person skilled in the art and can be used for synthesis of phosphoramidite building blocks of other acyl-amino-LNA and hydrocarbyl-amino-LNA monomers.

Example 2. Synthesis of Oligonucleotides of the Invention

The oligonucleotides of the invention are prepared by automated oligonucleotide synthesis as known to a person skilled in the art. The incorporation of the acyl-amino-LNA and hydrocarbyl (such as alkyl)-amino-LNA monomers of the invention into the oligonucleotides of the invention follows standard methods for oligonucleotide synthesis, work-up, purification and isolation [F. Eckstein, Oligonucleotides and Analogues, IRL Press, Oxford University Press, 1991] with minor modifications as published [Johannsen, M. W. et al., Org. Biomol. Chem., 2011, 9, 243] [I. K. Astakhova and J. Wengel, Acc. Chem. Res., 2014, 47, 1768 and references cited therein].

The structure of the acyl-amino-LNA and hydrocarbyl (such as alkyl)-amino-LNA of the invention is exemplified below ($^{Me}C$ stands for 5-methylcytosin-1-yl):

Structure of an LNA nucleotide monomer for comparison:

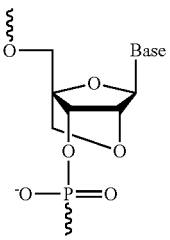

Structure of a pyrimidine acetyl-amino-LNA monomer:

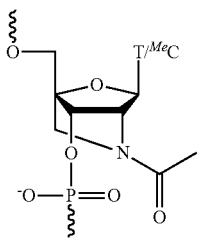

Structure of a pyrimidine palmitoyl-amino-LNA monomer:

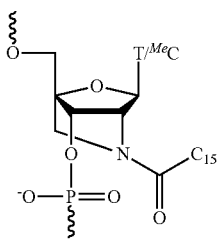

Structure of a pyrimidine glycyl-amino-LNA monomer [note: the amino group of the acyl substituent will be protonated at physiological pH]:

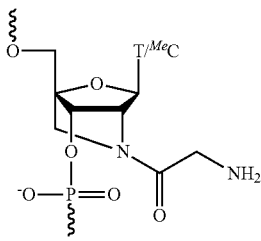

Example 3. Antisense Activity of a Gapmer Antisense Oligonucleotide

In a comparative study in cell culture with unassisted delivery, i.e. with no transfection agent added, the following antisense oligonucleotide was the best among a series of gapmer antisense oligonucleotides of which the majority were of the standard LNA-DNA-LNA (3-9-3) type:

SEQ ID NO: 27:
5'-IG X X-dC dT dC dG dA dG dC dG dT-X X IC
[all PS internucleoside linkages], wherein IG and IC are LNA nucleotides, dC, dA, dG and dT are DNA nucleotides, and X stands for a pyrimidine glycyl-amino-LNA monomer (see structure above).

Also efficient in a similar study was, as examples, sequences of the following constitution:

SEQ ID NO: 28:
5'-IG P L-dC dT dC dG dA dG dC dG dT-L P IC
[all PS internucleoside linkages], SEQ ID NO: 29:
5'-IG P X-dC dT dC dG dA dG dC dG dT-X P IC
[all PS internucleoside linkages], wherein P is the thymine palmitoyl-amino-LNA monomer (see structure above), dC, dA, dG and dT are DNA nucleotides, IT and IG are LNA nucleotides, L is a pyrimidine LNA monomer, and X a glycyl-amino-LNA monomer (see structure above).

Based on this experiment it is concluded:

a) that the antisense constructs of this invention are effective in silencing (i.e. down-regulating") a target gene under unassisted delivery conditions ("gymnotic delivery"), and b) that the amino-LNA monomers of the oligonucleotide constructs of this invention can be positioned simultaneously in both "wings" of an LNA(amino-LNA)-DNA-LNA(amino-LNA) gapmer antisense oligonucleotide, with palmitoyl-amino-LNA monomers in each of the two wings, and that such constructs are biologically active.

Example 4. Albumin Binding of a Gapmer Antisense Oligonucleotide of the Invention A schematic overview of antisense oligonucleotides (ODNs) evaluated for albumin binding is given in FIG. 1. The following table summarises the number of palmitoylated amino-LNA monomers and whether the ONNs have phosphorothioate ("+") internucleoside linkages. Absence thereof ("−") means that the internucleoside linkages are phosphodiester linkages.

| palmitoylated LNAs | phosphorothioate linkages | ODN Designation |
|---|---|---|
| 0 | − | ON7451 |
| 1 | − | ON7452 |
| 2 | − | ON7453 |
| 0 | + | ON7454 |
| 1 | + | ON7455 |
| 2 | + | ON7456 |

The sequences of the six oligonucleotides are shown below:

| | | |
|---|---|---|
| ON7451 | 5'-TAGcctgtcacttCTC (all-PO) | SEQ ID NO: 1 |
| ON7452 | 5'-PAGcctgtcacttCTC (all-PO) | SEQ ID NO: 2 |
| ON7453 | 5'-PAGcctgtcacttP*TC (all-PO) | SEQ ID NO: 3 |
| ON7454 | 5'-TAGcctgtcacttCTC (all-PS) | SEQ ID NO: 4 |

-continued

```
ON7455      5'-PAGcctgtcacttCTC (all-PS)        SEQ ID NO: 5

ON7456      5'-PAGcctgtcacttP*T (all-PS)        SEQ ID NO: 6
```
P and P* denote palmitoyl-amino-LNA thymine and palmitoyl-amino-LNA 5-methyl-cytosine monomers, respectively. A, C, G and T denote LNA monomers, and a, c, g and t denote DNA monomers.

Figures 1, 2:
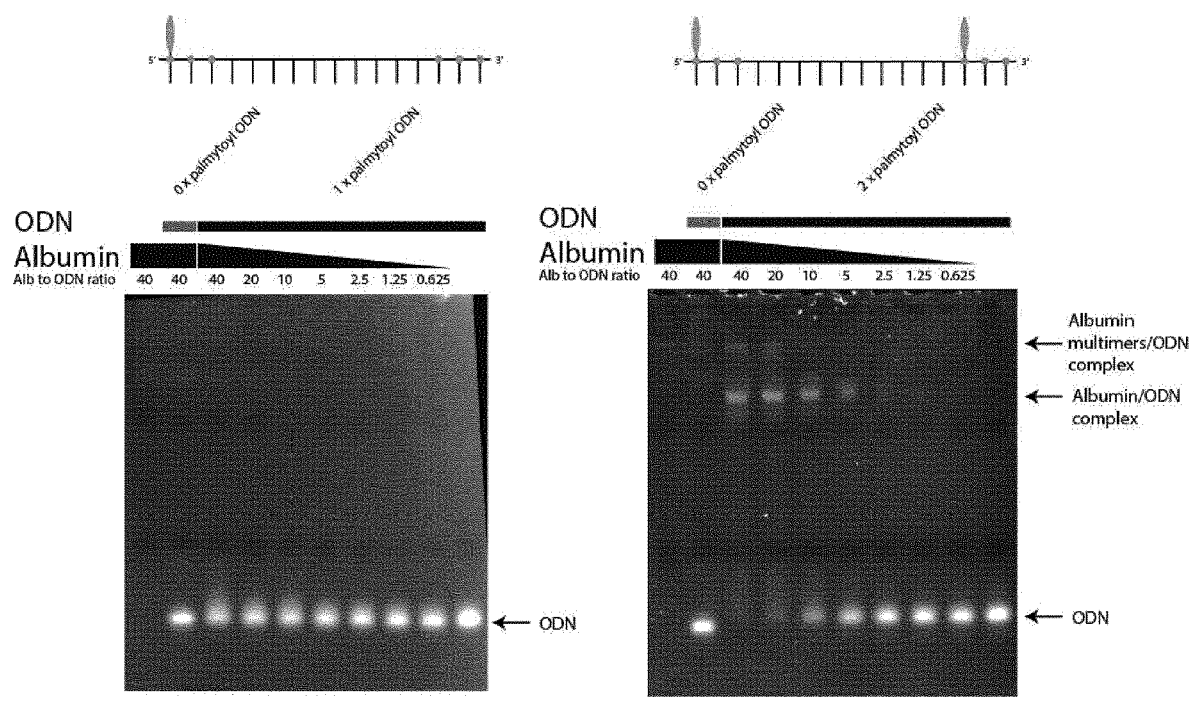
FIG. 2, part 2-1. PAGE of annealing of albumin/ODN complexes, using ODN with one (ON7452; left) and two (ODN7453; right) palmitoly-amino-LNA modifications or no palmitoly-amino-LNA modifications as control (ON7451) and visualized by SYBR gold staining, cf. Example 4. ODNs are here with phosphodiester internucleoside linkages. The upper arrows show where albumin runs in the gel; the visible bands originate from the stained ODN (bound to albumin), whereas the lower stained band is the unbound ODN. The uppermost band (albumin multimers) is thought to be association of ODN with more than one albumin (again visualized via the stained ODN).
Figure 2:
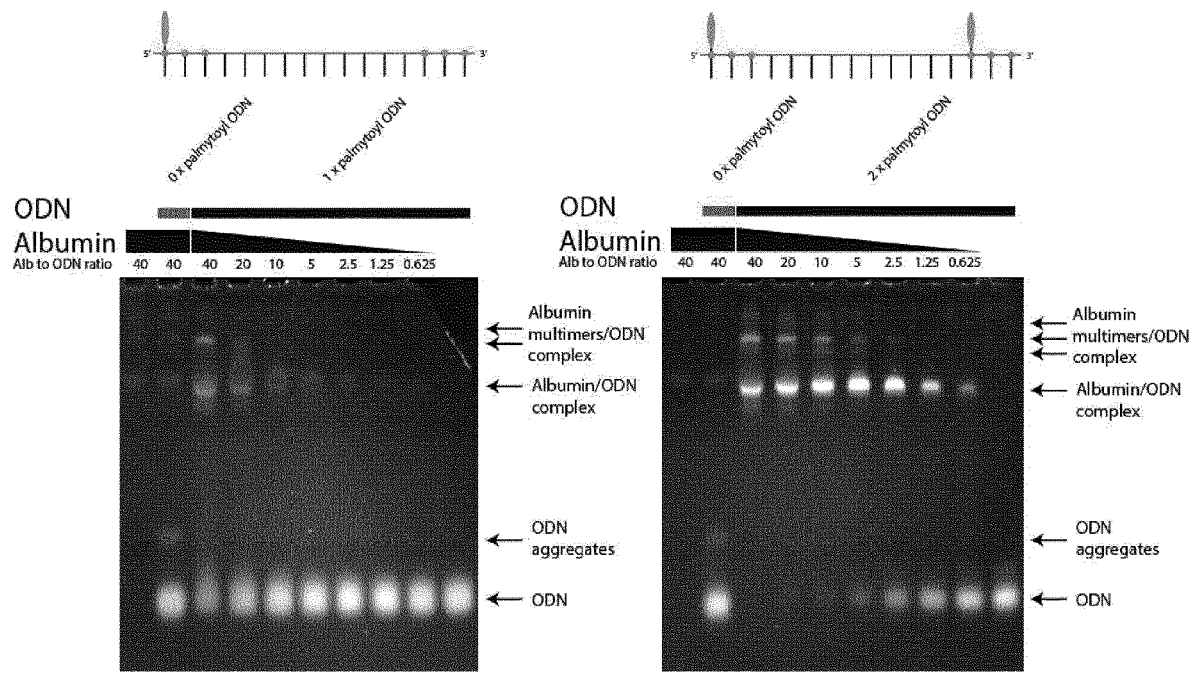
Figures 2, 3:
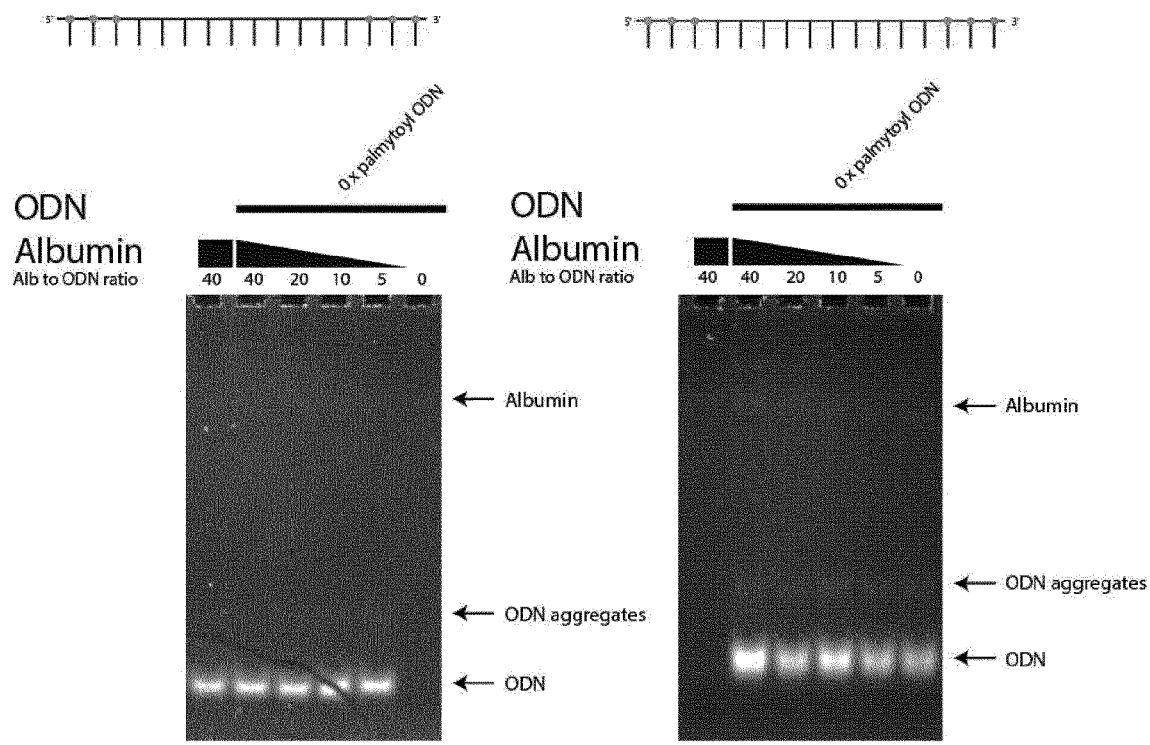
FIG. 3. Graphic representation of modified ODNs, with reference numbers, used in Example 5.
Figure 3:
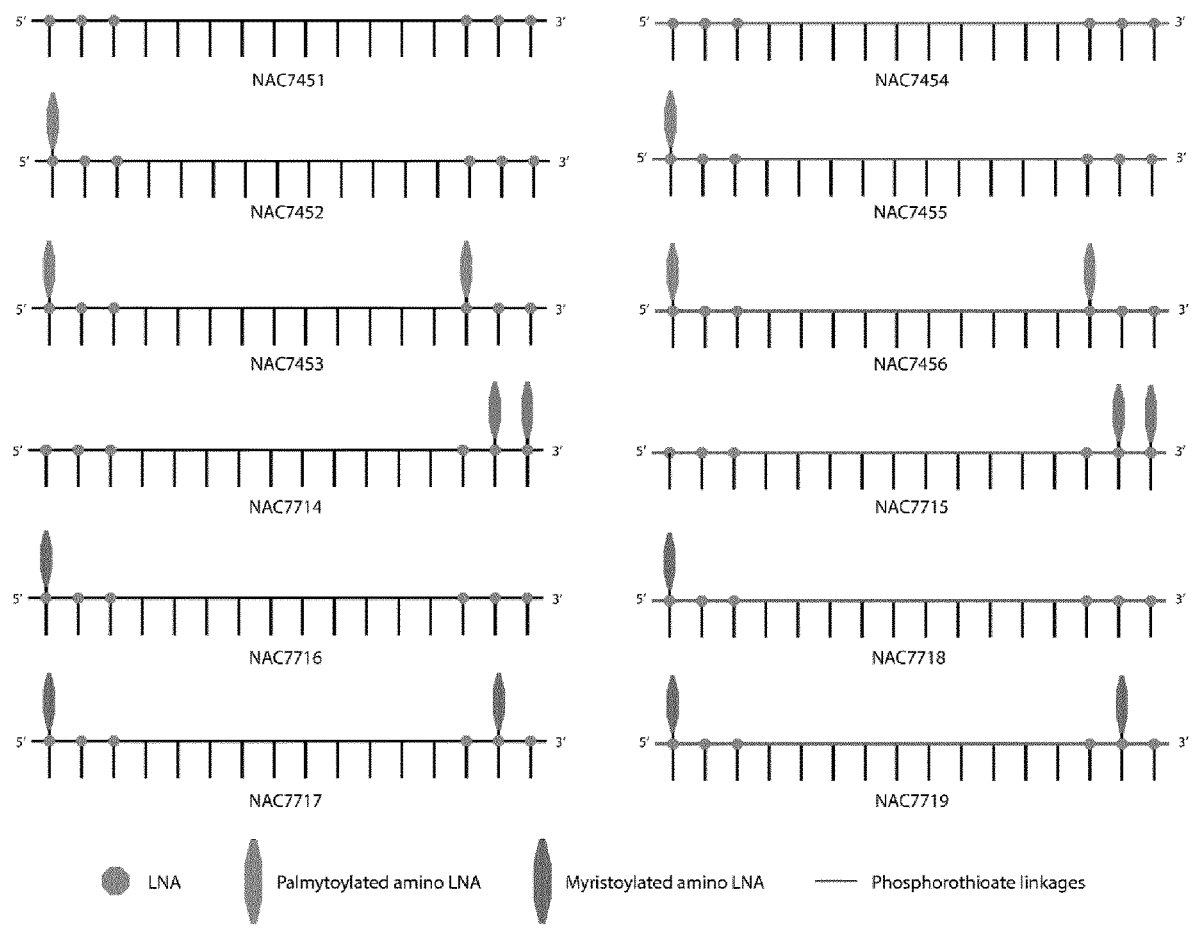
Figure 4:
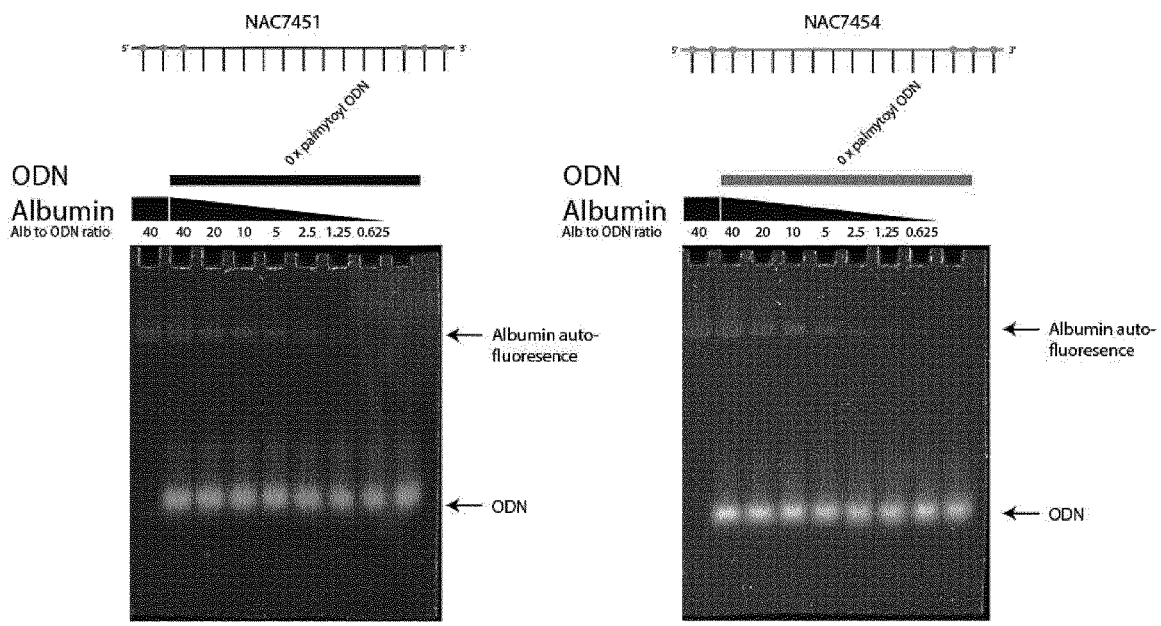
FIG. 4. PAGE of annealing of albumin/ODN complexes by titration of albumin to ODN ratios of Example 5. Results for PO-ODNs (NAC7451) on the left and results for PS-ODNs (NAC7454) on the right.
Figure 5:
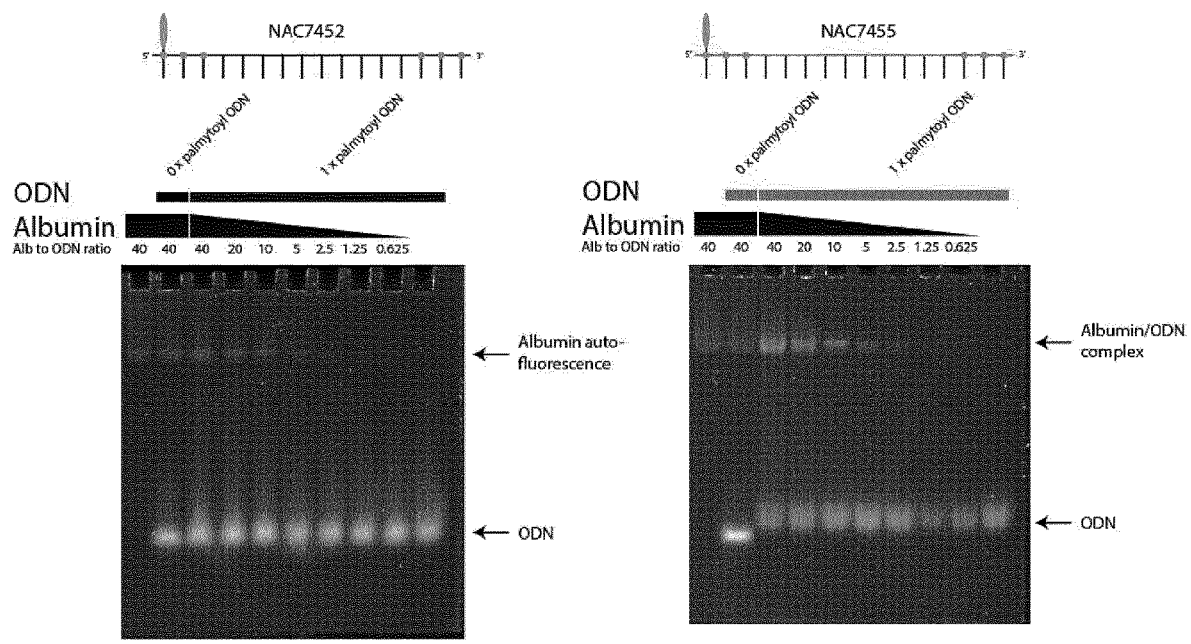
FIG. 5. PAGE of annealing of albumin/ODN complexes by titration of albumin to ODN ratios of Example 5. Results for PO-ODNs (NAC7452) on the left and results for PS-ODNs (NAC7455) on the right.
Figure 6:
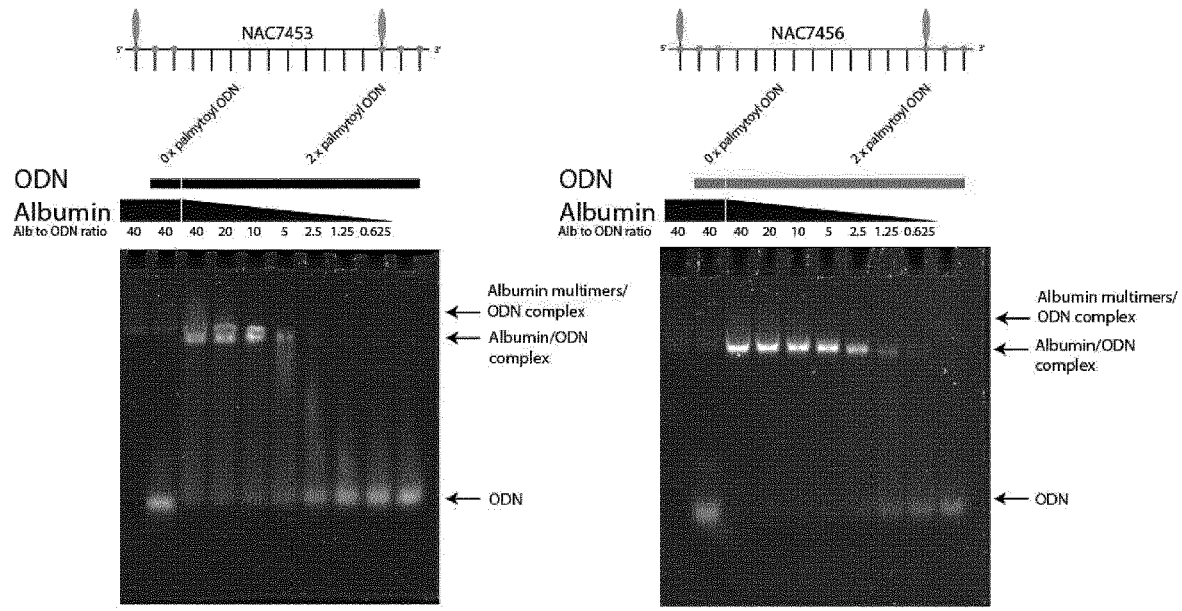
FIG. 6. PAGE of annealing of albumin/ODN complexes by titration of albumin to ODN ratios of Example 5. Results for PO-ODNs (NAC7453) on the left and results for PS-ODNs (NAC7456) on the right.
Figure 7:
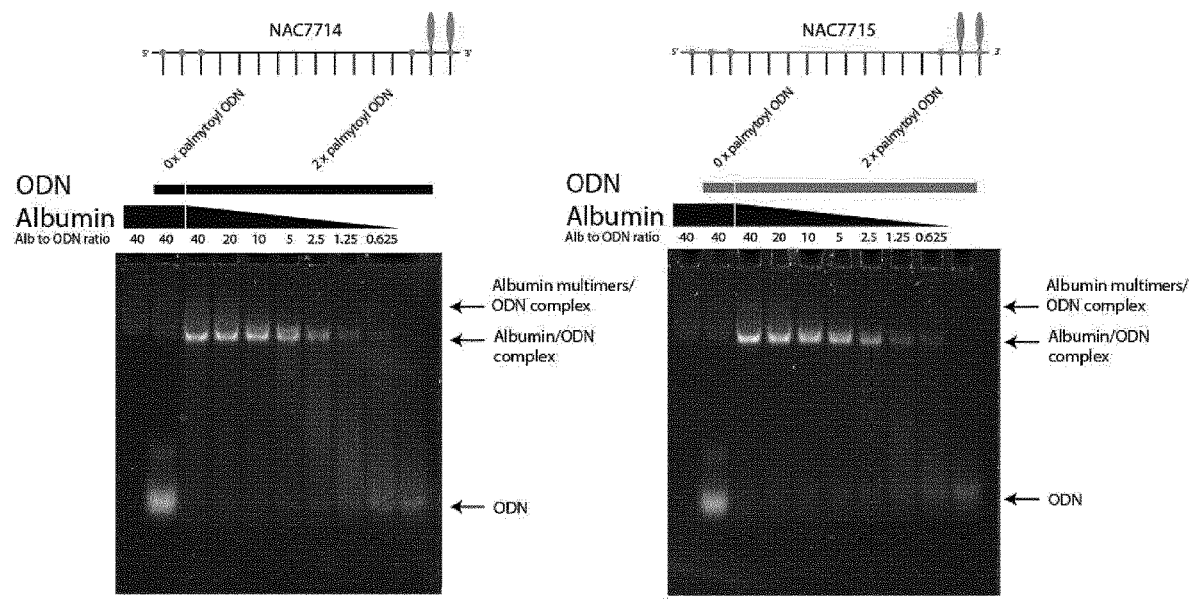
FIG. 7. PAGE of annealing of albumin/ODN complexes by titration of albumin to ODN ratios of Example 5. Results for PO-ODNs (NAC7714) on the left and results for PS-ODNs (NAC7715) on the right.
Figure 8:
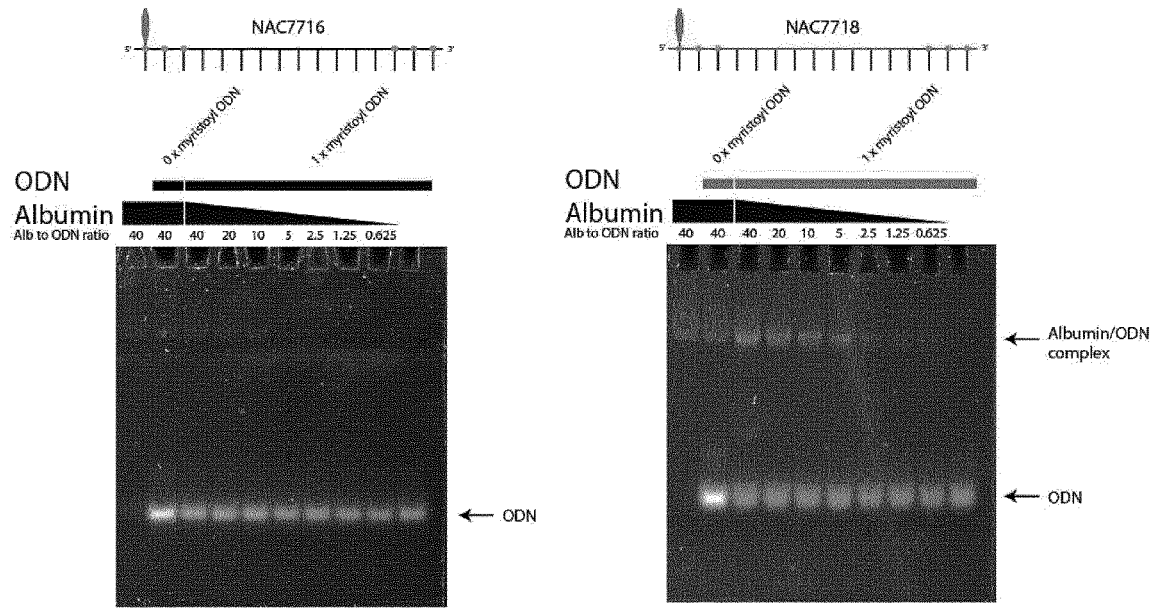
FIG. 8. PAGE of annealing of albumin/ODN complexes by titration of albumin to ODN ratios of Example 5. Results for PO-ODNs (NAC7716) on the left and results for PS-ODNs (NAC7718) on the right.
Figure 9:
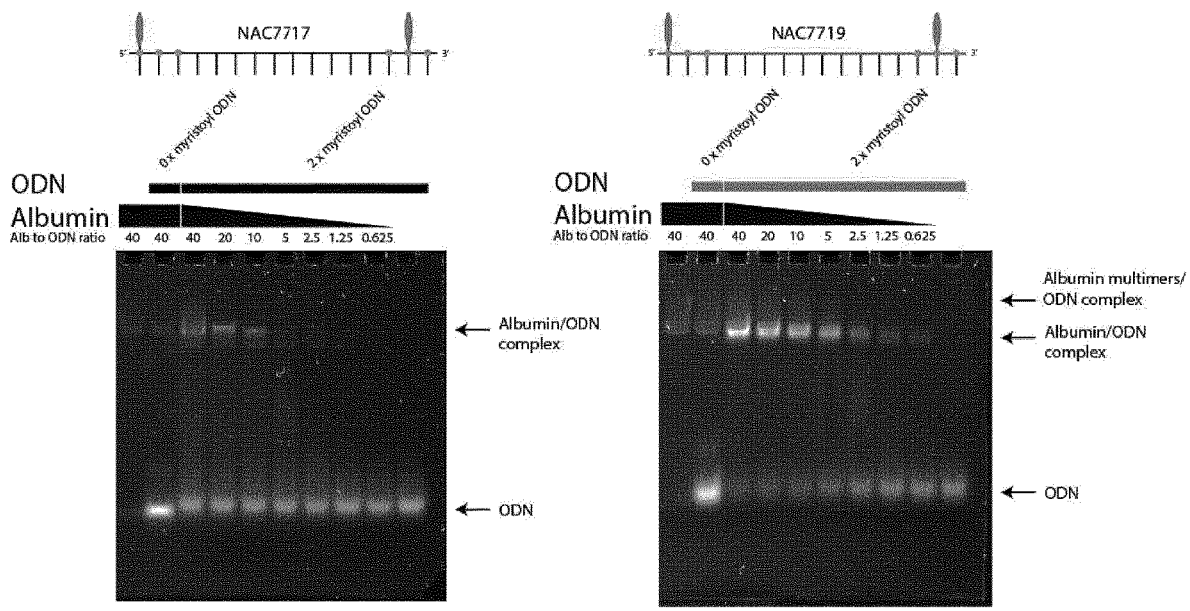
FIG. 9. PAGE of annealing of albumin/ODN complexes by titration of albumin to ODN ratios of Example 5. Results for PO-ODNs (NAC7717) on the left and results for PS-ODNs (NAC7719) on the right.

The albumin to ODN ratio was titrated to visualize binding of fatty acid-conjugated-amino-LNA-modified ODNs (here as example palmitoly-amino-LNA-modified ODNs) to albumin. This was carried out for all six ODNs (FIG. 2-1, FIG. 2-2 and FIG. 2-3). Gel experiments were carried out using the XCell SureLock™ Mine-Cell Electrophoresis System, using Novex™ 8% polyacrylamide gels 1×TBE buffer, 12 wells (Invitrogen, Carlsbad, Calif.), or in non-commercial chambers using ProtoGel 30% (National Diagnostics, Somerville, N.J.). Samples were loaded using Novex™ TBE Running Buffer (5×) (Invitrogen). Gels were run in 1×TBE buffer (From 10× stock, Gibco, Live Technologies, Carlsbad, Calif.). Staining for ODNs was done using SYBR-Gold nucleic acid stain (Invitrogen) following standard protocol.

The two gels in FIG. 2-1 show complex formation with one (ON7452; to the left) or two (ON7453; to the right) palmitoly-amino-LNA modifications in the ODNs—which notably contain phosphodiester internucleoside linkages—after 4 hours of incubation with albumin. We observe no clear interaction between the ODN with one palmitoyl-amino-LNA modification and albumin, not even at a 40:1 albumin:ODN ratio. On the contrary, the ODN (ON7453) with two palmitoly-amino-LNA modifications binds albumin even at low albumin:ODN ratios, and at a 40:1 albumin:ODN ratio no free ODN is observed (FIG. 2-1, right). The control ODN (ON7451) with no palmitoly-amino-LNA modification showed no binding to albumin at a 40:1 albumin:ODN ratio (lanes to the left in the two gels in FIG. 2-1).

A similar experiment was performed with the ODNs having phosphorothioate linkages (FIG. 2-2). For the ODN (ON7454) without palmitoyl-amino-LNA modification (40:1 albumin:ODN ratio), a small band appears where albumin is located, but as the same band appears for albumin alone it most likely emerges because of unspecific binding of SYBR gold to albumin (lanes to the left in the two gels in FIG. 2-2). A small band just above the main ODN band is also observed with however is not associated with albumin and most likely reflects the presence of ODN aggregates. For the ODN (ON7455) with one palmitoyl-amino-LNA modification some interaction with albumin was observed, though a high surplus of albumin (40:1) was needed to have a significant amount of the ODN bound to albumin (FIG. 2-2, left). The ODN (ON7456) with two palmitoyl-amino-LNA modifications starts binding albumin already at the smallest albumin:ODN ratio (0.625:1), and already at an albumin:ODN ratio of 10:1 almost all of the ODN is bound to albumin (FIG. 2-2, right).

To further underline the importance of the fatty acid units for albumin binding, a study with the two ODNs without palmitoyl-amino-LNA modification was undertaken (FIG. 2-3). As can be seen below, no significant binding to albumin was observed neither for the ODN with phosphodiester linkages (ON7451) nor for the ODN with phosphorothioate linkages (ON7454).

Based on these results, we conclude the following:
(a) ODNs with two fatty acid amino-LNA units attached show high binding to albumin.
(b) ODNs with two palmitoyl-amino-LNA modifications show high binding to albumin.
(c) ODNs with two palmitoyl-amino-LNA modifications—one in each end of an LNA-DNA-LNA gapmer antisense oligonucleotide show high binding to albumin.
(d) ODNs with two palmitoyl-amino-LNA modifications—one in each end of an LNA/DNA or LNA/2'-OMe-RNA mixmer antisense oligonucleotide show high binding to albumin.
(e) ODNs containing phosphodiester linkages and no phosphorothioate linkages, but with two palmitoyl-amino-LNA modifications, show high binding to albumin.

Phosphorothioate linkages may increase the binding of palmitoyl-amino-NA modified ODNs to albumin.

The fatty acid residue(s) seem(s) to be a key component for efficient binding of ODNs to albumin.

Example 5. Albumin Binding of a Gapmer Antisense Oligonucleotide

The background for this example is the following general knowledge:
albumin has great potential as drug carrier
antisense oligonucleotides (ODNs) in their phosphorothioate form may bind to albumin and other serum proteins which prevents their rapid excretion via the kidney
fatty acid residues may bind to albumin and modified/engineered albumin derivatives and variants.

A schematic overview of antisense oligonucleotides (ODNs) evaluated for albumin binding is shown in FIG. 3 and listed in the following table.

| modified LNAs | phosphorothioate linkages | Ribotask reference |
| --- | --- | --- |
| — | − | NAC7451 |
| 1 x palmitoyl | − | NAC7452 |
| 2 x palmitoyl | − | NAC7453 |
| — | + | NAC7454 |
| 1 x palmitoyl | + | NAC7455 |
| 2 x palmitoyl | + | NAC7456 |
| 2 x palmitoyl (3') | − | NAC7714 |
| 2 x palmitoyl (3') | + | NAC7715 |
| 1 x myristoyl | − | NAC7716 |
| 2 x myristoyl | − | NAC7717 |
| 1 x myristoyl | + | NAC7718 |
| 2 x myristoyl | + | NAC7719 |

The ODNs listed above have the following sequences.

```
NAC7451     5'-TAGcctgtcacttCTC (all-PO)        SEQ ID NO: 1

NAC7452     5'-PAGcctgtcacttCTC (all-PO)        SEQ ID NO: 2
```

```
NAC7453    5'-PAGcctgtcacttP*TC (all-PO)      SEQ ID NO: 3

NAC7454    5'-TAGcctgtcacttCTC (all-PS)       SEQ ID NO: 4

NAC7455    5'-PAGcctgtcacttCTC (all-PS)       SEQ ID NO: 5

NAC7456    5'-PAGcctgtcacttP*TC (all-PS)      SEQ ID NO: 6

NAC7714    5'-TAGcctgtcacttCPP* (all-PO)      SEQ ID NO: 7

NAC7715    5'-TAGcctgtcacttCPP* (all-PS)      SEQ ID NO: 8

NAC7716    5'-MAGcctgtcacttCTC (all-PO)       SEQ ID NO: 9

NAC7717    5'-MAGcctgtcacttM*TC (all-PO)      SEQ ID NO: 10

NAC7718    5'-MAGcctgtcacttCTC (all-PS)       SEQ ID NO: 11

NAC7719    5'-MAGcctgtcacttM*TC (all-PS)      SEQ ID NO: 12
```
P and M denote palmitoyl-amino-LNA and myristoyl-amino-LNA thymine monomers, respectively,
P* and M* denote palmitoyl-amino-LNA and myristoyl-amino-LNA 5-methyl-cytosine monomers, respectively. A, C, G and T denote LNA monomers, and a, c, g and t denote DNA monomers.

In Example 4 and the general disclosure, oligonucleotides containing two of such fatty acid conjugated amino-LNA modifications (e.g. palmitoyl-amino-LNA residues) distally positioned were disclosed and such "separated design" was shown to be a particularly preferred design in order to achieve high albumin binding for phosphodiester or phosphorothioate based antisense oligonucleotides. Data are reported in Example 4 for ODNs NAC7451, NAC7452, NAC7453, NAC7454, NAC7455 and NAC7456 to support the present invention and may be used in this Example for comparison.

Data reported reported below for NAC7716, NAC7717, NAC7718 and NAC 7719 show that two distally positioned myristoyl-amino-LNA monomers (NAC7717 and NAC 7719) induce similar albumin binding as do two distally positioned palmitoyl-amino-LNA monomers (NAC7453 and NAC7456). The data reported in this Example for the oligonucleotides NAC7714 and NAC7715, however, surprisingly show that close positioning of two acyl-amino-LNA monomers (here palmitoyl-amino-LNA monomers) likewise induce strong binding to human serum albumin. This protein is known to have binding sites for a fatty acid residue but it is highly surprising to see that two acyl chains positioned very closely, in the same half segment of an oligonucleotide as in NAC7714 and NAC7715, are able to promote such high albumin binding (see FIG. 4 to FIG. 9 and description below).

Data for Albumin/Oligonucleotide Complex Formation

The albumin to ODN ratios were titrated to visualize binding of the ODNs to albumin. The results are depicted in gels in FIG. 4 to FIG. 9 showing results for PO-ODNs to the left and results for PS-ODNs to the right. No significant albumin binding is observed neither for PO- nor PS-oligonucleotides without any acyl-amino-LNA monomers present. For the PO-ODNs with one palmitoyl-amino-LNA monomer, we observe only very weak interaction with albumin even at high surplus of albumin (40:1). For the PS-ODN, we see a weak binding to albumin, starting at an albumin:ODN ratio of 5:1. For the PO-ODN with two distally positioned palmitoyl-amino-LNA monomers, we observe an interaction with albumin starting at an albumin:ODN ratio of 5:1. For the PS-ODN even stronger binding to albumin is observed. For the PO-ODN with two palmitoyl-amino-LNA monomers at the 3'-end, we observe strong binding to albumin even at the lowest albumin to ODN ration. Slightly stronger binding is observed for the corresponding PS-ODN. For the PO-ODN with one myristoyl-amino-LNA monomer we observe no significant interaction with albumin. For the corresponding PS-ODN, indications of binding from an albumin:ODN ratio of 5:1 are seen.

For the PO-ODN with two distally positioned myristoyl-amino-LNA monomers we observe some binding from an albumin:ODN ratio of 5:1 whereas the corresponding PS-ODN shows binding already at the lowest albumin:ODN ratio.

Based on this Example, we conclude the following:
a) Oligonucleotides containing two fatty acid functionalized amino-LNA monomers show high binding to albumin.
b) Oligonucleotides containing two palmitoyl-amino-LNA monomers show high binding to albumin.
c) Oligonucleotides containing two myristoyl-amino-LNA monomers show high binding to albumin.
d) Oligonucleotides containing two closely positioned palmitoyl-amino-LNA monomers show high binding to albumin.
e) Gapmer antisense oligonucleotides containing two closely positioned palmitoyl-amino-LNA monomers show high binding to albumin.
f) Oligonucleotides with phosphodiester (PO) linkages and containing two fatty acid amino-LNA monomers show high binding to albumin.
g) Oligonucleotides with phosphorothioate (PS) linkages linkages and containing two fatty acid amino-LNA monomers in general show higher binding to albumin than do the corresponding oligonucleotides with phosphodiester (PO) linkages.
h) The fatty acid residue(s) present in the acyl-amino-LNA monomers seem(s) to be a key component to induce very efficient binding of ODNs to albumin.

Example 6: Derivatization of Aptamer AS1411 and an 11-Mer Aptamer Against CD-133

In the examples shown below, the following designations are used for the nucleotide monomers contained in the aptamer sequences:
small letters: DNA nucleotides
capital letters: LNA nucleotides
P: palmitoyl-amino-LNA-T nucleotide P*: palmitoyl-amino-LNA-5-methyl-C nucleotide
uC: UNA-C nucleotide
fC, fU: 2'-fluoro-2'-deoxynucleotides
rA: RNA-A nucleotide
mG: 2'-O-methyl-RNA nucleotides
Cy5 A fluorescent cyanine dye label (building block is commercially available)

AS1411 is a 26-mer all-DNA sequence (all internucleoside linkages are PO). The sequence of the parent AS1411 is shown here below:

```
                                           SEQ ID NO: 13
5'-ggt ggt ggt ggt tgt ggt ggt ggt gg
```

Two palmitoyl-amino-LNA monomers were attached directly to the 3'-end of AS1411 in one example:

```
                                           SEQ ID NO: 14
5'-ggt ggt ggt ggt tgt ggt ggt ggt ggPP
(all-PO linkages)
```

Two palmitoyl-amino-LNA monomers were attached via a trimer nucleotide linker (ttt) to the 3'-end of AS1411 in another example:

```
                                           SEQ ID NO: 15
5'-ggt ggt ggt ggt tgt ggt ggt ggt ggt ttP P
(all-PO linkages)
```

Below is shown the sequence of an aptamer which has been shown to bind to the CD133 epitope which is known to be overrepresented on e.g. colon cancer cells and other solid tumors and which is considered a cancer stem cell marker.

```
                                           SEQ ID NO: 16
5'-Cy5-CtfCuCfUrAfCrAfUAmG
```

In an example, two palmitoyl-amino-LNA monomers were introduced into this aptamer by substituting the two LNA nucleotides towards the 5'-end with two palmitoyl-amino-LNA monomers:

```
                                           SEQ ID NO: 17
5'-Cy5-P*PfCuCfUrAfCrAfUAmG
```

This example demonstrates the following:

The aptamers of the invention can be designed and synthesized as a variety of constructs.

The acyl- and/or alkyl-amino-LNA monomers can be incorporated toward one of the ends as extra nucleotides compared to the parent aptamer, and/or by substituting one or more of the nucleotides of the parent aptamer, and/or via an additional linker unit.

The aptamers of the invention may contain natural nucleotides as well as a variety of modified nucleotides plus the acyl- and/or alkyl-amino-LNA monomers.

The aptamers of the invention may contain conjugating moieties like a fluorescent group or may be conjugated to other groups, e.g. a reporter group.

Example 7: Fatty Acid-Modified Antisense Oligonucleotides Show Increased Circulatory Half-Life and Changed Biodistribution in Vivo This experiment was set up to explore the previous observation (see above) that antisense oligonucleotides (ODNs) modified with two acyl- or alkyl-amino-LNA monomers bind to albumin. The intention was to study if ODNs modified with two acyl- or alkyl-amino-LNA monomers display therapeutically relevant properties.

Previous examples have shown that palmitoylated ODNs of the invention bind to human serum albumin. The following antisense oligonucleotides (ODNs) were included each having a fluorescent label Cy5.5 attached to their 5'-end;

| | | |
|---|---|---|
| NAC7834 | 5'-Cy5.5-TAGcctgtcacttCTC (all-PO) | SEQ ID NO: 18 |
| NAC7833 | 5'-Cy5.5-TAGcctgtcacttCTC (all-PS) | SEQ ID NO: 19 |
| NAC7836 | 5'-Cy5.5-TAGcctgtcacttCPP* (all-PO) | SEQ ID NO: 20 |
| NAC7835 | 5'-Cy5.5-TAGcctgtcacttCPP* (all-PS) | SEQ ID NO: 21 |

P and P* denote palmitoyl-amino-LNA thymine and palmitoyl amino-LNA 5-methyl-cytosine monomer units, respectively. A, C, G and T denote LNA monomers, and a, c, g and t denote DNA monomers. Cy5.5 is a fluorescent cyanine dye label (building block for incorporation into an oligonucleotide is commercially available). These oligonucleotides are derivatives of the previously studied sequences NAC7451, NAC7454, NAC7714 and NAC7715.

Albumin/ODN Complex Formation

Figure 10:
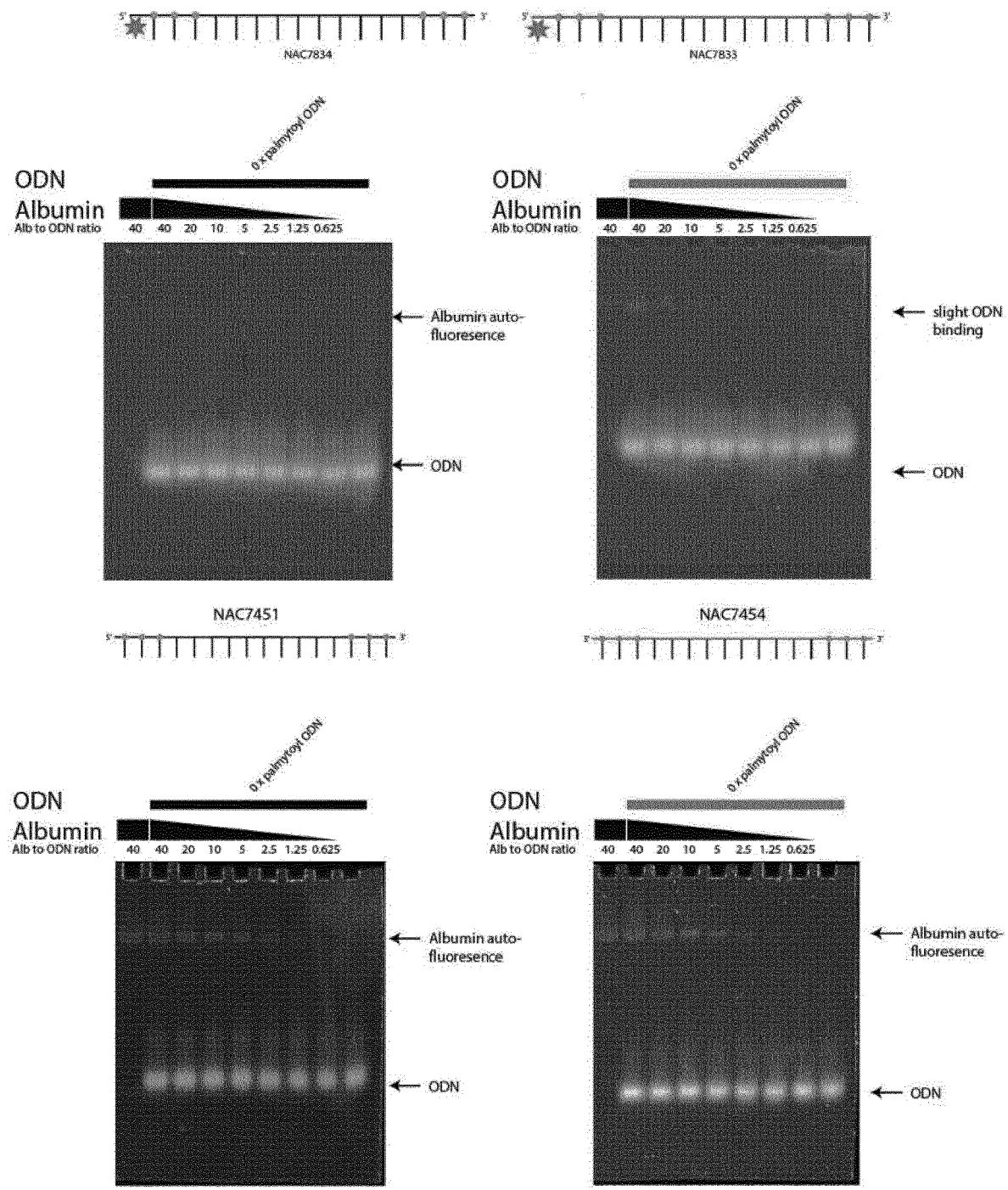
FIG. 10. PAGE of annealing of albumin/ODN complexes, using ODN with (left) PO or (right) PS linkages and no palmitoylated amino LNA modifications of Example 8. ODN is visualized by SYBR gold staining. Top: Fluorescent 2× palmitoyl ODNs titrated with different concentrations of albumin. Bottom: non-fluorescent 2× palmitoyl ODNs titrated with albumin (previous data; see FIG. 4).
Figure 11:
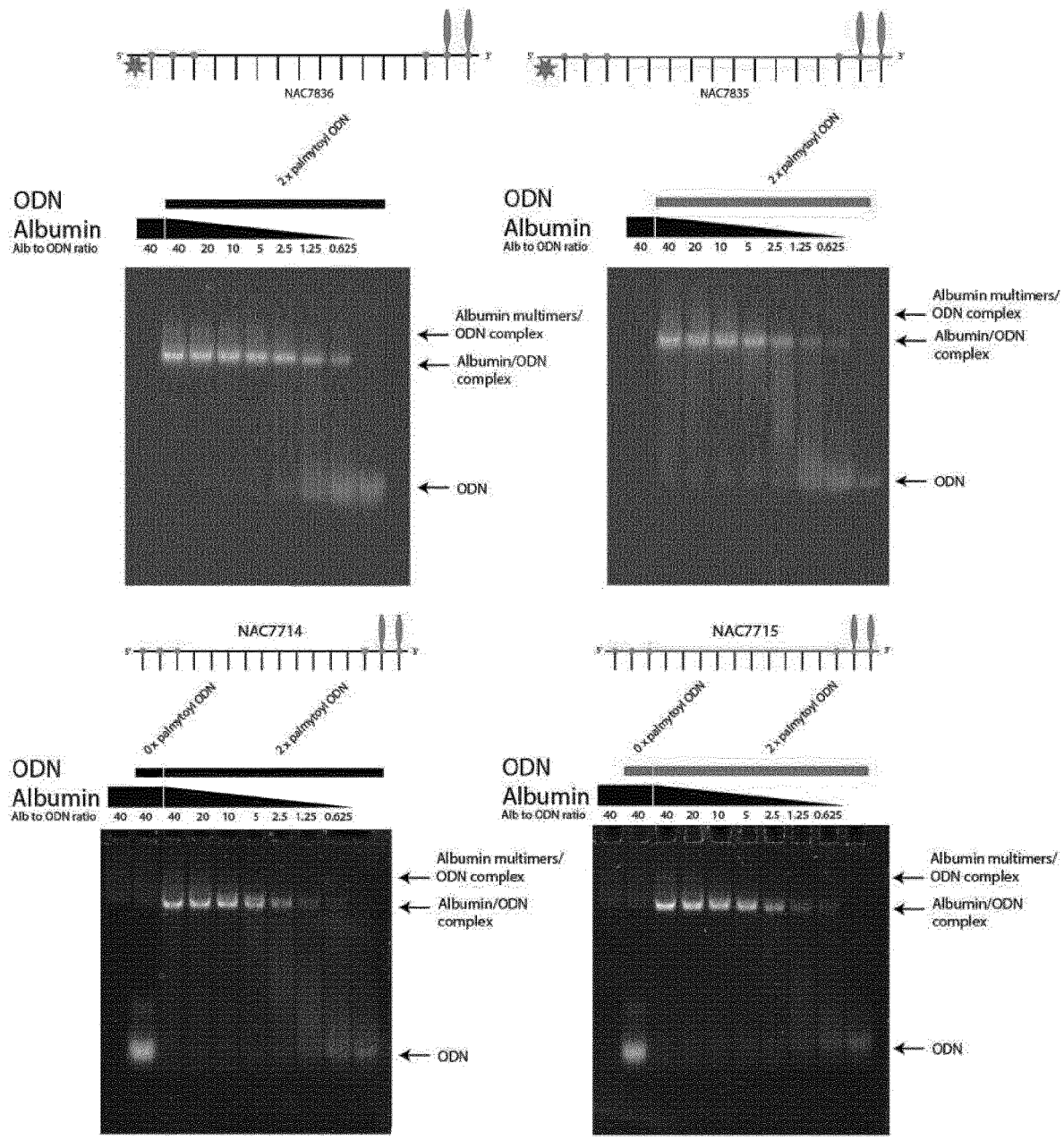
FIG. 11. PAGE of annealing of albumin/ODN complexes, using 3' double palmitoylated ODN with (left) PO or (right) PS linkages and no palmitoylated amino LNA modifications of Example 8. ODN is visualized by SYBR gold staining. Top: Fluorescent 2× palmitoyl ODNs titrated with different concentrations of albumin. Bottom: non-fluorescent 2× palmitoyl ODNs titrated with albumin (previous data; see FIG. 7).

Cy5.5 fluorescently labelled ODNs for in vivo half-life studies were initially incubated with albumin at different concentrations for 4 hours to confirm that the fluorophore does not interfere with the binding observed with the non-fluorescent ODNs tested previously. FIG. 10 and FIG. 11 show PAGE gels; on the left side ODNs with PO linkages was studied, on the right side ODNs with PS linkages.

For the ODNs without palmitoyl group, no binding for the ODN without PS-linkages is observed. For the ODNs without palmitoyl but with PS-linkages, a (very) slight binding is observed.

For the ODN with 2× palmitoyl in the 3' end of the ODN, we observe binding at the lowest ratios of albumin to ODN for both the ODN with and without PS-linkages. In general, we observe the same tendency for the ODNs with a 5'-Cy5.5 fluorophore as for the ODNs without the label.

In Vivo Circulatory Half-Life

Cy5.5 fluorescently labelled ODNs were injected intravenously into the tail vein of 8-9 weeks old female C57BL/6 mice. The mice were dosed 3.5 mg/kg ODN in a total volume of 200 µl. Blood was collected from the tongue after 1 min and from the tail after 30 min, 2 hours, 4 hours, and 24 hours. Plasma was isolated and scanned in the IVIS scanner. After 24 hours, the animals were sacrificed, and organs and corpus scanned in the IVIS scanner. Experimental time line is given in FIG. 12, top.

Figure 12:
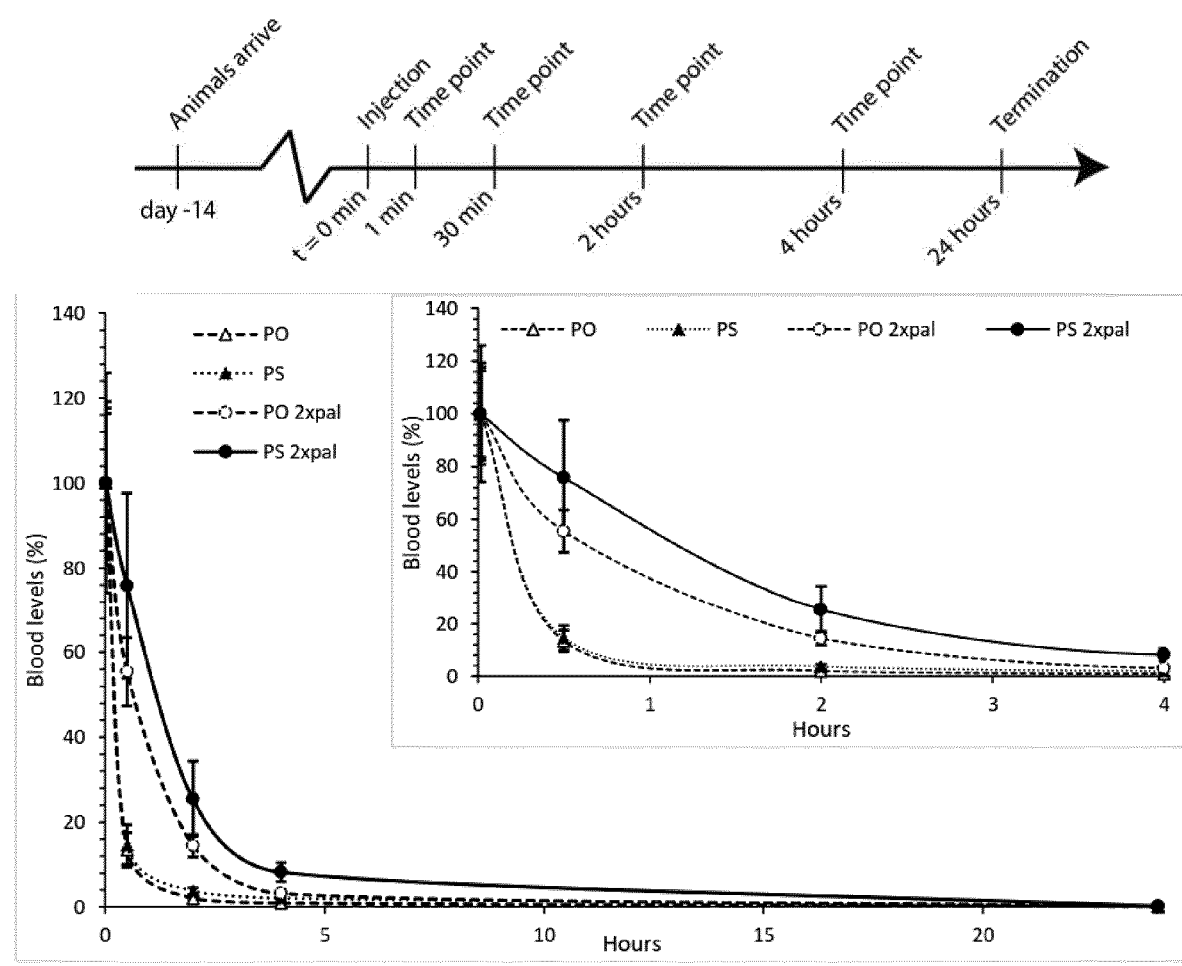
FIG. 12. Plasma levels of Cy5.5 fluorescent ODN constructs at given time points of Example 7. Fluorescence was quantified using Living Image (Perkin Elmer), and the amounts normalised to the levels after 1 minute. Insert in top right corner is a zoom in on the first 4 hours. An experimental time line is shown at the top.
Figure 13:
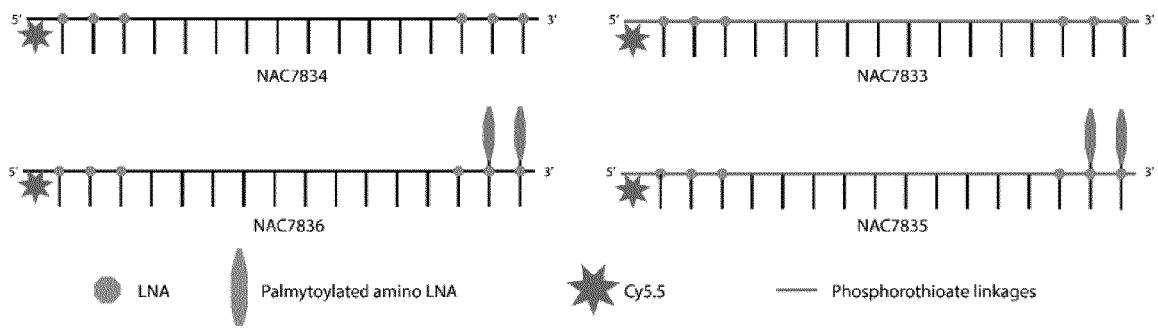
FIG. 13. Graphic representation of modified ODNs, with reference numbers, used in Example 7.

We observe an increased half-life for the palmitoylated ODNs NAC7835 and NAC7836, compared to the naked ODNs, cf. FIG. 12 (see also the schematic representation of the studied oligonucleotides in FIG. 13). Furthermore, we observe an increased half-life for the ODNs with PS linkages compared to the ODN with PO linkages, but still a notable increase for NAC7836 (all PO linkages) compared to both NAC7834 (reference with all PO linkages) and NAC 7833 (reference with all PS linkages). Fitting an exponential decay curve gave the following half-lives: 23 min, 28 min, 49 min, and 66 min (PO [NAC7834], PS [NAC7833], PO 2xpal [NAC7836], and PS 2xpal [NAC7835] respectively). Notably, modifying the all PO ODN [NAC7834] with palmitoyl [NAC7836] yielded more than a two fold increase in circulatory half-life.

Oman Biodistribution

Figure 14:
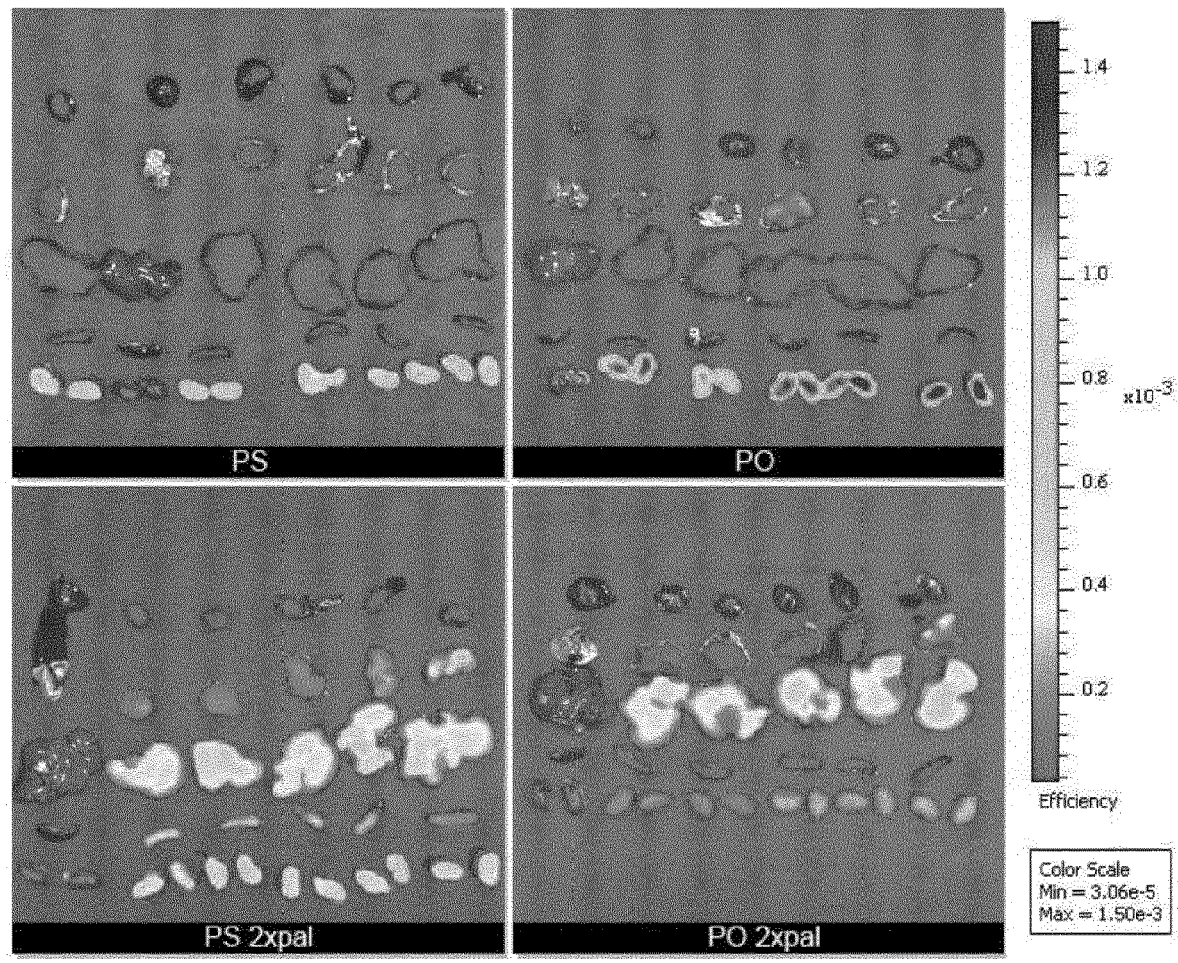
FIG. 14. Organs from mice scanned in the IVIS scanner, 24 hours after injection (Example 7). Organs are from top to bottom: heart, lung, liver, spleen, and kidneys. For PS, second mouse from the left is PBS control, for the PO, PS 2xpal, and PO 2xpal, the left mouse is PBS control. All images were acquired separately, loaded as a group and normalised to the same scale using the Living Images software (Perkin Elmer).
Figure 15:
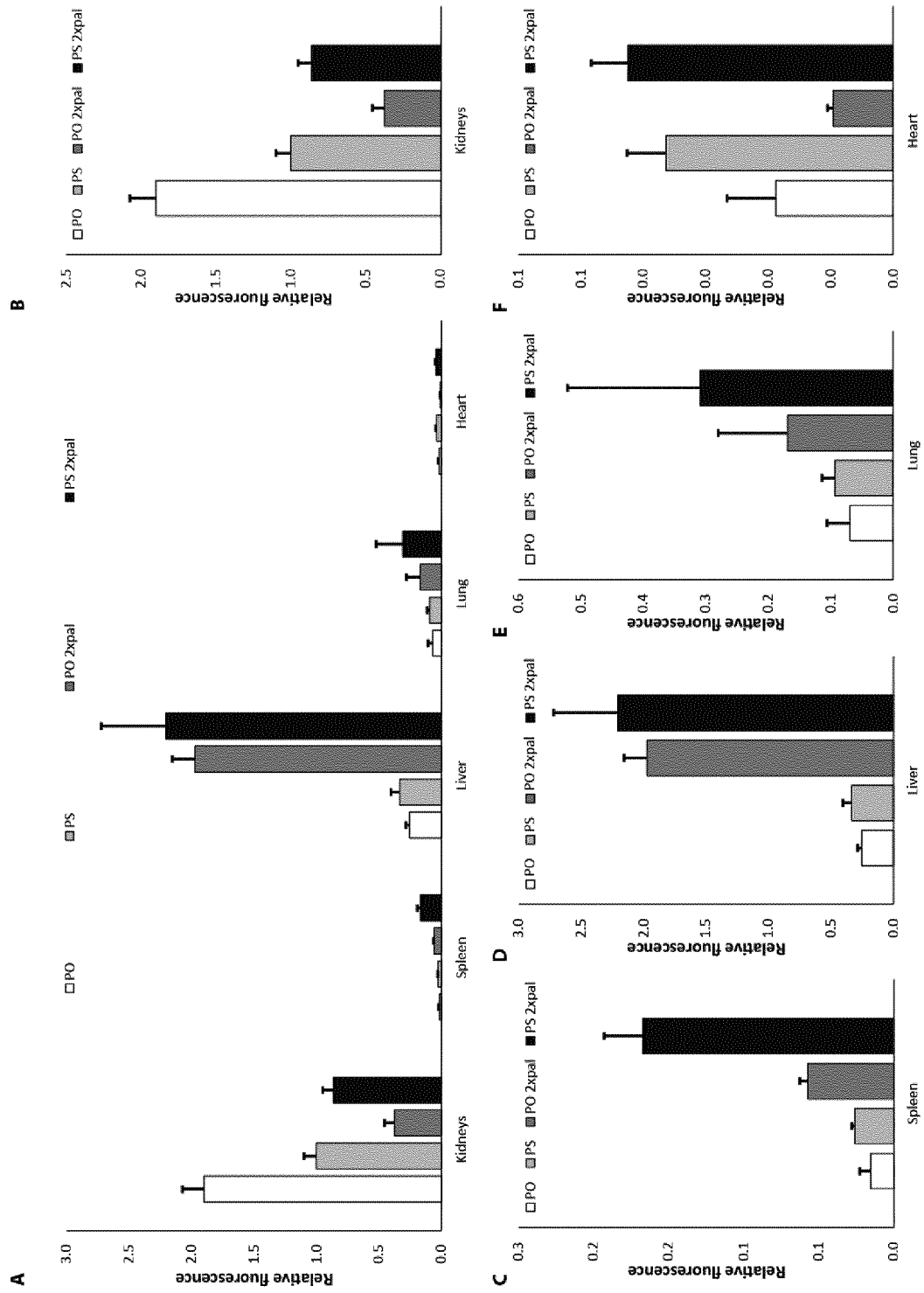
FIG. 15. Quantification of fluorescence from isolated organs scanned in the IVIS scanner, 24 hours after injection. The fluorescence intensity was normalised to the signal from the PS kidney and presented as means with standard deviation (N=5).

Scanning the organs revealed an accumulation within the kidney for the non-palmitoylated ODNs [NAC7834 and NAC 7833] with a higher accumulation for the PO ODN [NAC7834], cf. FIG. 14. However, for the 2xpal ODNs, we observe a much more even distribution throughout the organs (FIG. 14 and FIG. 15) meaning that the two palmitoyl amino-LNA monomers present in NAC7836 and NAC7835 affect biodistribution with less accumulation in the kidneys and more accumulation in liver and spleen, all relative to the corresponding non-palmitoylated ODNs NAC7834 and NAC7833. The data obtained indicate that biodistribution to a number of organs can be affected by the application of the constructs of this invention. A likely explanation for the increased circulatory half-life in vivo and the changed biodistribution patterns observed for the ODNs containing two palmitoyl-amino-LNA monomers is the increased binding to albumin as demonstrated in previous examples.

Example 8. Unassisted Uptake in Chondrocytes Studied by Confocal Microscopy and Flow Cytometry The gapmers listed below were included in this study:

```
NAC7771   5'-Cy3-GTCctcgagcgtCTC (all-PS)         SEQ ID NO: 22

NAC7772   5'-Cy3-GPCctcgagcgtCPC (all-PO)         SEQ ID NO: 23

NAC7773   5'-Cy3-GPCctcgagcgtCPC (all-PS)         SEQ ID NO: 24

NAC7774   5'-Cy3-GT*C*ctcgagcgtC*T*C (all-PS)     SEQ ID NO: 25

NAC7775   5'-Cy3-GTCctcgagcgtCTC (all-PS)     SEQ ID NO: 26
```
P denotes a palmitoyl-amino-LNA thymine monomer.
T* and C* denote glycyl-amino-LNA thymine and 5-methylcytosine monomers, respectively.
T** denotes a galactosyl-functionalized amino-LNA thymine monomer with a -C(=O)CH$_2$- linker between the N2'-atom and the O1-atom of the beta-configured galactosyl unit (i.e. a N2'-C(=O)CH$_2$-O1 linker). A, C, G and T denote LNA monomers, and a, c, g and t denote DNA monomers.

Figure 16:
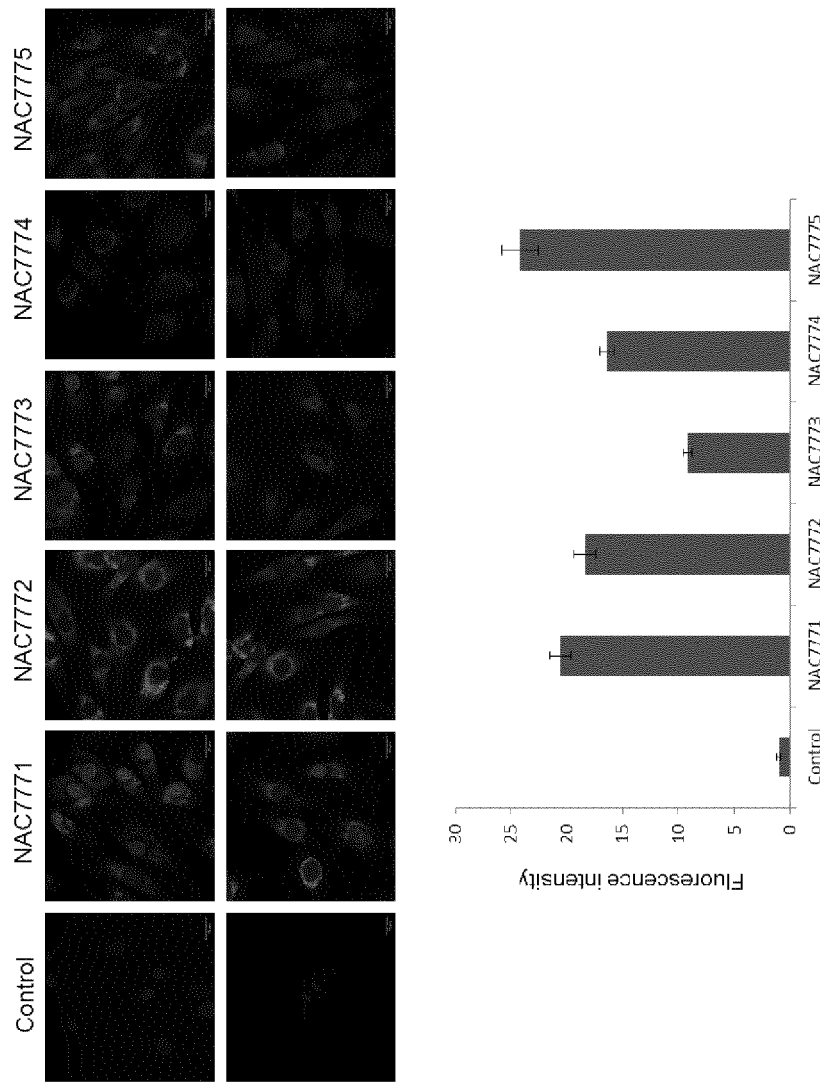
FIG. 16. Confocal microscopy pictures and flow cytometry results after unassisted uptake in chondrocytes (Example 8).

Confocal microscopy analysis of gapmer uptake at 50 nM upon incubation with human chondrocytes after 24 h was performed. Nuclei were stained with Hoechst and gapmer were labeled with Cy3 (red). Original magnification 40×. The results are depicted in FIG. 16. (in the upper part). Control is no Cy3-labelled oligonucleotide added. The uptake was also evaluated using flow cytometry analysis of gapmer uptake at 50 nM upon incubation with human chondrocytes after 24 h (FIG. 16, Bottom).

It can be concluded, that the LNA-DNA-LNA gapmer control (NAC7771; all PS linkages) as expected is efficiently taken up in chondrocytes using unassisted uptake conditions with no transfection agent added. Also oligonucleotides with two palmitoyl-amino-LNA monomers, both as all-PO (NAC7772) and all-PS (NAC7773) derivative, are efficiently taken up in chondrocytes using unassisted uptake conditions with no transfection agent added. It should be noted that the uptake of the all-PO variant NAC7772 is more efficient than the uptake of the all-PS variant NAC773. Furthermore are oligonucleotides with four glycyl-amino-LNA monomers (NAC7774; all-PS) and with two galactosyl-functionalized alkyl-amino-LNA monomers (NAC7775; all-PS) efficiently taken up in chondrocytes using unassisted uptake conditions with no transfection agent added.

The content of the following four Danish priority applications is included herein by reference in their entireties: PA 2015 00090 filed Feb. 15, 2015, PA 2015 00440 filed Aug. 8, 2015, PA 2015 00711 filed Nov. 10, 2015, and PA 2015 00712 filed Nov. 10, 2015.

The invention claimed is:

1. A single stranded oligonucleotide containing two or more acyl-amino-LNA-nucleotide monomers,
    wherein other nucleotide monomers can be DNA, RNA or chemically modified nucleotide monomers; wherein the monomers of the oligonucleotide are linked by phosphodiester linkages and/or phosophorothioate linkages and/or phosphotriester linkages,
    wherein the acyl group of each acyl-amino-LNA monomer is independently substituted or unsubstituted, wherein the substituted monomers contain one or more groups selected from hydroxyl, amino, thio, oxo, alkyl, thio, ether, and thiol, and
    wherein the acyl group of each acyl-amino-LNA monomer is independently —C(=O)R and R is a linear or branched $C_6$-$C_{15}$ alkyl.

2. The single stranded oligonucleotide according to claim 1, wherein at least 50% of all internucleoside linkages of said oligonucleotide are phosphodiester linkages.

3. The single stranded oligonucleotide according to claim 1, wherein at most 40% of nucleotide monomers of said oligonucleotide are ribonucleotide monomers.

4. The single stranded oligonucleotide according to claim 1, said oligonucleotide containing one or two nucleotide monomers that are linked to a cholesteryl moiety.

5. The single stranded oligonucleotide according to claim 1, wherein the acyl moieties of said acyl-amino-LNA nucleotide monomers are N-alkanoyl, N-alkenyol and/or N-alkynoyl moieties, said acyl moiety being unsubstituted or substituted with one or more groups selected from hydroxy, $C_1$-$C_6$ alkoxy, amino, $C_1$-$C_6$ mono or dialkylamino, oxo, thiol, and $C_1$-$C_6$ alkylthio groups.

6. The single stranded oligonucleotide according to claim 1, wherein said oligonucleotide comprises at least 7 nucleotide monomer units.

7. The single stranded oligonucleotide according to claim 1, wherein all nucleotide monomer units of said oligonucleotide are linked by phosphodiester linkages.

8. The single stranded oligonucleotide according to claim 1, which is a gapmer, an aptamer, or a mixmer.

9. The single stranded oligonucleotide according to claim 1, wherein said oligonucleotide has, from the 5'-end to the 3'-end, three segments: a 5'-end segment of at least 2 nucleotide units, a central binding segment of at least 6 nucleotide units in length, and a 3'-end segment of at least 2 nucleotide units in length,
wherein said oligonucleotide contains at least two 2'-N-acyl-2'-amino-LNA monomers in either the 5'-end segment or the 3'end segment but none in the central segment; or contains at least one 2'-N-acyl-2'-amino-LNA nucleotide monomer in each of said end segments, but none in the central segment.

10. The single stranded oligonucleotide according to claim 1, wherein the oligonucleotide is a gapmer of the following constitution:

Nv-My-Nz, wherein M denotes a nucleotide monomer compatible with RNase H degradation of the target RNA, N denotes monomers selected from among affinity-enhancing nucleotide monomers, acyl-amino-LNA and/or hydrocarbyl-amino-LNA-monomers, and DNA nucleotide monomers, and wherein V, Y and Z signify the numbers of the monomers in segments Ny, My, and Nz, wherein My is the gap segment and Nv and Nz are wing segments composed of N monomers, and where the hyphens indicate connection of the segments the numbers V and Z may vary from 2 to 8 and the number Y may vary from 6 to 14, provided that the sum of V+Z+Y is maximum 30, with the provision that
(a) at least one acyl-amino-LNA and/or hydrocarbyl-amino-LNA monomer is present in each of the wing segments; or
(b) at least two acyl-amino-LNA and/or hydrocarbyl-amino-LNA monomers are present in one of the wing segments.

11. The single stranded oligonucleotide according to claim 10, wherein the oligonucleotide is of the following constitution $5'$-$(L)_{2-4}$-$(D)_{6-10}$-$(L)_{2-4}$, where D denotes a DNA nucleotide monomer and L denotes an affinity-enhancing nucleotide monomer or an acyl-amino-LNA and/or hydrocarbyl-amino-LNA monomer, provided that
(a) at least one acyl-amino-LNA and/or hydrocarbyl-amino-LNA monomer is present in each of the wing segments, i.e. the segments composed of the L monomers; or
(b) at least two acyl-amino-LNA and/or hydrocarbyl-amino-LNA monomers are present in one of the wing segments, i.e. the segments composed of the L monomers.

12. An antisense oligonucleotide according to claim 1, which is able to mediate gene regulation by RNase-H mediated antisense RNA targeting.

13. The single stranded oligonucleotide according to claim 1, wherein at least two acyl-amino-LNA monomers are present in either a 5'-end half of the oligonucleotide or a 3'-end half of the oligonucleotide, and when the total number of nucleotide monomers in the oligonucleotide is an odd number a central nucleotide monomer is part of the 5'-end half.

14. A method for mediating gene silencing in a cell or an organism, comprising contacting said cell or organism with an oligonucleotide of claim 1 under conditions wherein gene silencing can occur.

15. The method according to claim 14, said method being performed in vitro or on an isolated cell; or said method being performed in vivo in a whole animal or in a human.

16. The method according to claim 14, wherein said oligonucleotide has complementarity to a target gene or target RNA expressed in said cell or organism for mediating silencing of the target gene or target RNA, mediated by RNase H.

17. The oligonucleotide of claim 1, wherein said oligonucleotide has complementarity to a target gene or target RNA for mediating silencing of the target gene or target RNA, preferably mediated by RNase H.

18. A pharmaceutical composition comprising the oligonucleotide of claim 1 and a pharmaceutically acceptable diluent, carrier or adjuvant.

19. The oligonucleotide of claim 1, wherein the two or more acyl-amino-LNA nucleotide monomers are selected from glycyl-amino-LNA monomers, palmitoyl-amino-LNA-monomers, and myristoyl-amino-LNA monomers.

20. The oligonucleotide of claim 1, wherein the oligonucleotide contains one or more conjugating groups attached at the 3'- and/or the 5'-end of the oligonucleotide.

21. A reagent containing the oligonucleotide of claim 1.

* * * * *

```
                         SEQUENCE LISTING

<160> NUMBER OF SEQ ID NOS: 29

<210> SEQ ID NO 1
<211> LENGTH: 16
<212> TYPE: DNA
<213> ORGANISM: Artificial Sequence
<220> FEATURE:
<223> OTHER INFORMATION: oligo
<220> FEATURE:
<221> NAME/KEY: misc_feature
<222> LOCATION: (1)..(3)
<223> OTHER INFORMATION: stretch of LNAs with bases TAG
<220> FEATURE:
<221> NAME/KEY: misc_feature
<222> LOCATION: (14)..(16)
<223> OTHER INFORMATION: stretch of LNAs with bases CTC

<400> SEQUENCE: 1
nnncctgtca cttnnn                                                  16

<210> SEQ ID NO 2
<211> LENGTH: 16
<212> TYPE: DNA
<213> ORGANISM: Artificial Sequence
<220> FEATURE:
<223> OTHER INFORMATION: palmitoyl-amino-LNA containing oligo
<220> FEATURE:
<221> NAME/KEY: misc_feature
<222> LOCATION: (1)..(1)
<223> OTHER INFORMATION: palmitoyl-amino-LNA-T
<220> FEATURE:
<221> NAME/KEY: misc_feature
<222> LOCATION: (2)..(3)
<223> OTHER INFORMATION: LNA stretch bases AG
<220> FEATURE:
<221> NAME/KEY: misc_feature
<222> LOCATION: (14)..(16)
<223> OTHER INFORMATION: LNA stretch bases ctc

<400> SEQUENCE: 2
nnncctgtca cttnnn                                                  16

<210> SEQ ID NO 3
<211> LENGTH: 16
<212> TYPE: DNA
<213> ORGANISM: Artificial Sequence
<220> FEATURE:
<223> OTHER INFORMATION: palmitoyl-amino-LNA containing oligo
<220> FEATURE:
<221> NAME/KEY: misc_feature
<222> LOCATION: (1)..(1)
<223> OTHER INFORMATION: palmitoyl-amino-LNA-T
<220> FEATURE:
<221> NAME/KEY: misc_feature
<222> LOCATION: (2)..(3)
```

```
<223> OTHER INFORMATION: LNA stretch bases AG
<220> FEATURE:
<221> NAME/KEY: misc_feature
<222> LOCATION: (14)..(14)
<223> OTHER INFORMATION: palmitoyl-amino-LNA-5-methyl-cytosine
<220> FEATURE:
<221> NAME/KEY: misc_feature
<222> LOCATION: (15)..(16)
<223> OTHER INFORMATION: LNA stretch bases TC

<400> SEQUENCE: 3
nnncctgtca cttnnn                                                     16

<210> SEQ ID NO 4
<211> LENGTH: 16
<212> TYPE: DNA
<213> ORGANISM: Artificial Sequence
<220> FEATURE:
<223> OTHER INFORMATION: oligo
<220> FEATURE:
<221> NAME/KEY: misc_feature
<222> LOCATION: (1)..(3)
<223> OTHER INFORMATION: stretch of LNAs with bases tag
<220> FEATURE:
<221> NAME/KEY: misc_feature
<222> LOCATION: (14)..(16)
<223> OTHER INFORMATION: stretch of LNAs with bases ctc

<400> SEQUENCE: 4
nnncctgtca cttnnn                                                     16

<210> SEQ ID NO 5
<211> LENGTH: 16
<212> TYPE: DNA
<213> ORGANISM: Artificial Sequence
<220> FEATURE:
<223> OTHER INFORMATION: palmitoyl-amino-LNA containing oligo
<220> FEATURE:
<221> NAME/KEY: misc_feature
<222> LOCATION: (1)..(1)
<223> OTHER INFORMATION: palmitoyl-amino-LNA-T
<220> FEATURE:
<221> NAME/KEY: misc_feature
<222> LOCATION: (2)..(3)
<223> OTHER INFORMATION: strech of LNAs bases AG
<220> FEATURE:
<221> NAME/KEY: misc_feature
<222> LOCATION: (14)..(16)
<223> OTHER INFORMATION: strech of LNAs bases CTC

<400> SEQUENCE: 5
nnncctgtca cttnnn                                                     16

<210> SEQ ID NO 6
<211> LENGTH: 16
<212> TYPE: DNA
<213> ORGANISM: Artificial Sequence
<220> FEATURE:
<223> OTHER INFORMATION: palmitoyl-amino-LNA containing oligo
<220> FEATURE:
<221> NAME/KEY: misc_feature
<222> LOCATION: (1)..(1)
<223> OTHER INFORMATION: palmitoyl-amino-LNA-T
<220> FEATURE:
<221> NAME/KEY: misc_feature
<222> LOCATION: (2)..(3)
<223> OTHER INFORMATION: stretch of LNAs bases AG
<220> FEATURE:
<221> NAME/KEY: misc_feature
<222> LOCATION: (14)..(14)
<223> OTHER INFORMATION: myristoyl-amino-LNA-5-methyl-cytosine
<220> FEATURE:
<221> NAME/KEY: misc_feature
```

<222> LOCATION: (15)..(16)
<223> OTHER INFORMATION: stretch of LNAs bases TC

<400> SEQUENCE: 6
nnncctgtca cttnnn                                                         16

<210> SEQ ID NO 7
<211> LENGTH: 16
<212> TYPE: DNA
<213> ORGANISM: Artificial Sequence
<220> FEATURE:
<223> OTHER INFORMATION: LNA containing oligo
<220> FEATURE:
<221> NAME/KEY: misc_feature
<222> LOCATION: (1)..(3)
<223> OTHER INFORMATION: stretch of LNAs bases TAG
<220> FEATURE:
<221> NAME/KEY: misc_feature
<222> LOCATION: (14)..(14)
<223> OTHER INFORMATION: LNA-C
<220> FEATURE:
<221> NAME/KEY: misc_feature
<222> LOCATION: (15)..(15)
<223> OTHER INFORMATION: palmitoyl-amino-LNA-T
<220> FEATURE:
<221> NAME/KEY: misc_feature
<222> LOCATION: (16)..(16)
<223> OTHER INFORMATION: palmitoyl-amino-LNA-5-methyl-cytosine

<400> SEQUENCE: 7
nnncctgtca cttnnn                                                         16

<210> SEQ ID NO 8
<211> LENGTH: 16
<212> TYPE: DNA
<213> ORGANISM: Artificial Sequence
<220> FEATURE:
<223> OTHER INFORMATION: LNA and amino-LNA containing oligo
<220> FEATURE:
<221> NAME/KEY: misc_feature
<222> LOCATION: (1)..(3)
<223> OTHER INFORMATION: stretch of LNAs bases TAG
<220> FEATURE:
<221> NAME/KEY: misc_feature
<222> LOCATION: (14)..(14)
<223> OTHER INFORMATION: LNA-C
<220> FEATURE:
<221> NAME/KEY: misc_feature
<222> LOCATION: (15)..(15)
<223> OTHER INFORMATION: palmitoyl-amino-LNA-T
<220> FEATURE:
<221> NAME/KEY: misc_feature
<222> LOCATION: (16)..(16)
<223> OTHER INFORMATION: palmitoyl-amino-LNA-5-methyl-cytosine

<400> SEQUENCE: 8
nnncctgtca cttnnn                                                         16

<210> SEQ ID NO 9
<211> LENGTH: 16
<212> TYPE: DNA
<213> ORGANISM: Artificial Sequence
<220> FEATURE:
<223> OTHER INFORMATION: LNA and amino-LNA containing oligo
<220> FEATURE:
<221> NAME/KEY: misc_feature
<222> LOCATION: (1)..(1)
<223> OTHER INFORMATION: myristoyl-amino-LNA-T
<220> FEATURE:
<221> NAME/KEY: misc_feature
<222> LOCATION: (2)..(3)
<223> OTHER INFORMATION: stretch of LNAs AG
<220> FEATURE:

```
<221> NAME/KEY: misc_feature
<222> LOCATION: (14)..(16)
<223> OTHER INFORMATION: stretch of LNAs CTC

<400> SEQUENCE: 9
nnncctgtca cttnnn                                               16

<210> SEQ ID NO 10
<211> LENGTH: 16
<212> TYPE: DNA
<213> ORGANISM: Artificial Sequence
<220> FEATURE:
<223> OTHER INFORMATION: LNA and amino-LNA containing oligo
<220> FEATURE:
<221> NAME/KEY: misc_feature
<222> LOCATION: (1)..(1)
<223> OTHER INFORMATION: myristoyl-amino-LNA-T
<220> FEATURE:
<221> NAME/KEY: misc_feature
<222> LOCATION: (2)..(3)
<223> OTHER INFORMATION: stretch of LNAs AG
<220> FEATURE:
<221> NAME/KEY: misc_feature
<222> LOCATION: (14)..(14)
<223> OTHER INFORMATION: myristoyl-amino-LNA-5-methyl-cytosine
<220> FEATURE:
<221> NAME/KEY: misc_feature
<222> LOCATION: (15)..(16)
<223> OTHER INFORMATION: stretch of LNAs bases TC

<400> SEQUENCE: 10
nnncctgtca cttnnn                                               16

<210> SEQ ID NO 11
<211> LENGTH: 16
<212> TYPE: DNA
<213> ORGANISM: Artificial Sequence
<220> FEATURE:
<223> OTHER INFORMATION: LNA and amino-LNA containing oligo
<220> FEATURE:
<221> NAME/KEY: misc_feature
<222> LOCATION: (1)..(1)
<223> OTHER INFORMATION: myristoyl-amino-LNA-T
<220> FEATURE:
<221> NAME/KEY: misc_feature
<222> LOCATION: (2)..(3)
<223> OTHER INFORMATION: LNAs AG
<220> FEATURE:
<221> NAME/KEY: misc_feature
<222> LOCATION: (14)..(16)
<223> OTHER INFORMATION: LNAs CTS

<400> SEQUENCE: 11
nnncctgtca cttnnn                                               16

<210> SEQ ID NO 12
<211> LENGTH: 16
<212> TYPE: DNA
<213> ORGANISM: Artificial Sequence
<220> FEATURE:
<223> OTHER INFORMATION: LNA and amino-LNA containing oligo
<220> FEATURE:
<221> NAME/KEY: misc_feature
<222> LOCATION: (1)..(1)
<223> OTHER INFORMATION: myristoyl-amino-LNA-T
<220> FEATURE:
<221> NAME/KEY: misc_feature
<222> LOCATION: (2)..(3)
<223> OTHER INFORMATION: stretch of LNAs bases AG
<220> FEATURE:
<221> NAME/KEY: misc_feature
<222> LOCATION: (14)..(14)
<223> OTHER INFORMATION: myristoyl-amino-LNA-5-methyl-cytosine
```

```
<220> FEATURE:
<221> NAME/KEY: misc_feature
<222> LOCATION: (15)..(16)
<223> OTHER INFORMATION: stretch of LNAs basesTC

<400> SEQUENCE: 12
nnncctgtca cttnnn                                                    16

<210> SEQ ID NO 13
<211> LENGTH: 26
<212> TYPE: DNA
<213> ORGANISM: Artificial Sequence
<220> FEATURE:
<223> OTHER INFORMATION: oligo

<400> SEQUENCE: 13
ggtggtggtg gttgtggtgg tggtgg                                         26

<210> SEQ ID NO 14
<211> LENGTH: 28
<212> TYPE: DNA
<213> ORGANISM: Artificial Sequence
<220> FEATURE:
<223> OTHER INFORMATION: palmitoyl-amino-LNA-T -containing oligo
<220> FEATURE:
<221> NAME/KEY: misc_feature
<222> LOCATION: (27)..(28)
<223> OTHER INFORMATION: palmitoyl-amino-LNA-T

<400> SEQUENCE: 14
ggtggtggtg gttgtggtgg tggtggnn                                       28

<210> SEQ ID NO 15
<211> LENGTH: 31
<212> TYPE: DNA
<213> ORGANISM: Artificial Sequence
<220> FEATURE:
<223> OTHER INFORMATION: palmitoyl-amino-LNA-T -containing oligo
<220> FEATURE:
<221> NAME/KEY: misc_feature
<222> LOCATION: (30)..(31)
<223> OTHER INFORMATION: palmitoyl-amino-LNA-T

<400> SEQUENCE: 15
ggtggtggtg gttgtggtgg tggtggtttn n                                   31

<210> SEQ ID NO 16
<211> LENGTH: 11
<212> TYPE: DNA
<213> ORGANISM: Artificial Sequence
<220> FEATURE:
<223> OTHER INFORMATION: multiply modified oligo
<220> FEATURE:
<221> NAME/KEY: misc_feature
<222> LOCATION: (1)..(1)
<223> OTHER INFORMATION: LNA-C
<220> FEATURE:
<221> NAME/KEY: misc_feature
<222> LOCATION: (3)..(3)
<223> OTHER INFORMATION: 2'-fluoro-2'-deoxy-U
<220> FEATURE:
<221> NAME/KEY: misc_feature
<222> LOCATION: (3)..(3)
<223> OTHER INFORMATION: 2'-fluoro-2'-deoxy-C
<220> FEATURE:
<221> NAME/KEY: misc_feature
<222> LOCATION: (4)..(4)
<223> OTHER INFORMATION: UNA-C
<220> FEATURE:
<221> NAME/KEY: misc_feature
<222> LOCATION: (5)..(5)
```

```
<223> OTHER INFORMATION: 2'-fluoro-2'-deoxy-U
<220> FEATURE:
<221> NAME/KEY: misc_feature
<222> LOCATION: (6)..(6)
<223> OTHER INFORMATION: RNA-A
<220> FEATURE:
<221> NAME/KEY: misc_feature
<222> LOCATION: (7)..(7)
<223> OTHER INFORMATION: 2'-fluoro-2'-deoxy-C
<220> FEATURE:
<221> NAME/KEY: misc_feature
<222> LOCATION: (8)..(8)
<223> OTHER INFORMATION: RNA-A
<220> FEATURE:
<221> NAME/KEY: misc_feature
<222> LOCATION: (9)..(9)
<223> OTHER INFORMATION: 2'-fluoro-2'-deoxy-U
<220> FEATURE:
<221> NAME/KEY: misc_feature
<222> LOCATION: (10)..(10)
<223> OTHER INFORMATION: LNA-A
<220> FEATURE:
<221> NAME/KEY: misc_feature
<222> LOCATION: (11)..(11)
<223> OTHER INFORMATION: 2'-O-methyl-RNA G

<400> SEQUENCE: 16
ntnnnnnnnn n                                                          11

<210> SEQ ID NO 17
<211> LENGTH: 11
<212> TYPE: DNA
<213> ORGANISM: Artificial Sequence
<220> FEATURE:
<223> OTHER INFORMATION: multiply modified oligo
<220> FEATURE:
<221> NAME/KEY: misc_feature
<222> LOCATION: (1)..(1)
<223> OTHER INFORMATION: palmitoyl-amino-LNA-5-methyl-cytosine
<220> FEATURE:
<221> NAME/KEY: misc_feature
<222> LOCATION: (2)..(2)
<223> OTHER INFORMATION: palmitoyl-amino-LNA-T
<220> FEATURE:
<221> NAME/KEY: misc_feature
<222> LOCATION: (3)..(3)
<223> OTHER INFORMATION: 2'-fluoro-2'-deoxy-C
<220> FEATURE:
<221> NAME/KEY: misc_feature
<222> LOCATION: (4)..(4)
<223> OTHER INFORMATION: UNA-C
<220> FEATURE:
<221> NAME/KEY: misc_feature
<222> LOCATION: (5)..(5)
<223> OTHER INFORMATION: 2'-fluoro-2'-deoxy-U
<220> FEATURE:
<221> NAME/KEY: misc_feature
<222> LOCATION: (6)..(6)
<223> OTHER INFORMATION: RNA-A
<220> FEATURE:
<221> NAME/KEY: misc_feature
<222> LOCATION: (7)..(7)
<223> OTHER INFORMATION: 2'-fluoro-2'-deoxy-C
<220> FEATURE:
<221> NAME/KEY: misc_feature
<222> LOCATION: (8)..(8)
<223> OTHER INFORMATION: RNA-A
<220> FEATURE:
<221> NAME/KEY: misc_feature
<222> LOCATION: (9)..(9)
<223> OTHER INFORMATION: 2'-fluoro-2'-deoxy-U
<220> FEATURE:
<221> NAME/KEY: misc_feature
<222> LOCATION: (10)..(10)
<223> OTHER INFORMATION: LNA-A
<220> FEATURE:
<221> NAME/KEY: misc_feature
```

```
<222> LOCATION: (11)..(11)
<223> OTHER INFORMATION: 2'-O-methyl-RNA G

<400> SEQUENCE: 17
nnnnnnnnnn n                                                              11

<210> SEQ ID NO 18
<211> LENGTH: 16
<212> TYPE: DNA
<213> ORGANISM: Artificial Sequence
<220> FEATURE:
<223> OTHER INFORMATION: multiply modified oligo
<220> FEATURE:
<221> NAME/KEY: misc_feature
<222> LOCATION: (1)..(3)
<223> OTHER INFORMATION: LNAs bases TAG
<220> FEATURE:
<221> NAME/KEY: misc_feature
<222> LOCATION: (1)..(3)
<223> OTHER INFORMATION: LNAs bases TAG, Cy5.5-labeled
<220> FEATURE:
<221> NAME/KEY: misc_feature
<222> LOCATION: (14)..(16)
<223> OTHER INFORMATION: LNAs bases ctc

<400> SEQUENCE: 18
nnncctgtca cttnnn                                                         16

<210> SEQ ID NO 19
<211> LENGTH: 16
<212> TYPE: DNA
<213> ORGANISM: Artificial Sequence
<220> FEATURE:
<223> OTHER INFORMATION: multiply modified oligo
<220> FEATURE:
<221> NAME/KEY: misc_feature
<222> LOCATION: (1)..(3)
<223> OTHER INFORMATION: LNAs bases TAG
<220> FEATURE:
<221> NAME/KEY: misc_feature
<222> LOCATION: (14)..(16)
<223> OTHER INFORMATION: LNAs bases CTC

<400> SEQUENCE: 19
nnncctgtca cttnnn                                                         16

<210> SEQ ID NO 20
<211> LENGTH: 16
<212> TYPE: DNA
<213> ORGANISM: Artificial Sequence
<220> FEATURE:
<223> OTHER INFORMATION: multiply modified oligo
<220> FEATURE:
<221> NAME/KEY: misc_feature
<222> LOCATION: (1)..(3)
<223> OTHER INFORMATION: LNAs TAG
<220> FEATURE:
<221> NAME/KEY: misc_feature
<222> LOCATION: (14)..(14)
<223> OTHER INFORMATION: LNA-C
<220> FEATURE:
<221> NAME/KEY: misc_feature
<222> LOCATION: (15)..(15)
<223> OTHER INFORMATION: palmitoyl-amino-LNA T
<220> FEATURE:
<221> NAME/KEY: misc_feature
<222> LOCATION: (16)..(16)
<223> OTHER INFORMATION: palmitoyl-amino-LNA-5-methy-cytosine

<400> SEQUENCE: 20
nnncctgtca cttnnn                                                         16
```

<210> SEQ ID NO 21
<211> LENGTH: 16
<212> TYPE: DNA
<213> ORGANISM: Artificial Sequence
<220> FEATURE:
<223> OTHER INFORMATION: multiply modified oligo
<220> FEATURE:
<221> NAME/KEY: misc_feature
<222> LOCATION: (1)..(3)
<223> OTHER INFORMATION: LNAs TAG
<220> FEATURE:
<221> NAME/KEY: misc_feature
<222> LOCATION: (14)..(14)
<223> OTHER INFORMATION: LNAs-C
<220> FEATURE:
<221> NAME/KEY: misc_feature
<222> LOCATION: (15)..(15)
<223> OTHER INFORMATION: palmitoyl-amino-LNA T
<220> FEATURE:
<221> NAME/KEY: misc_feature
<222> LOCATION: (16)..(16)
<223> OTHER INFORMATION: palmitoyl-amino-LNA-5-methyl-cytosine

<400> SEQUENCE: 21
nnncctgtca cttnnn                                                   16

<210> SEQ ID NO 22
<211> LENGTH: 15
<212> TYPE: DNA
<213> ORGANISM: Artificial Sequence
<220> FEATURE:
<223> OTHER INFORMATION: modified oligo
<220> FEATURE:
<221> NAME/KEY: misc_feature
<222> LOCATION: (1)..(3)
<223> OTHER INFORMATION: LNAs GTC
<220> FEATURE:
<221> NAME/KEY: misc_feature
<222> LOCATION: (13)..(15)
<223> OTHER INFORMATION: LNAs CTC

<400> SEQUENCE: 22
nnnctcgagc gtnnn                                                    15

<210> SEQ ID NO 23
<211> LENGTH: 15
<212> TYPE: DNA
<213> ORGANISM: Artificial Sequence
<220> FEATURE:
<223> OTHER INFORMATION: modified oligo
<220> FEATURE:
<221> NAME/KEY: misc_feature
<222> LOCATION: (1)..(1)
<223> OTHER INFORMATION: LNA-G
<220> FEATURE:
<221> NAME/KEY: misc_feature
<222> LOCATION: (2)..(2)
<223> OTHER INFORMATION: palmitoyl-amino-LNA T
<220> FEATURE:
<221> NAME/KEY: misc_feature
<222> LOCATION: (3)..(3)
<223> OTHER INFORMATION: LNA-C
<220> FEATURE:
<221> NAME/KEY: misc_feature
<222> LOCATION: (13)..(13)
<223> OTHER INFORMATION: LNA-C
<220> FEATURE:
<221> NAME/KEY: misc_feature
<222> LOCATION: (14)..(14)
<223> OTHER INFORMATION: palmitoyl-amino-LNA T
<220> FEATURE:
<221> NAME/KEY: misc_feature
<222> LOCATION: (15)..(15)
<223> OTHER INFORMATION: LNA-C

```
<400> SEQUENCE: 23
nnnctcgagc gtnnn                                                            15

<210> SEQ ID NO 24
<211> LENGTH: 15
<212> TYPE: DNA
<213> ORGANISM: Artificial Sequence
<220> FEATURE:
<223> OTHER INFORMATION: modified oligo
<220> FEATURE:
<221> NAME/KEY: misc_feature
<222> LOCATION: (1)..(1)
<223> OTHER INFORMATION: LNA-G
<220> FEATURE:
<221> NAME/KEY: misc_feature
<222> LOCATION: (2)..(2)
<223> OTHER INFORMATION: palmitoyl-amino-LNA T
<220> FEATURE:
<221> NAME/KEY: misc_feature
<222> LOCATION: (3)..(3)
<223> OTHER INFORMATION: LNA-C
<220> FEATURE:
<221> NAME/KEY: misc_feature
<222> LOCATION: (13)..(13)
<223> OTHER INFORMATION: LNA-C
<220> FEATURE:
<221> NAME/KEY: misc_feature
<222> LOCATION: (14)..(14)
<223> OTHER INFORMATION: palmitoyl-amino-LNA T
<220> FEATURE:
<221> NAME/KEY: misc_feature
<222> LOCATION: (15)..(15)
<223> OTHER INFORMATION: LNA-C

<400> SEQUENCE: 24
nnnctcgagc gtnnn                                                            15

<210> SEQ ID NO 25
<211> LENGTH: 15
<212> TYPE: DNA
<213> ORGANISM: Artificial Sequence
<220> FEATURE:
<223> OTHER INFORMATION: modified oligo
<220> FEATURE:
<221> NAME/KEY: misc_feature
<222> LOCATION: (1)..(1)
<223> OTHER INFORMATION: LNA-G
<220> FEATURE:
<221> NAME/KEY: misc_feature
<222> LOCATION: (2)..(2)
<223> OTHER INFORMATION: glycyl-amino-LNA-T
<220> FEATURE:
<221> NAME/KEY: misc_feature
<222> LOCATION: (3)..(3)
<223> OTHER INFORMATION: glycyl-amino-LNA-5-methyl-cytosine
<220> FEATURE:
<221> NAME/KEY: misc_feature
<222> LOCATION: (13)..(13)
<223> OTHER INFORMATION: glycyl-amino-LNA-5-methyl-cytosine
<220> FEATURE:
<221> NAME/KEY: misc_feature
<222> LOCATION: (14)..(14)
<223> OTHER INFORMATION: glycyl-amino-LNA-T
<220> FEATURE:
<221> NAME/KEY: misc_feature
<222> LOCATION: (15)..(15)
<223> OTHER INFORMATION: LNA-T

<400> SEQUENCE: 25
nnnctcgagc gtnnn                                                            15

<210> SEQ ID NO 26
```

```
<211> LENGTH: 15
<212> TYPE: DNA
<213> ORGANISM: Artificial Sequence
<220> FEATURE:
<223> OTHER INFORMATION: modified oligo
<220> FEATURE:
<221> NAME/KEY: misc_feature
<222> LOCATION: (1)..(1)
<223> OTHER INFORMATION: LNA-T
<220> FEATURE:
<221> NAME/KEY: misc_feature
<222> LOCATION: (2)..(2)
<223> OTHER INFORMATION: galactosyl-functionalized amino-LNA-T
<220> FEATURE:
<221> NAME/KEY: misc_feature
<222> LOCATION: (3)..(3)
<223> OTHER INFORMATION: LNA-C
<220> FEATURE:
<221> NAME/KEY: misc_feature
<222> LOCATION: (13)..(13)
<223> OTHER INFORMATION: LNA-C
<220> FEATURE:
<221> NAME/KEY: misc_feature
<222> LOCATION: (14)..(14)
<223> OTHER INFORMATION: galactosyl-functionalized amino-LNA-T
<220> FEATURE:
<221> NAME/KEY: misc_feature
<222> LOCATION: (15)..(15)
<223> OTHER INFORMATION: LNA-C

<400> SEQUENCE: 26
nnnctcgagc gtnnn                                                          15

<210> SEQ ID NO 27
<211> LENGTH: 15
<212> TYPE: DNA
<213> ORGANISM: Artificial Sequence
<220> FEATURE:
<223> OTHER INFORMATION: oligo
<220> FEATURE:
<221> NAME/KEY: misc_feature
<222> LOCATION: (1)..(1)
<223> OTHER INFORMATION: LNA-G
<220> FEATURE:
<221> NAME/KEY: misc_feature
<222> LOCATION: (2)..(2)
<223> OTHER INFORMATION: pyrimidine glycyl-amino-LNA
<220> FEATURE:
<221> NAME/KEY: misc_feature
<222> LOCATION: (3)..(3)
<223> OTHER INFORMATION: pyrimidine glycyl-amino-LNA
<220> FEATURE:
<221> NAME/KEY: misc_feature
<222> LOCATION: (13)..(13)
<223> OTHER INFORMATION: pyrimidine glycyl-amino-LNA
<220> FEATURE:
<221> NAME/KEY: misc_feature
<222> LOCATION: (14)..(14)
<223> OTHER INFORMATION: pyrimidine glycyl-amino-LNA
<220> FEATURE:
<221> NAME/KEY: misc_feature
<222> LOCATION: (15)..(15)
<223> OTHER INFORMATION: LNA-C

<400> SEQUENCE: 27
nnnctcgagc gtnnc                                                          15

<210> SEQ ID NO 28
<211> LENGTH: 15
<212> TYPE: DNA
<213> ORGANISM: Artificial Sequence
<220> FEATURE:
<223> OTHER INFORMATION: ligo
<220> FEATURE:
<221> NAME/KEY: misc_feature
```

```
<222> LOCATION: (1)..(1)
<223> OTHER INFORMATION: LNA-G
<220> FEATURE:
<221> NAME/KEY: misc_feature
<222> LOCATION: (2)..(2)
<223> OTHER INFORMATION: pyrimidine glycyl-amino-LNA
<220> FEATURE:
<221> NAME/KEY: misc_feature
<222> LOCATION: (3)..(3)
<223> OTHER INFORMATION: pyrimidine LNA monomer
<220> FEATURE:
<221> NAME/KEY: misc_feature
<222> LOCATION: (13)..(13)
<223> OTHER INFORMATION: pyrimidine LNA monomer
<220> FEATURE:
<221> NAME/KEY: misc_feature
<222> LOCATION: (14)..(14)
<223> OTHER INFORMATION: palmitoyl-amino-LNA-T
<220> FEATURE:
<221> NAME/KEY: misc_feature
<222> LOCATION: (15)..(15)
<223> OTHER INFORMATION: LNA-C

<400> SEQUENCE: 28
nnnctcgagc gtnnn                                                       15

<210> SEQ ID NO 29
<211> LENGTH: 15
<212> TYPE: DNA
<213> ORGANISM: Artificial Sequence
<220> FEATURE:
<223> OTHER INFORMATION: oligo
<220> FEATURE:
<221> NAME/KEY: misc_feature
<222> LOCATION: (1)..(1)
<223> OTHER INFORMATION: LNA-G
<220> FEATURE:
<221> NAME/KEY: misc_feature
<222> LOCATION: (2)..(2)
<223> OTHER INFORMATION: palmitoyl-amino-LNA-T
<220> FEATURE:
<221> NAME/KEY: misc_feature
<222> LOCATION: (3)..(3)
<223> OTHER INFORMATION: glycyl-amino-LNA-T
<220> FEATURE:
<221> NAME/KEY: misc_feature
<222> LOCATION: (13)..(13)
<223> OTHER INFORMATION: glycyl-amino-LNA-T
<220> FEATURE:
<221> NAME/KEY: misc_feature
<222> LOCATION: (14)..(14)
<223> OTHER INFORMATION: palmitoyl-amino-LNA-T
<220> FEATURE:
<221> NAME/KEY: misc_feature
<222> LOCATION: (15)..(15)
<223> OTHER INFORMATION: LNA-C

<400> SEQUENCE: 29
nnnctcgagc gtnnn                                                       15
```